US008642040B2

(12) United States Patent
Mi et al.

(10) Patent No.: US 8,642,040 B2
(45) Date of Patent: Feb. 4, 2014

(54) METHODS FOR PROMOTING MYELINATION, NEURONAL SURVIVAL AND OLIGODENDROCYTE DIFFERENTIATION VIA ADMINISTRATION OF SP35 OR TRKA ANTAGONISTS

(75) Inventors: Sha Mi, Belmont, MA (US); Vincent Jung, Belmont, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 1068 days.

(21) Appl. No.: 12/375,117

(22) PCT Filed: Jul. 24, 2007

(86) PCT No.: PCT/US2007/016589
§ 371 (c)(1),
(2), (4) Date: Nov. 23, 2009

(87) PCT Pub. No.: WO2008/013782
PCT Pub. Date: Jan. 31, 2008

(65) Prior Publication Data
US 2010/0074907 A1    Mar. 25, 2010

Related U.S. Application Data

(60) Provisional application No. 60/832,586, filed on Jul. 24, 2006, provisional application No. 60/836,652, filed on Aug. 10, 2006.

(51) Int. Cl.
*A61K 39/00* (2006.01)
(52) U.S. Cl.
USPC ..................................................... 424/172.1
(58) Field of Classification Search
None
See application file for complete search history.

(56) References Cited

U.S. PATENT DOCUMENTS

| | | | |
|---|---|---|---|
| 5,468,872 | A | 11/1995 | Glicksman et al. |
| 5,574,009 | A | 11/1996 | Cohen et al. |
| 6,034,119 | A | 3/2000 | Ono et al. |
| 6,610,500 | B1 | 8/2003 | Saragovi et al. |
| 6,881,719 | B2 | 4/2005 | Saragovi et al. |
| 6,919,426 | B2 | 7/2005 | Boone et al. |
| 7,785,829 | B2 | 8/2010 | Mi et al. |
| 8,058,406 | B2 | 11/2011 | Mi et al. |
| 8,128,926 | B2 | 3/2012 | Mi et al. |
| 8,153,580 | B2 | 4/2012 | Mi et al. |
| 8,460,657 | B2 * | 6/2013 | Nykjær et al. ............ 424/130.1 |
| 2002/0077295 | A1 | 6/2002 | Strittmatter |
| 2003/0032589 | A1 | 2/2003 | Bartke et al. |
| 2004/0186044 | A1 | 9/2004 | Cosgaya et al. |
| 2005/0271655 | A1 | 12/2005 | Lee et al. |
| 2006/0009388 | A1 | 1/2006 | Mi et al. |
| 2006/0058223 | A1 | 3/2006 | Mi et al. |
| 2007/0059793 | A1 | 3/2007 | Mi et al. |
| 2009/0017039 | A1 | 1/2009 | Mi et al. |
| 2009/0175846 | A1 | 7/2009 | Mi et al. |
| 2009/0175872 | A1 | 7/2009 | Mi et al. |
| 2009/0246189 | A1 | 10/2009 | Mi et al. |
| 2010/0143362 | A1 | 6/2010 | Walmsley et al. |
| 2010/0204304 | A1 | 8/2010 | Mi et al. |
| 2010/0297121 | A1 | 11/2010 | Mi |
| 2011/0311542 | A1 | 12/2011 | Mi et al. |
| 2012/0014960 | A1 | 1/2012 | Mi et al. |

FOREIGN PATENT DOCUMENTS

| | | |
|---|---|---|
| JP | 9-502730 A | 3/1997 |
| JP | 2000-501416 A | 2/2000 |
| JP | 2000-514420 A | 10/2000 |
| WO | WO 95/07911 A1 | 3/1995 |
| WO | WO 95/21193 A1 | 8/1995 |
| WO | WO 97/40847 A1 | 11/1997 |
| WO | WO 97/49406 A1 | 12/1997 |
| WO | WO 99/48908 A2 | 9/1999 |
| WO | WO 01/51520 A2 | 7/2001 |
| WO | WO 02/060955 A2 | 8/2002 |
| WO | WO 02/096948 A2 | 12/2002 |
| WO | WO 03/031462 A2 | 4/2003 |
| WO | WO 2004/014311 A2 | 2/2004 |
| WO | WO 2004/085648 A2 | 10/2004 |
| WO | WO 2005/016955 A2 | 2/2005 |
| WO | WO 2006/136006 A1 | 12/2006 |
| WO | WO 2007/008547 A2 | 1/2007 |
| WO | WO 2007/056161 A1 | 5/2007 |
| WO | WO 2007/064882 A2 | 6/2007 |
| WO | WO 2007/092370 A2 | 8/2007 |
| WO | WO 2007/098283 A2 | 8/2007 |
| WO | WO 2008/013782 A2 | 1/2008 |
| WO | WO 2008/058736 A1 | 5/2008 |

OTHER PUBLICATIONS

Barbacid, M., "The Trk Family of Neurotrophin Receptors," *Journal of Neurobiology* 25(11):1386-1403, John Wiley & Sons, United States (1994).

Baumann, N. and Pham-Dinh, D., "Biology of Oligodendrocyte and Myelin in Mammalian Central Nervous System," *Physiol. Rev.* 81(2):871-927, American Physiological Society, United States (2001).

Binder, D.K., et al., "Selective Inhibition of Kindling Development by Intraventricular Administration of TrkB Receptor Body," *J. Neurosci.* 19(4):1424-1436, Society for Neuroscience, United States (1999).

Brittis, P.A. and Flanagan, J.G., "Nogo Domains and a Nogo Receptor: Implications for Axon Regeneration," *Neuron* 30:11-14, Cell Press, United States (2001).

Buffo, A., et al., "Application of Neutralizing Antibodies against NI-35/250 Myelin-Associated Neurite Growth Inhibitory Proteins to the Adult Rat Cerebellum Induces Sprouting of Uninjured Purkinje Cell Axons," *J. Neurosci.* 20(6):2275-2286, Society for Neuroscience, United States (2000).

(Continued)

*Primary Examiner* — Gregory S Emch
(74) *Attorney, Agent, or Firm* — Sterne, Kessler, Goldstein & Fox P.L.L.C.

(57) ABSTRACT

This invention relates to methods for promoting myelination, neuronal survival, and oligodendrocyte differentiation and treating demyelination and dysmyelination disease by the administration of a TrkA antagonist. The invention also relates to methods of inhibiting or decreasing Sp35 expression by the use of a TrkA antagonist. Additionally, the invention relates generally to methods for blocking Sp35 and TrkA interaction and inhibiting or decreasing TrkA phosphorylation by the administration of a Sp35 antagonist.

10 Claims, 13 Drawing Sheets

(56) References Cited

OTHER PUBLICATIONS

Figure 1:
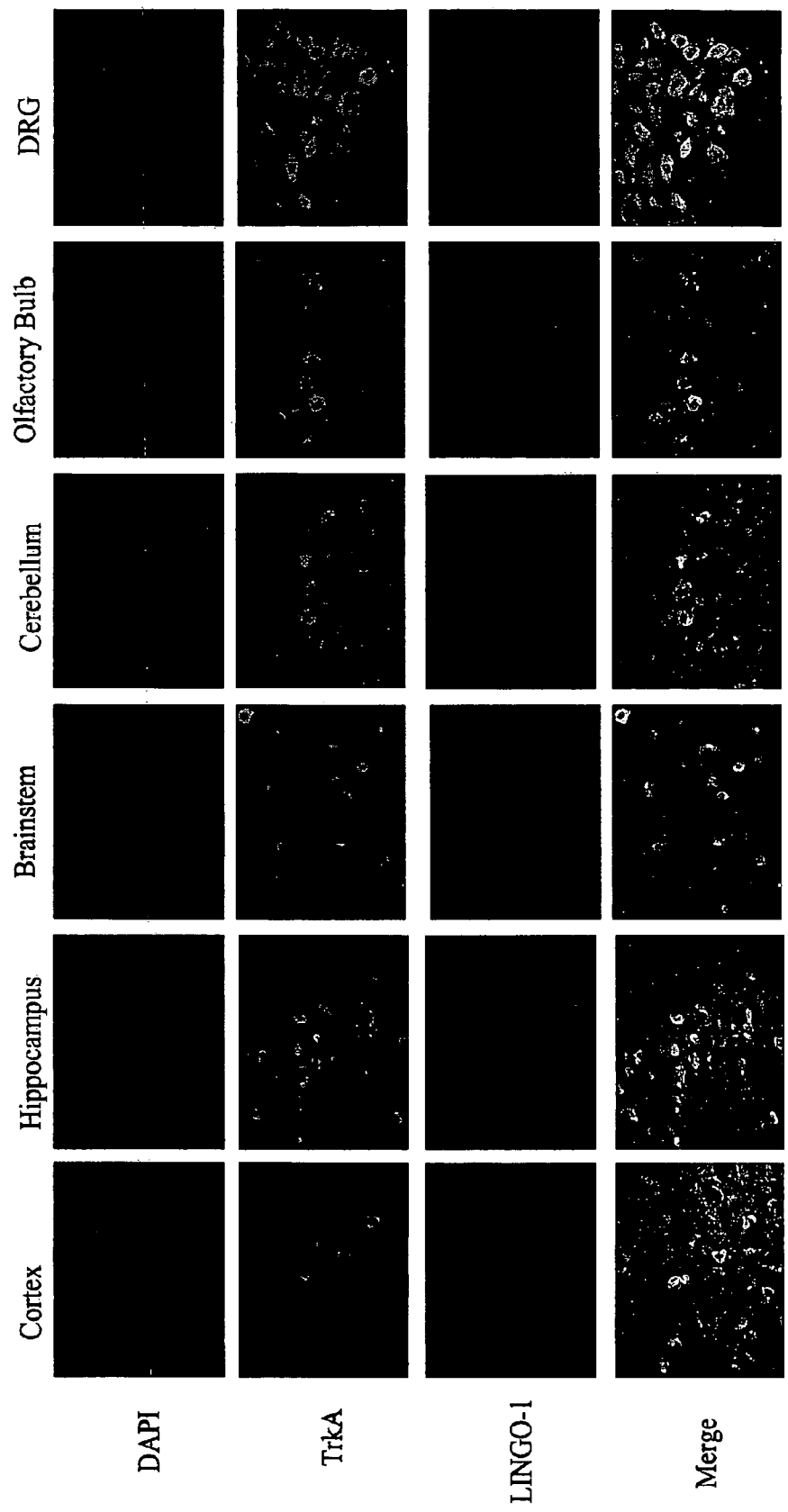

Cattaneo, A., et al., "Functional Blockade of Tyrosine Kinase A in the Rat Basal Forebrain by a Novel Antagonistic Anti-Receptor Monoclonal Antibody" *J. Neuroscience* 19(22):9687-9697, Society for Neuroscience, United States (1999).

Cellerino, A., et al., "Reduced Size of Retinal Ganglion Cell Axons and Hypomyelination in Mice Lacking Brain-Derived Neurotrophic Factor," *Mol. Cell. Neurosci.* 9:397-408, Academic Press, United States (1997).

Chakrabarti, K., et al., "Critical Role for Kalirin in Nerve Growth Facotr Signaling through TrkA," *Mol. Cell. Biol.* 25(12):5106-5118, American Society for Microbiology, United States (2005).

Chan, J.R., et al., "NGF Controls Axonal Receptivity to Myelination by Schwann Cells or Oligodendrocytes," *Neuron* 43:183-191, Cell Press, United States (2004).

Chang, A., et al., "Premyelinating Oligodendrocytes in Chronic Lesions of Multiple Sclerosis," *N. Engl. J. Med.* 346(3):165-173, Massachusetts Medical Society, United States (2002).

Chao, M.V., et al., "Neurotrophin signaling in health and disease," *Clinical Science* 110:167-173, The Biochemical Society, Great Britain (2006).

Chen, M.S., et al., "Nogo-A is a myelin-associated neurite outgrowth inhibitor and an antigen for monoclonal antibody IN-1," *Nature* 403:434-439, Macmillian Magazines Ltd, England (2000).

Chen, X., et al., "A Chemical-Genetic Approach to Studyiing Neurotrophin Signaling," *Neuron* 46:13-21, Elsevier, Inc., United States (2005).

Chiabrando, G.A., et al., "Low-Density Lipoprotein Receptor-Related Protein Mediates in PC12 Cell Cultures the Inhibition of Nerve Growth Factor-Promoted Neurite Outgrowth by Pregnancy Zone Protein and $\alpha_2$-Macroglobulin," *J. Neurosci. Res.* 70:57-64, Wiley-Liss, Inc., United States (2002).

Colello, R.J., and Pott, U., "Signals that Initiate Myelination in the Developing Mammalian Nervous System," *Mol. Neurobiol.* 15(1):83-100, Humana Press Inc., United States (1997).

Dey, N., et al., "CSK negatively regulates nerve growth factor induced neural differentiation and augments AKT kinase activity," *Exp. Cell Res.* 307(1):1-14, Elsevier Inc., United States (2005).

Domeniconi, M., et al., "Myelin-Associated Glycoprotein Interacts with Nogo66 Receptor to Inhibit Neurite Outgrowth," *Neuron* 35:283-290, Cell Press, United States (2002).

Domeniconi M., and Filbin, M.T., "Overcoming inhibitors in myelin to promote axonal regeneration," *J. Neurol. Sci.* 233:43-47, Elsevier B.V., Netherlands (2005).

Eggert, A., et al. "Different Effects of TrkA Expression in Neuroblastoma Cell Lines With or Without *MYCN* Amplification," *Med. Pediatr. Oncol.* 35(6):623-627, Wiley-Liss, Inc., United States (2000).

Esposito, D., et al., "The Cytoplasmic and Transmembrane Domains of the p75 and Trk A Receptors Regulate High Affinity Binding to Nerve Growth Factor," *J. Biol. Chem.* 276(35): 32687-32695, American Society for Biochemistry and Molecular Biology, United States (2001).

Ferraro, G.B., et al., "Molecular Targets to Promote Central Nervous System Regeneration," *Current Neurovascular Research* 1:61-75, Betham Science Publishers Ltd., Netherlands (2004).

Gallo, G., et al., "The trkA Receptor Mediates Growth Cone Turning toward a Localized Source of Nerve Growth Factor," *J. Neurosci.* 17(14): 5445-5454, Society for Neuroscience, United States (1997).

Grandpré, T., et al., "Identification of the Nogo inhibitor of axon regeneration as a Reticulon protein," *Nature* 403: 439-444, Macmillan Magazines Ltd., England (2000).

Grimpe, B., et al. "The Critical Role of Basement Membrane-Independent Laminin γ1 Chain durng Axon Regeneration in the CNS," *J. Neurosci.* 22(8):3144-3160, Society for Neuroscience, United States (2002).

Hefti, F.F., et al., "Novel class of pain drugs based on antagonism of NGF," *Trends in Pharmacological Sciences* 27(2):85-91, Elsevier Ltd., England (2006).

Höke, A., et al., "Glial Cell Line-Derived Neurotrophic Factor Alters Axon Schwann Cell Units and Promotes Myelination in Unmyelinated Nerve Fibers," *J. Neurosci.* 23(2):561-567, Society for Neuroscience, United States (2003).

Jones, L.L., et al., "NG2 is a Major Chondrointin Sulfate Proteoglycan Produced after Spinal Cord Injury and is Expressed by Macrophages and Oligodendrocyte Progenitors," *J. Neurosci.* 22(7):2792-2803, Society for Neuroscience, United States 2002.

Jonnala, R.R., and Buccafusco, J.J., "Inhibition of nerve growth factor signaling by peroxynitrite," *J. Neurosci. Res.* 63(1):27-34, Wiley-Liss, United States (2001).

Kaplan, D.R., and Miller, F.D., "Neurotrophin signal transduction in the nervous system," *Current Opinion in Neurobiology* 10:381-391, Elsevier Science Ltd., England (2000).

Kimpinski, K., "The Anti-P75 Antibody, MC192, and Brain-Derived Neurotrophic Factor Inhibit Nerve Growth Factor-Dependent Neurite Growth from Adult Sensory Neurons," *Neuroscience* 93(1):253-263, Elsevier Science Ltd., England (1999).

Kleitman, N., et al., "Tissue Culture Methods for the Study of Myelination" in *Culture Nerve Cells*, Banker and Goslin, eds., pp. 337-377, MIT Press, Cambridge, Massachusetts, United States (1991).

Lee, X., et al., "NGF Regulates the Expression of Axonal LINGO-1 to Inhibit Ogliodendrocyte Differentiation and Myelination," *J. Neurosci.* 27(1):220-225, Society for Neuroscience, United States (2007).

Lehmann, M., et al., "Inactivation of Rho Signaling Pathway Promotes CNS Axon Regeneration," *J. Neurosci.* 19(17):7537-7547, Society for Neuroscience, United States (1999).

Lemke, G., "Myelin and Myelination," in an *Introduction to Molecular Neurobiology*, Z. Hall, ed., pp. 281-309, Sinauer Associates, Inc., United States (1992).

Liu, N., et al., "Enhancement of Schwann cell myelin formation by K252a in the trembler-J mouse dorsal root ganglion explant culture" J Neurosci. Res. 79(3):310-317, Wiley-Liss, United States (2005).

Llovera, M., et al, "Trk is a calmodulin-binding protein: implications for receptor processing," *J. Neurochem* 88:422-433, International Society for Neurochemistry, England (2004).

Markus, A., et al., "Raf and Akt Mediate Distinct Aspects of Sensory Axon Growthy," *Neuron* 35:65-76, Cell Press, United States (2002).

Marmigère, F., et al., "The Runx1/AML1 transcription factor selectively regulates development and survival of TrkA nociceptive sensory neurons," *Nat. Neurosci.* 9(2):180-187, Nature Publishing Group, United States (2006).

Marsh, H.N., et al., "SHP-1 negatively regulated neuronal survival by functioning as a TrkA phosphatase," *J. Cell Biol* 163(5): 999-1010, Rockefeller University Press, United States (2003).

McKerracher, L., et al., "Identification of Myelin-Associated Glycoprotein as a Major Myelin-Derived Inhibitor of Neurite Growth," *Neuron* 13:805-811, Cell Press, United States (1994).

Mi, A., et al., "Synctin is a captive retroviral envelope protein involved in human placental morphogenesis," *Nature* 403:785-789, Nature Publishing Group, England (2000).

Mi, S., et al. "LINGO-1 is a component of the Nogo-66 receptor/p75 signaling complex," *Nat. Neurosci.* 7(3):221-228, Nature Publishing Group, England (2004).

Mi, S., et al. "LINGO-1 negatively regulates myelination by ogliodendrocytes," *Nat. Neurosci* 8(6):745-751, Nature Publishing Group, England (2005).

Michailov, G.V., et al., "Axonal Neuregulin-1 Regulates Myelin Sheath Thickness," *Science* 304:700-703, American Academy for the Advancement of Science, United States (2004).

Mikol, D.D. and Stefansson, K., "A Phosphatidylinositol-linked Peanut Agglutinin-binding Glycoprotein in Central Nervous System Myelin and on Oligodendrocytes," *J. Cell. Biol.* 106:1273-1279, Rockfeller University Press, United States (1988).

Miller, D.R., et al., "Increased Neurite Outgrowth Induced by Inhibition of Protein Tyrosine Kinase Activity in PC12 Pheochromocytoma Cells," *J. Neurochem.* 60(6):2134-2144, International Society for Neurochemistry, England (1993).

Mukhopadhyay, G., et al., "A Novel Role for Myelin-Associated Glycoprotein as an Inhibitor of Axonal Regeneration," *Neuron* 13:757-767, Cell Press Ltd., United States (1994).

(56) References Cited

OTHER PUBLICATIONS

Nusser, N., et al., "Nerve Growth Factor Signals through TrkA, Phosphatidylinositol 3-Kinase, and Rac1 to Inactivate RhoA during the Initiation of Neuronal Differentiation of PC12 Cells," *J. Biol Chem.* 277(39): 35840-35846, American Society for Biochemistry and Molecular Biology, Inc., United States (2002).

Parran, D., et al., "Methylmercury decreases NGF-induced TrkA autophosphorylation and neurite outgrowth in PC12 cells," *Developmental Brain Research 141*:71-81, Elsevier Science B.V., Netherlands (2003).

Persengiev, S.P., and Kilpatrick, D.L., "Nerve growth factor induced differentiation of neuronal cells requires gene methylation," *NeuroReport 8*:227-231, Rapid Science Publishers, England (1996).

Pesavento, E., "Blocking the NGF-TrkA Interaction Rescues the Developmental Loss of LTP in the Rat Visual Cortex: Role of the Cholinergic System," *Neuron 25*:165-75, Cell Press, United States (2000).

Rahkit, S., et al., "Nerve Growth Factor Stimulation of p42/p44 Mitogen-Activated Protein Kinase in PC12 Cells: Role of $G_{i/o}$, G Protein-Coupled Receptor Kinase 2, β-Arrestin I, and Endocytic Processing," *Mol. Pharmacol.* 60(1):63-70, American Society for Pharmacology and Experimental Therapeutics, United States (2001).

Rueda, D., et al. "The Endocannabinoid Anandamide Inhibits Neuronal Progenitor Cell Differentiation through Attenuation of the Rap1/B-Raf/ERK Pathway," *J. Biol Chem.* 277(48):46645-46650, American Society for Biochemistry and Molecular Biology, Inc., United States (2002).

Rutihauser, U. and Jesseli T.M., "Cell Adhesion Molecules in Vertebrate Neural Development," *Physiol Rev.* 68(3):819-857, American Physiological Society, United States (1998).

Saragovi, H.U., and Burgess, K., "Small molecule and protein-based neurotrophic ligands: agonists and antagonists as therapeutic agents," *Exp. Opin. Ther. Patents* 9(6): 737-751, Ashley Publications Ltd., England (1999).

Takatori, M., et al., "Local Anesthetics Suppress Nerve Growth Factor-Mediated Neurite Outgrowth by Inhibition of Tyrosine Kinase Activity of TrkA," *Anesth. Analg.* 102: 462-467, International Anesthesia Research Society, United States (2006).

Taveggia, C., et al. "Neuregulin-1 Type III Determines the Ensheathment Fate of Axons," *Neuron 47*:681-694, Elsevier Inc., United States (2005).

Tong, J.X., et al., "Intracellular Calcium Levels Influence Apoptosis in Mature Sensory Neurons after Trophic Factor Deprivation," *Exp. Neurol.* 138:45-52, Academic Press, Inc., United States (1996).

Urfer, R., et al., "High Resolution Mapping of the Binding Site of TrkA for Nerve Growth Factor and TrkC for Neurotrophin-3 on the Second Immunoglobulin-like Domain of the Trk Receptors," *J. Biol. Chem.* 273(10):5829-5840, American Society for Biochemistry and Molecular Biology, Inc., United States (1998).

Wang, K.C., et al., "Oligodendrocyte-myelin glycoprotein is a Nogo receptor ligand that inhibits neurite outgrowth," *Nature 417*: 941-944, Nature Publishing Group, England (2002).

Woronowicz, A., et al. "Trypanosome trans-sialidase targets TrkA tyrosine kinase receptor and induces receptor internalization and activation," *Glycobiology 14*(11):987-998, Oxford University Press, United States (2004).

International Search Report for International Patent Application No. PCT/US07/16589, International Searching Authority, United States, mailed on Oct. 2, 2008.

Written Opinion of the International Searching Authority for International Patent Application No. PCT/US07/16589, International Searching Authority, United States, mailed on Oct. 2, 2008.

International Preliminary Report on Patentability for International Patent Application No. PCT/US2007/016589, International Bureau of WIPO, Switzerland, mailed on Jan. 27, 2009.

Co-pending U.S. Appl. No. 13/356,413, inventors Mi et al., filed Jan. 23, 2012 (Not Published).

Co-pending U.S. Appl. No. 13/414,222, inventors Mi et al., filed Mar. 7, 2012 (Not Published).

Roux, P.P., et al., "K252a and CEP1347 Are Neuroprotective Compounds That Inhibit Mixed-lineage Kinase-3 and Induce Activation of Akt and ERK," *The Journal of Biological Chemistry* 277(51):49473-49480, The American Society for Biochemistry and Molecular Biology, Inc., United States (2002).

Office Action mailed Oct. 2, 2012, in Japanese Patent Application No. 2009-521795 (English language translation included).

\* cited by examiner

Fig. 1 - LINGO-1 colocalizes with TrkA in different types of neurons (brain and spinal cord tissues)

Figure 2:
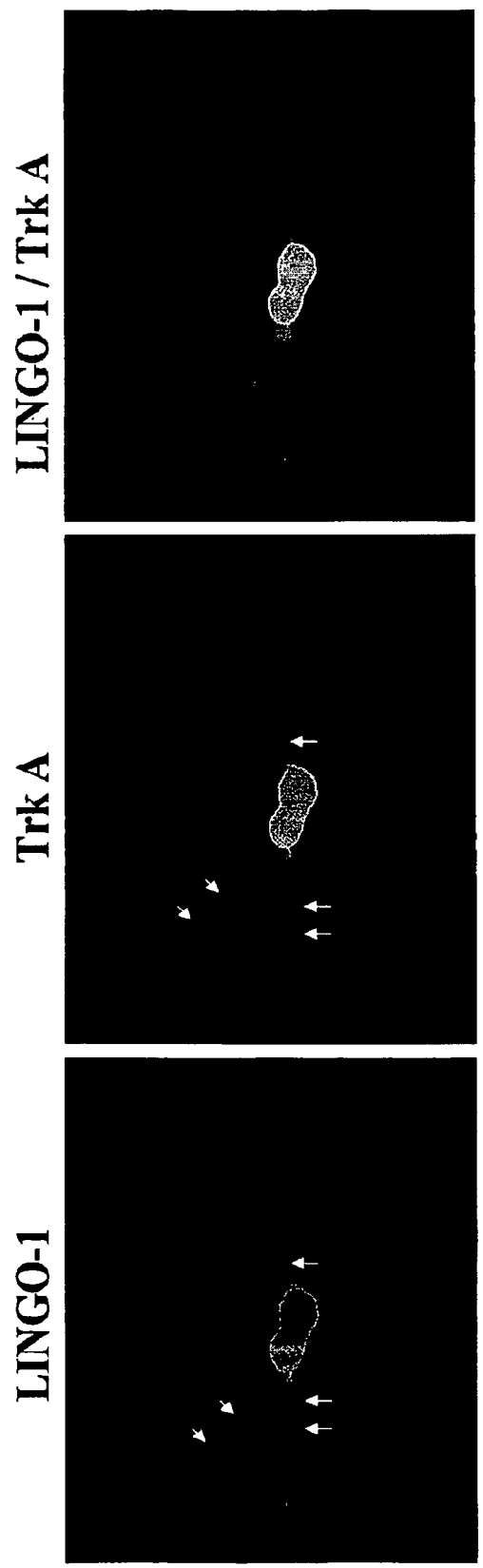

Fig. 2 - LINGO-1 co-localizes with TrkA in DRG neurons (in culture)

Figure 3:
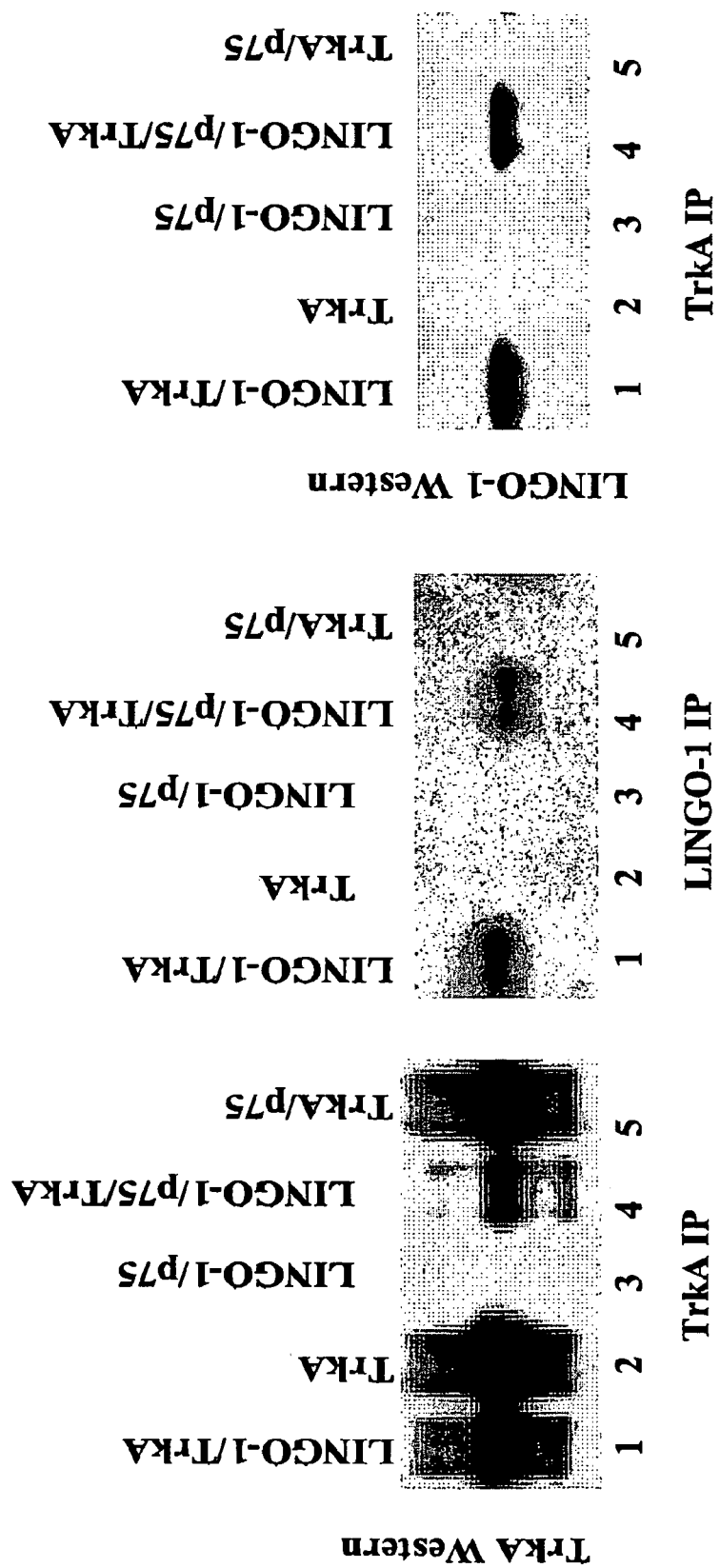

Fig. 3 - LINGO-1 binds to TrkA by immunoprecipitation (293T cells)

Figure 4:
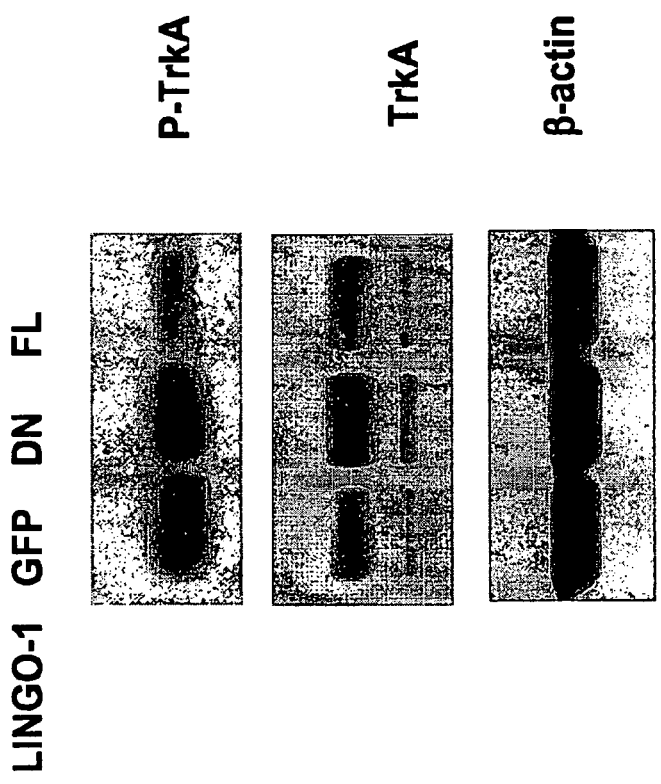

Fig. 4 – LINGO-1 blocks TrkA phosphorlyation in OLG-DRG cocultures

Figure 5:
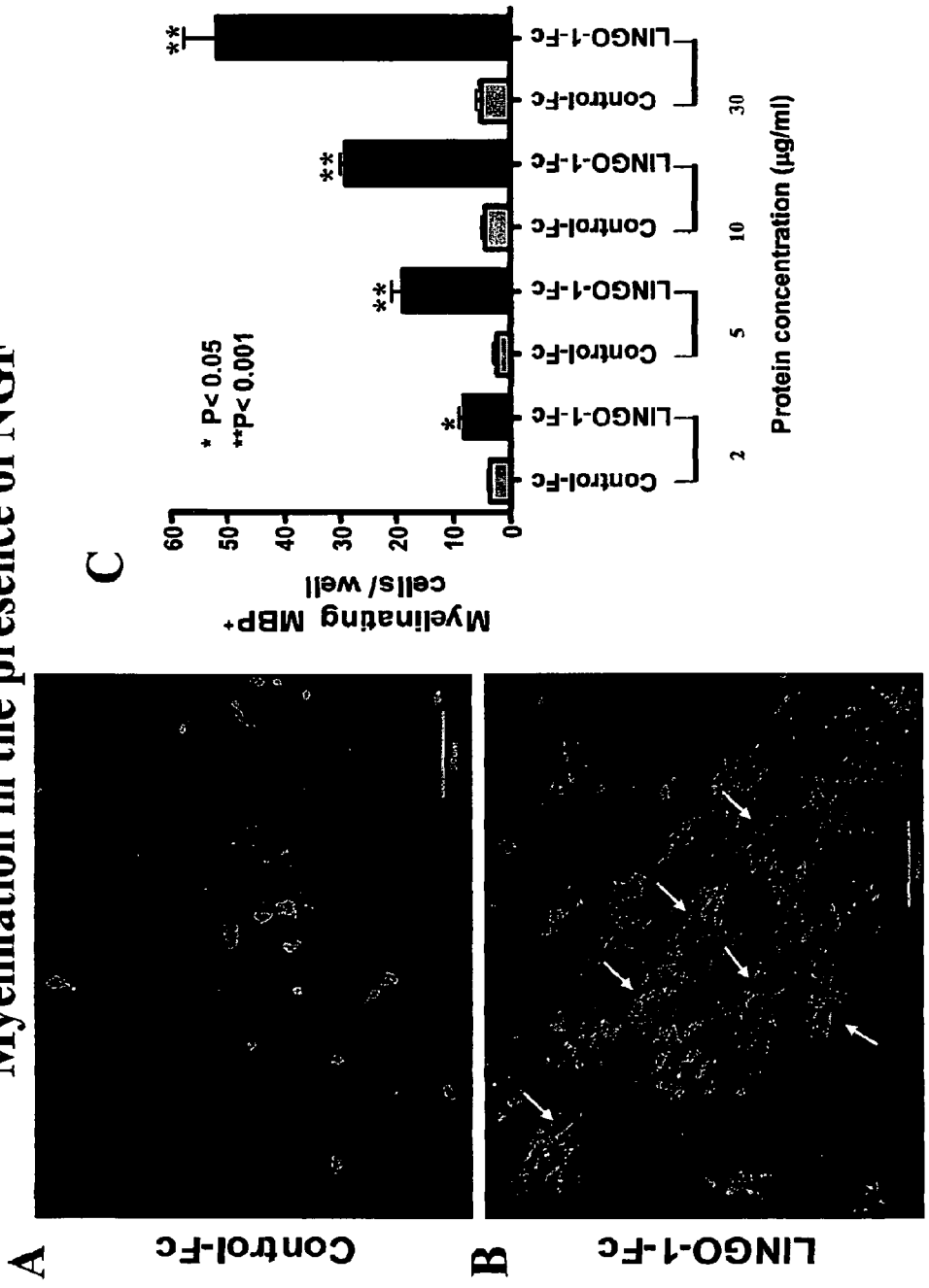
Figure 6:
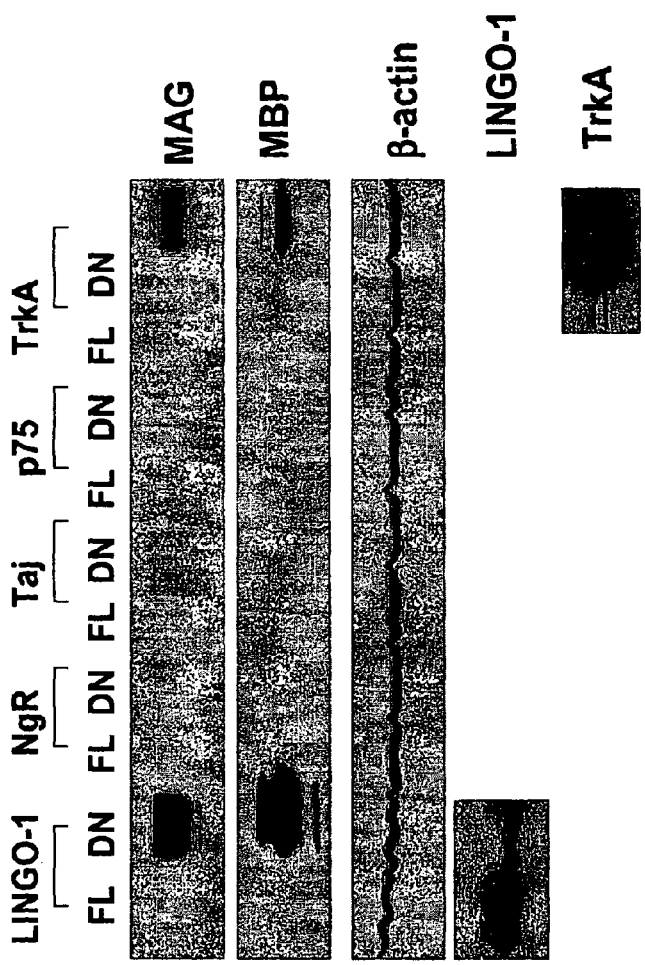

Fig. 5 - LINGO-1 antagonists promote oligodendrocyte Myelination in the presence of NGF Fig. 6 - Blocking either LINGO-1 or TrkA promotes CNS myelination in the present of NGF

* DRG-OPC cocultures (3 weeks) infected with corresponding viruses.

Figure 7:
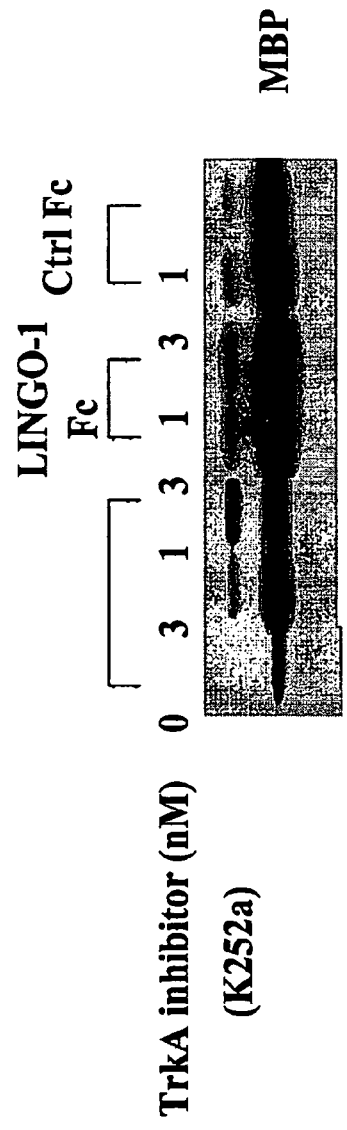

Fig. 7 - TrkA inhibitor(K252a) promotes myelination of OLG-DRG coculture

Figure 8:
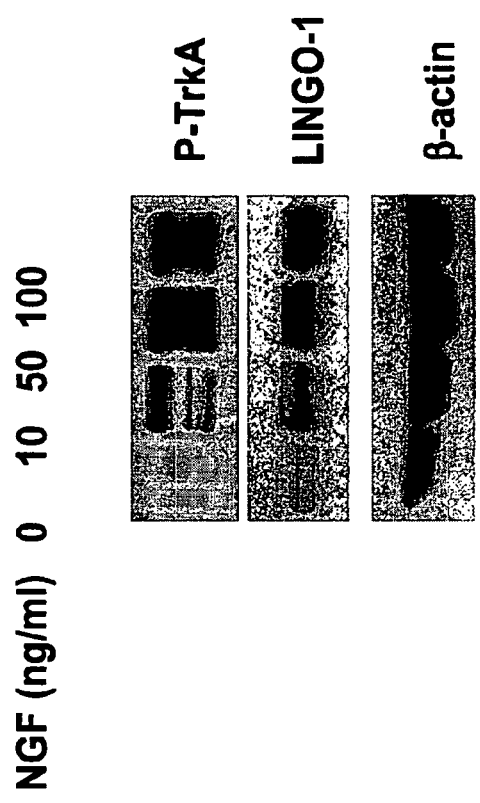

Fig. 8 - NGF induces LINGO-1 upregulation in oligodendrocyte/DRG coculture

Figure 9:
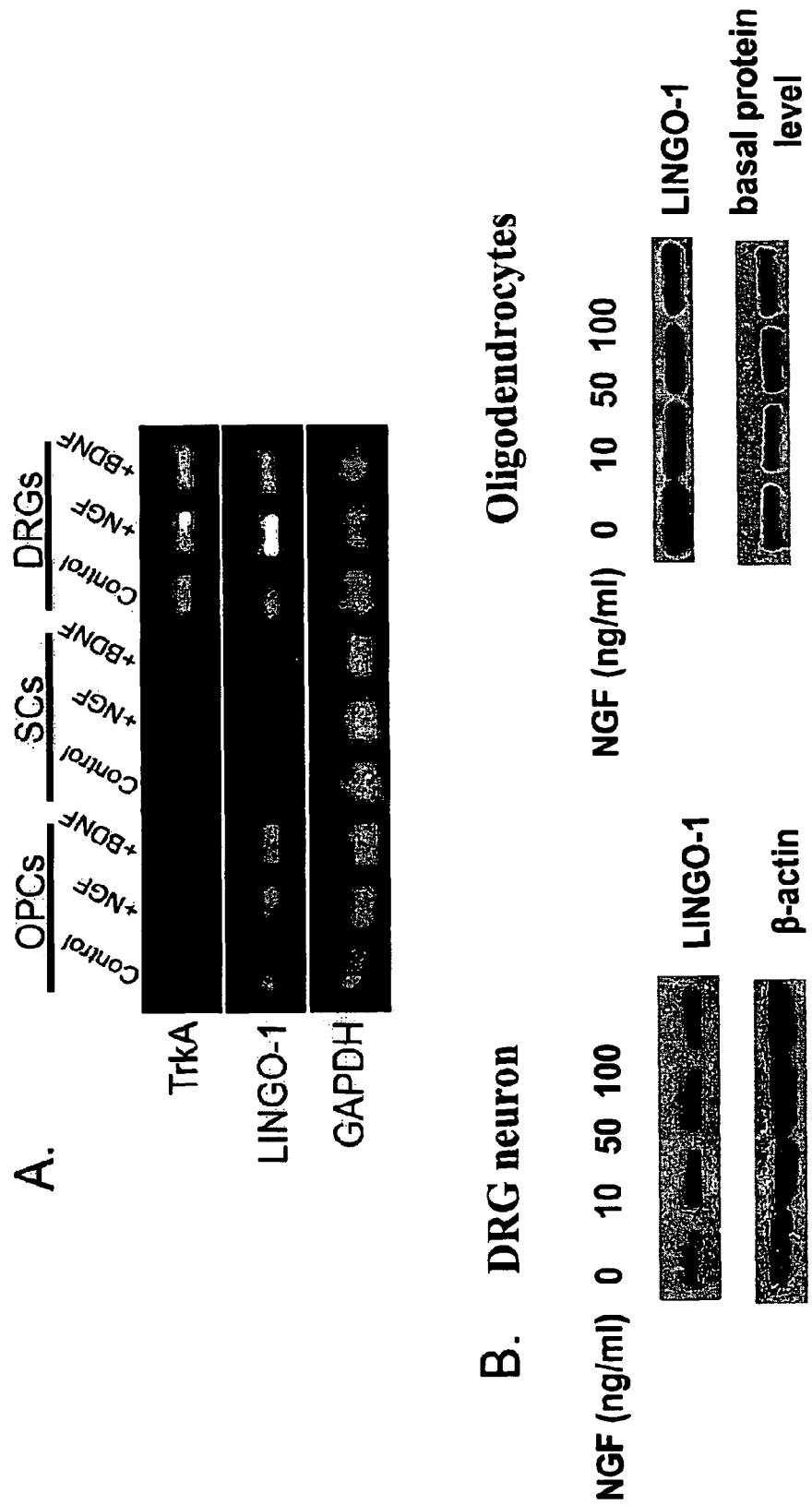
Figure 10:
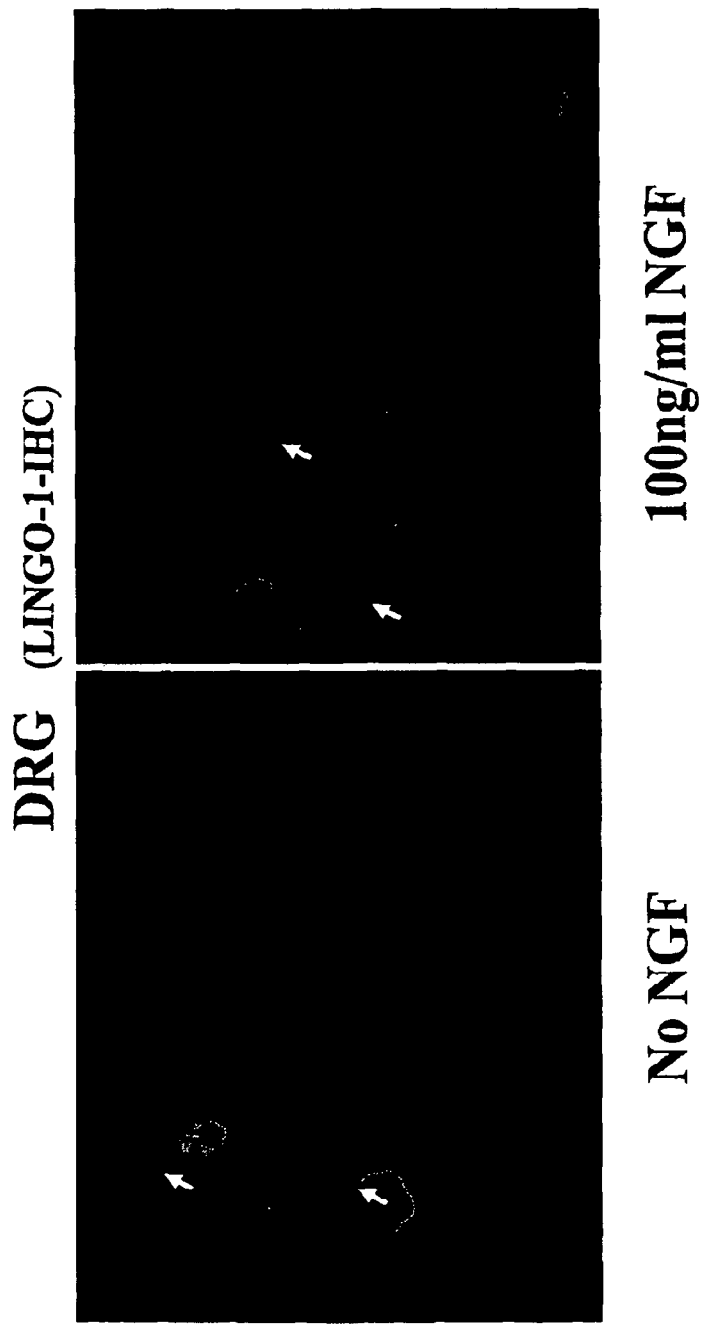
Figure 11:
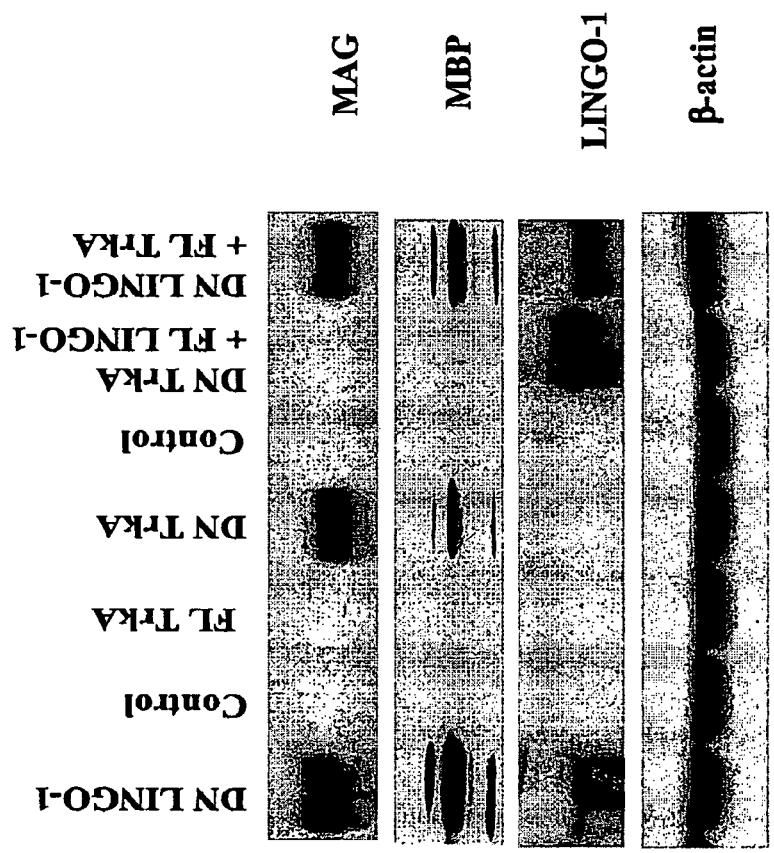

Fig. 9 - NGF upregulates LINGO-1 expression in DRG neurons, but not in oligodendrocytes Fig. 10 - NGF upregulates LINGO-1 expression in axons of DRG neurons Fig. 11 - TrkA is an upstream signaling of LINGO-1

```
                              SEQUENCE LISTING

<160> NUMBER OF SEQ ID NOS: 15

<210> SEQ ID NO 1
<211> LENGTH: 1845
<212> TYPE: DNA
<213> ORGANISM: Homo sapiens

<400> SEQUENCE: 1
atgctggcgg ggggcgtgag gagcatgccc agcccctcc tggcctgctg gcagcccatc      60
ctcctgctgg tgctgggctc agtgctgtca ggctcggcca cgggctgccc gccccgctgc     120
gagtgctccg cccaggaccg cgctgtgctg tgccaccgca agcgctttgt ggcagtcccc     180
gagggcatcc ccaccgagac gcgcctgctg gacctaggca agaaccgcat caaaacgctc     240
aaccaggacg agttcgccag cttcccgcac ctggaggagc tggagctcaa cgagaacatc     300
gtgagcgccg tggagcccgg cgccttcaac aacctcttca acctccggac gctgggtctc     360
cgcagcaacc gcctgaagct catcccgcta ggcgtcttca ctggcctcag caacctgacc     420
aagctggaca tcagcgagaa caagattgtt atcctgctgg actacatgtt tcaggacctg     480
tacaacctca agtcactgga ggttggcgac aatgacctcg tctacatctc tcaccgcgcc     540
ttcagcggcc tcaacagcct ggagcagctg acgctggaga atgcaacct gacctccatc     600 cccaccgagg cgctgtccca cctgcacggc ctcatcgtcc tgaggctccg gcacctcaac     660
atcaatgcca tccgggacta ctccttcaag aggctctacc gactcaaggt cttggagatc     720
tcccactggc cctacttgga caccatgaca cccaactgcc tctacggcct caacctgacg     780
tccctgtcca tcacacactg caatctgacc gctgtgccct acctggccgt ccgccaccta     840
gtctatctcc gcttcctcaa cctctcctac aaccccatca gcaccattga gggctccatg     900
ttgcatgagc tgctccggct gcaggagatc cagctggtgg gcgggcagct ggccgtggtg     960
gagccctatg ccttccgcgg cctcaactac ctgcgcgtgc tcaatgtctc tggcaaccag    1020
ctgaccacac tggaggaatc agtcttccac tcggtgggca acctggagac actcatcctg    1080
gactccaacc cgctggcctg cgactgtcgg ctcctgtggg tgttccggcg ccgctggcgg    1140
ctcaacttca accggcagca gcccacgtgc gccacgcccg agtttgtcca gggcaaggag    1200
ttcaaggact ccctgatgt gctactgccc aactacttca cctgccgccg cgcccgcatc    1260
cgggaccgca aggcccagca ggtgtttgtg gacgagggcc acacggtgca gtttgtgtgc    1320
cgggccgatg gcgacccgcc gccgccatc tctggctct caccccgaaa gcacctggtc    1380
tcagccaaga gcaatgggcg gctcacagtc ttccctgatg gcacgctgga ggtgcgctac    1440
gcccaggtac aggacaacgg cacgtacctg tgcatcgcgg ccaacgcggg cggcaacgac    1500
```

```
tccatgcccg cccacctgca tgtgcgcagc tactcgcccg actggcccca tcagcccaac    1560
aagaccttcg ctttcatctc caaccagccg ggcgagggag aggccaacag cacccgcgcc    1620
actgtgcctt tccccttcga catcaagacc ctcatcatcg ccaccaccat gggcttcatc    1680
tctttcctgg gcgtcgtcct cttctgcctg gtgctgctgt ttctctggag ccggggcaag    1740
ggcaacacaa agcacaacat cgagatcgag tatgtgcccc gaaagtcgga cgcaggcatc    1800
agctccgccg acgcgccccg caagttcaac atgaagatga tatga                    1845
```

<210> SEQ ID NO 2
<211> LENGTH: 614
<212> TYPE: PRT
<213> ORGANISM: Homo sapiens

<400> SEQUENCE: 2

```
Met Leu Ala Gly Gly Val Arg Ser Met Pro Ser Leu Leu Ala Cys
1               5                   10                  15

Trp Gln Pro Ile Leu Leu Val Leu Gly Ser Val Leu Ser Gly Ser
                20                  25                  30

Ala Thr Gly Cys Pro Pro Arg Cys Glu Cys Ser Ala Gln Asp Arg Ala
                35                  40                  45

Val Leu Cys His Arg Lys Arg Phe Val Ala Val Pro Glu Gly Ile Pro
50                  55                  60

Thr Glu Thr Arg Leu Leu Asp Leu Gly Lys Asn Arg Ile Lys Thr Leu
65                  70                  75                  80

Asn Gln Asp Glu Phe Ala Ser Phe Pro His Leu Glu Glu Leu Glu Leu
                85                  90                  95

Asn Glu Asn Ile Val Ser Ala Val Glu Pro Gly Ala Phe Asn Asn Leu
                100                 105                 110

Phe Asn Leu Arg Thr Leu Gly Leu Arg Ser Asn Arg Leu Lys Leu Ile
                115                 120                 125

Pro Leu Gly Val Phe Thr Gly Leu Ser Asn Leu Thr Lys Leu Asp Ile
                130                 135                 140

Ser Glu Asn Lys Ile Val Ile Leu Leu Asp Tyr Met Phe Gln Asp Leu
145                 150                 155                 160

Tyr Asn Leu Lys Ser Leu Glu Val Gly Asp Asn Asp Leu Val Tyr Ile
                165                 170                 175

Ser His Arg Ala Phe Ser Gly Leu Asn Ser Leu Glu Gln Leu Thr Leu
                180                 185                 190

Glu Lys Cys Asn Leu Thr Ser Ile Pro Thr Glu Ala Leu Ser His Leu
                195                 200                 205

His Gly Leu Ile Val Leu Arg Leu Arg His Leu Asn Ile Asn Ala Ile
                210                 215                 220

Arg Asp Tyr Ser Phe Lys Arg Leu Tyr Arg Leu Lys Val Leu Glu Ile
225                 230                 235                 240

Ser His Trp Pro Tyr Leu Asp Thr Met Thr Pro Asn Cys Leu Tyr Gly
                245                 250                 255

Leu Asn Leu Thr Ser Leu Ser Ile Thr His Cys Asn Leu Thr Ala Val
                260                 265                 270

Pro Tyr Leu Ala Val Arg His Leu Val Tyr Leu Arg Phe Leu Asn Leu
                275                 280                 285

Ser Tyr Asn Pro Ile Ser Thr Ile Glu Gly Ser Met Leu His Glu Leu
                290                 295                 300

Leu Arg Leu Gln Glu Ile Gln Leu Val Gly Gly Gln Leu Ala Val Val
305                 310                 315                 320
```

-continued

```
Glu Pro Tyr Ala Phe Arg Gly Leu Asn Tyr Leu Arg Val Leu Asn Val
                325                 330                 335

Ser Gly Asn Gln Leu Thr Thr Leu Glu Ser Val Phe His Ser Val
        340                 345                 350

Gly Asn Leu Glu Thr Leu Ile Leu Asp Ser Asn Pro Leu Ala Cys Asp
            355                 360                 365

Cys Arg Leu Leu Trp Val Phe Arg Arg Trp Arg Leu Asn Phe Asn
    370                 375                 380

Arg Gln Gln Pro Thr Cys Ala Thr Pro Glu Phe Val Gln Gly Lys Glu
385                 390                 395                 400

Phe Lys Asp Phe Pro Asp Val Leu Leu Pro Asn Tyr Phe Thr Cys Arg
                405                 410                 415

Arg Ala Arg Ile Arg Asp Arg Lys Ala Gln Gln Val Phe Val Asp Glu
            420                 425                 430

Gly His Thr Val Gln Phe Val Cys Arg Ala Asp Gly Asp Pro Pro
        435                 440                 445

Ala Ile Leu Trp Leu Ser Pro Arg Lys His Leu Val Ser Ala Lys Ser
        450                 455                 460

Asn Gly Arg Leu Thr Val Phe Pro Asp Gly Thr Leu Glu Val Arg Tyr
465                 470                 475                 480

Ala Gln Val Gln Asp Asn Gly Thr Tyr Leu Cys Ile Ala Ala Asn Ala
                485                 490                 495

Gly Gly Asn Asp Ser Met Pro Ala His Leu His Val Arg Ser Tyr Ser
            500                 505                 510

Pro Asp Trp Pro His Gln Pro Asn Lys Thr Phe Ala Phe Ile Ser Asn
        515                 520                 525

Gln Pro Gly Glu Gly Glu Ala Asn Ser Thr Arg Ala Thr Val Pro Phe
530                 535                 540

Pro Phe Asp Ile Lys Thr Leu Ile Ile Ala Thr Thr Met Gly Phe Ile
545                 550                 555                 560

Ser Phe Leu Gly Val Val Leu Phe Cys Leu Val Leu Leu Phe Leu Trp
                565                 570                 575

Ser Arg Gly Lys Gly Asn Thr Lys His Asn Ile Glu Ile Glu Tyr Val
            580                 585                 590

Pro Arg Lys Ser Asp Ala Gly Ile Ser Ser Ala Asp Ala Pro Arg Lys
        595                 600                 605

Phe Asn Met Lys Met Ile
        610

<210> SEQ ID NO 3
<211> LENGTH: 2663
<212> TYPE: DNA
<213> ORGANISM: Homo sapiens

<400> SEQUENCE: 3
tgcagctggg agcgcacaga cggctgcccc gcctgagcga ggcgggcgcc gccgcgatgc     60
tgcgaggcgg acggcgcggg cagcttggct ggcacagctg ggctgcgggg ccgggcagcc    120
tgctggcttg gctgatactg gcatctgcgg gcgccgcacc ctgccccgat gcctgctgcc    180
cccacggctc ctcgggactg cgatgcaccc gggatggggc cctggatagc ctccaccacc    240
tgcccggcgc agagaacctg actgagtctc acatcgagaa ccagcagcat ctgcagcatc    300
tggagctccg tgatctgagg ggcctggggg agctgagaaa cctcaccatc gtgaagagtg    360
gtctccgttt cgtggcgcca gatgccttcc atttcactcc tcggctcagt cgcctgaatc    420
tctccttcaa cgctctggag tctctctcct ggaaaactgt gcagggcctc tccttacagg    480
```

```
aactggtcct gtcggggaac cctctgcact gttcttgtgc cctgcgctgg ctacagcgct    540
gggaggagga gggactgggc ggagtgcctg aacagaagct gcagtgtcat gggcaagggc    600
ccctggccca catgcccaat gccagctgtg gtgtgcccac gctgaaggtc caggtgccca    660
atgcctcggt ggatgtgggg gacgacgtgc tgctgcggtg ccaggtggag gggcggggcc    720
tggagcaggc cggctggatc ctcacagagc tggagcagtc agccacggtg atgaaatctg    780
ggggtctgcc atccctgggg ctgaccctgg ccaatgtcac cagtgacctc aacaggaaga    840
acgtgacgtg ctgggcagag aacgatgtgg gccgggcaga ggtctctgtt caggtcaacg    900
tctccttccc ggccagtgtg cagctgcaca cggcggtgga gatgcaccac tggtgcatcc    960
ccttctctgt ggatgggcag ccggcaccgt ctctgcgctg gctcttcaat ggctccgtgc   1020
tcaatgagac cagcttcatc ttcactgagt tcctggagcc ggcagccaat gagaccgtgc   1080
ggcacgggtg tctgcgcctc aaccagccca cccacgtcaa caacggcaac tacacgctgc   1140
tggctgccaa ccccttcggc caggcctccg cctccatcat ggctgccttc atggacaacc   1200
ctttcgagtt caaccccgag acccccatcc ctgtctcctt ctcgccggtg gacactaaca   1260
gcacatctgg agacccggtg gagaagaagg acgaaacacc ttttggggtc tcggtggctg   1320
tgggcctggc cgtctttgcc tgcctcttcc tttctacgct gctccttgtg ctcaacaaat   1380
gtggacggag aaaacaagttt gggatcaacc gcccggctgt gctggctcca gaggatgggc   1440
tggccatgtc cctgcatttc atgacattgg gtggcagctc cctgtccccc accgagggca   1500
aaggctctgg gctccaaggc cacatcatcg agaacccaca atacttcagt gatgcctgtg   1560
ttcaccacat caagcgccgg gacatcgtgc tcaagtggga gctgggggag ggcgcctttg   1620
ggaaggtctt ccttgctgag tgccacaacc tcctgcctga gcaggacaag atgctggtgg   1680
ctgtcaaggc actgaaggag gcgtccgaga gtgctcggca ggacttccag cgtgaggctg   1740
agctgctcac catgctgcag caccagcaca tcgtgcgctt cttcggcgtc tgcaccgagg   1800 gccgcccct gctcatggtc tttgagtata tgcggcacgg ggacctcaac cgcttcctcc   1860
gatcccatgg acctgatgcc aagctgctgg ctggtgggga ggatgtggct ccaggccccc   1920
tgggtctggg gcagctgctg gccgtggcta gccaggtcgc tgcggggatg gtgtacctgg   1980
cgggtctgca ttttgtgcac cgggacctgg ccacacgcaa ctgtctagtg gccagggac   2040 tggtggtcaa gattggtgat tttggcatga gcagggatat ctacagcacc gactattacc   2100
gtgtgggagg ccgcaccatg ctgcccattc gctggatgcc gcccgagagc atcctgtacc   2160
gtaagttcac caccgagagc gacgtgtgga gcttcggcgt ggtgctctgg gagatcttca   2220
cctacggcaa gcagccctgg taccagctct ccaacacgga ggcaatcgac tgcatcacgc   2280
agggacgtga gttggagcgg ccacgtgcct gcccaccaga ggtctacgcc atcatgcggg   2340
gctgctggca gcgggagccc cagcaacgcc acagcatcaa ggatgtgcac gcccggctgc   2400
aagccctggc ccaggcacct cctgtctacc tggatgtcct gggctagggg gccggcccag   2460
gggctgggag tggttagccg gaatactggg gcctgccctc agcatccccc atagctccca   2520
gcagccccag ggtgatctca aagtatctaa ttcaccctca gcatgtggga agggacaggt   2580
gggggctggg agtagaggat gttcctgctt ctctaggcaa ggtcccgtca tagcaattat   2640
atttattatc ccttgaaaaa aaa                                            2663
```

<210> SEQ ID NO 4
<211> LENGTH: 796
<212> TYPE: PRT
<213> ORGANISM: Homo sapiens

<400> SEQUENCE: 4

```
Met Leu Arg Gly Gly Arg Gly Gln Leu Gly Trp His Ser Trp Ala
1               5                   10                  15

Ala Gly Pro Gly Ser Leu Leu Ala Trp Leu Ile Leu Ala Ser Ala Gly
            20                  25                  30

Ala Ala Pro Cys Pro Asp Ala Cys Cys Pro His Gly Ser Ser Gly Leu
        35                  40                  45

Arg Cys Thr Arg Asp Gly Ala Leu Asp Ser Leu His His Leu Pro Gly
    50                  55                  60

Ala Glu Asn Leu Thr Glu Leu Tyr Ile Glu Asn Gln Gln His Leu Gln
65                  70                  75                  80

His Leu Glu Leu Arg Asp Leu Arg Gly Leu Gly Glu Leu Arg Asn Leu
                85                  90                  95

Thr Ile Val Lys Ser Gly Leu Arg Phe Val Ala Pro Asp Ala Phe His
            100                 105                 110

Phe Thr Pro Arg Leu Ser Arg Leu Asn Leu Ser Phe Asn Ala Leu Glu
        115                 120                 125

Ser Leu Ser Trp Lys Thr Val Gln Gly Leu Ser Leu Gln Glu Leu Val
    130                 135                 140

Leu Ser Gly Asn Pro Leu His Cys Ser Cys Ala Leu Arg Trp Leu Gln
145                 150                 155                 160

Arg Trp Glu Glu Glu Gly Leu Gly Gly Val Pro Glu Gln Lys Leu Gln
                165                 170                 175

Cys His Gly Gln Gly Pro Leu Ala His Met Pro Asn Ala Ser Cys Gly
            180                 185                 190

Val Pro Thr Leu Lys Val Gln Val Pro Asn Ala Ser Val Asp Val Gly
        195                 200                 205

Asp Asp Val Leu Leu Arg Cys Gln Val Glu Gly Arg Gly Leu Glu Gln
    210                 215                 220

Ala Gly Trp Ile Leu Thr Glu Leu Glu Gln Ser Ala Thr Val Met Lys
225                 230                 235                 240

Ser Gly Gly Leu Pro Ser Leu Gly Leu Thr Leu Ala Asn Val Thr Ser
                245                 250                 255

Asp Leu Asn Arg Lys Asn Val Thr Cys Trp Ala Glu Asn Asp Val Gly
            260                 265                 270

Arg Ala Glu Val Ser Val Gln Val Asn Val Ser Phe Pro Ala Ser Val
        275                 280                 285

Gln Leu His Thr Ala Val Glu Met His His Trp Cys Ile Pro Phe Ser
    290                 295                 300

Val Asp Gly Gln Pro Ala Pro Ser Leu Arg Trp Leu Phe Asn Gly Ser
305                 310                 315                 320

Val Leu Asn Glu Thr Ser Phe Ile Phe Thr Glu Phe Leu Glu Pro Ala
                325                 330                 335

Ala Asn Glu Thr Val Arg His Gly Cys Leu Arg Leu Asn Gln Pro Thr
            340                 345                 350

His Val Asn Asn Gly Asn Tyr Thr Leu Leu Ala Ala Asn Pro Phe Gly
        355                 360                 365

Gln Ala Ser Ala Ser Ile Met Ala Ala Phe Met Asp Asn Pro Phe Glu
    370                 375                 380

Phe Asn Pro Glu Asp Pro Ile Pro Val Ser Phe Ser Pro Val Asp Thr
385                 390                 395                 400

Asn Ser Thr Ser Gly Asp Pro Val Glu Lys Lys Asp Glu Thr Pro Phe
                405                 410                 415
```

Gly Val Ser Val Ala Val Gly Leu Ala Val Phe Ala Cys Leu Phe Leu
            420                 425                 430

Ser Thr Leu Leu Leu Val Leu Asn Lys Cys Gly Arg Arg Asn Lys Phe
        435                 440                 445

Gly Ile Asn Arg Pro Ala Val Leu Ala Pro Glu Asp Gly Leu Ala Met
450                 455                 460

Ser Leu His Phe Met Thr Leu Gly Gly Ser Ser Leu Ser Pro Thr Glu
465                 470                 475                 480

Gly Lys Gly Ser Gly Leu Gln Gly His Ile Ile Glu Asn Pro Gln Tyr
                485                 490                 495

Phe Ser Asp Ala Cys Val His His Ile Lys Arg Arg Asp Ile Val Leu
            500                 505                 510

Lys Trp Glu Leu Gly Glu Gly Ala Phe Gly Lys Val Phe Leu Ala Glu
        515                 520                 525

Cys His Asn Leu Leu Pro Glu Gln Asp Lys Met Leu Val Ala Val Lys
530                 535                 540

Ala Leu Lys Glu Ala Ser Glu Ser Ala Arg Gln Asp Phe Gln Arg Glu
545                 550                 555                 560

Ala Glu Leu Leu Thr Met Leu Gln His Gln His Ile Val Arg Phe Phe
                565                 570                 575

Gly Val Cys Thr Glu Gly Arg Pro Leu Leu Met Val Phe Glu Tyr Met
            580                 585                 590

Arg His Gly Asp Leu Asn Arg Phe Leu Arg Ser His Gly Pro Asp Ala
        595                 600                 605

Lys Leu Leu Ala Gly Gly Glu Asp Val Ala Pro Gly Pro Leu Gly Leu
610                 615                 620

Gly Gln Leu Leu Ala Val Ala Ser Gln Val Ala Ala Gly Met Val Tyr
625                 630                 635                 640

Leu Ala Gly Leu His Phe Val His Arg Asp Leu Ala Thr Arg Asn Cys
                645                 650                 655

Leu Val Gly Gln Gly Leu Val Val Lys Ile Gly Asp Phe Gly Met Ser
            660                 665                 670

Arg Asp Ile Tyr Ser Thr Asp Tyr Tyr Arg Val Gly Gly Arg Thr Met
        675                 680                 685

Leu Pro Ile Arg Trp Met Pro Pro Glu Ser Ile Leu Tyr Arg Lys Phe
690                 695                 700

Thr Thr Glu Ser Asp Val Trp Ser Phe Gly Val Val Leu Trp Glu Ile
705                 710                 715                 720

Phe Thr Tyr Gly Lys Gln Pro Trp Tyr Gln Leu Ser Asn Thr Glu Ala
                725                 730                 735

Ile Asp Cys Ile Thr Gln Gly Arg Glu Leu Glu Arg Pro Arg Ala Cys
            740                 745                 750

Pro Pro Glu Val Tyr Ala Ile Met Arg Gly Cys Trp Gln Arg Glu Pro
        755                 760                 765

Gln Gln Arg His Ser Ile Lys Asp Val His Ala Arg Leu Gln Ala Leu
770                 775                 780

Ala Gln Ala Pro Pro Val Tyr Leu Asp Val Leu Gly
785                 790                 795

<210> SEQ ID NO 5
<211> LENGTH: 2633
<212> TYPE: DNA
<213> ORGANISM: Rattus sp.

<400> SEQUENCE: 5

-continued

```
gcggcggcgg ccaggagcgc acggacggcc gcgcggcccg agctaggcgg gcgccgccgc    60
gatgctgcga ggccagcggc acgggcagct gggttggcat cgcccggccg cggggctagg   120
cggtctggtg acttcgttga tgctggcttg tgcttgcgcc gcatcctgtc gtgagacctg   180
ctgtcccgtg ggcccctcgg ggttgcgctg caccagggca gggaccctga atacccctccg  240
cggcctgcgg ggcgccggga acctgacgga gctctatgtg gaaaaccagc gggatctgca   300
acgcctggag tttgaggacc tgcagggcct gggggagttg agaagcctaa ccatcgtgaa   360
gagtggcctc cgctttgtgg ccctgatgc cttccatttc accctcggc tcagtcacct     420
gaatctctcc tccaatgctt tggagtccct ctcctggaaa actgtgcagg gcctctccct   480
acaggacttg accctgtcag ggaacccact gcactgttcc tgtgccctat tgtggctcca   540
gcgctgggag caggaggatt tgtgtggtgt gtatacacaa aagcttcagg gctctgggtc   600
tggagaccag ttcctcccac tgggacacaa caacagttgt ggtgtaccct cagtgaagat   660
ccagatgccc aatgactctg tggaagtggg ggatgacgtt tttctgcagt gccaggtgga   720
ggggcaggcc ctacagcagg ctgactggat cctcacagag ctggaaggga cagccaccat   780
gaagaaatct ggagatctgc catccctggg gctaactctg gtcaatgtca ccagtgatct   840
caacaagaag aatgtgacgt gctgggcaga gaatgatgtg ggccgggctg aggtctctgt   900
ccaagtcagc gtctccttcc cagccagtgt gcatctgggc aaagccgtgg aacagcatca   960
ctggtgcatt cccttctctg tggacgggca gccagcaccg tccctgcgct ggttcttcaa  1020
cggctctgtg ctcaatgaga ccagcttcat cttcactcag ttcttggagt cagcgctgac  1080
caatgagacc atgcggcatg gctgccttcg cctcaaccag cccacgcatg tcaacaacgg  1140
gaactacacc ctgctggctg ccaaccccta tggccaggct gctgcctcca tcatggctgc  1200
ctttatggac aacccttttg agttcaaccc tgaggacccc atccctgtct ccttctcgcc  1260
agtggacact aacagcacat caagagaccc agtggagaag aaggacgaaa cacccttttgg  1320
ggtctctgtg gctgtgggcc tggccgtctc cgccgccctc ttcctttctg ccctcctcct  1380
agtgctcaac aaatgtggac agaggagcaa atttgggatc aaccgccctg ctgtgctggc  1440
gccagaggat gggctggcca tgtccctaca cttcatgaca ctgggtggca gttctctttc  1500
ccctactgag ggcaaaggct ccggactcca gggccacatc atggagaacc cacagtactt  1560
cagtgatacc tgtgtccacc atatcaagcg ccaggacatc attctcaagt gggagctagg  1620
ggagggagcc tttggaaagg tctttcttgc tgagtgctac aaccttctga atgatcagga  1680
caagatgctg gtggctgtca aggcactgaa ggagacatct gagaatgctc gtcaggactt  1740
ccatcgtgag gcagagctgc tcaccatgct acagcaccaa cacatcgtac gcttctttgg  1800
agtctgcacg gagggtggcc cattgctcat ggtcttcgag tacatgcgcc atgggacct   1860
caaccgtttc ctccggtccc acggacctga tgcaaaactg ctggctggcg gcgaggatgt  1920
ggctcctggt cctttgggcc ttgggcagct tctggctgtg gctagccagg tggctgctgg  1980
tatggtgtac ctagccagcc tgcactttgt gcaccgggac ctggccacac gcaactgtct  2040
ggtgggtcag ggactagtgg tcaagattgg agacttcggc atgagcaggg acatctacag  2100
cacagactac taccgtgtgg aggtcggac catgctgccc atccgctgga tgcctccaga  2160
gagcatcctc taccgcaagt tcagcaccga gagtgatgtg tggagcttcg gggtggtgct  2220
ctgggagatc ttcacctatg gaaagcaacc ctggtaccag ctctccaaca ctgaggcgat  2280
cgagtgcatc acgcagggcc gggagctgga gcggccgcgc cctgccctc ctgatgtcta   2340
cgccatcatg cgcggctgct ggcagcgtga gccgcaacag cgcctcagca tgaaggatgt  2400
```

```
gcacgcgcgg ctgcaggcct tggcacaggc gccaccgagt tacctggacg ttctgggcta    2460
ggagtctgga tgtcaggcta ccctgggctc cctcagcgcc cagcagctat cacactcaag    2520
tcttaccctc agcatgtgga ggggaccagc aggcggggag cagagggtgg ctttgcttca    2580
tggccagcat ccatcataat agcaattata tttattatcc ctgaaaaaaa aaa           2633

<210> SEQ ID NO 6
<211> LENGTH: 799
<212> TYPE: PRT
<213> ORGANISM: Rattus sp.

<400> SEQUENCE: 6

Met Leu Arg Gly Gln Arg His Gly Gln Leu Gly Trp His Arg Pro Ala
1               5                   10                  15

Ala Gly Leu Gly Gly Leu Val Thr Ser Leu Met Leu Ala Cys Ala Cys
            20                  25                  30

Ala Ala Ser Cys Arg Glu Thr Cys Cys Pro Val Gly Pro Ser Gly Leu
        35                  40                  45

Arg Cys Thr Arg Ala Gly Thr Leu Asn Thr Leu Arg Gly Leu Arg Gly
    50                  55                  60

Ala Gly Asn Leu Thr Glu Leu Tyr Val Glu Asn Gln Arg Asp Leu Gln
65                  70                  75                  80

Arg Leu Glu Phe Glu Asp Leu Gln Gly Leu Gly Glu Leu Arg Ser Leu
                85                  90                  95

Thr Ile Val Lys Ser Gly Leu Arg Phe Val Ala Pro Asp Ala Phe His
            100                 105                 110

Phe Thr Pro Arg Leu Ser His Leu Asn Leu Ser Ser Asn Ala Leu Glu
        115                 120                 125

Ser Leu Ser Trp Lys Thr Val Gln Gly Leu Ser Leu Gln Asp Leu Thr
    130                 135                 140

Leu Ser Gly Asn Pro Leu His Cys Ser Cys Ala Leu Leu Trp Leu Gln
145                 150                 155                 160

Arg Trp Glu Gln Glu Asp Leu Cys Gly Val Tyr Thr Gln Lys Leu Gln
                165                 170                 175

Gly Ser Gly Ser Gly Asp Gln Phe Leu Pro Leu Gly His Asn Asn Ser
            180                 185                 190

Cys Gly Val Pro Ser Val Lys Ile Gln Met Pro Asn Asp Ser Val Glu
        195                 200                 205

Val Gly Asp Asp Val Phe Leu Gln Cys Gln Val Glu Gly Gln Ala Leu
    210                 215                 220

Gln Gln Ala Asp Trp Ile Leu Thr Glu Leu Glu Gly Thr Ala Thr Met
225                 230                 235                 240

Lys Lys Ser Gly Asp Leu Pro Ser Leu Gly Leu Thr Leu Val Asn Val
                245                 250                 255

Thr Ser Asp Leu Asn Lys Lys Asn Val Thr Cys Trp Ala Glu Asn Asp
            260                 265                 270

Val Gly Arg Ala Glu Val Ser Val Gln Val Ser Val Ser Phe Pro Ala
        275                 280                 285

Ser Val His Leu Gly Lys Ala Val Glu Gln His His Trp Cys Ile Pro
    290                 295                 300

Phe Ser Val Asp Gly Gln Pro Ala Pro Ser Leu Arg Trp Phe Phe Asn
305                 310                 315                 320

Gly Ser Val Leu Asn Glu Thr Ser Phe Ile Phe Thr Gln Phe Leu Glu
                325                 330                 335
```

```
Ser Ala Leu Thr Asn Glu Thr Met Arg His Gly Cys Leu Arg Leu Asn
        340                 345                 350

Gln Pro Thr His Val Asn Asn Gly Asn Tyr Thr Leu Leu Ala Ala Asn
        355                 360                 365

Pro Tyr Gly Gln Ala Ala Ser Ile Met Ala Phe Met Asp Asn
        370                 375                 380

Pro Phe Glu Phe Asn Pro Glu Asp Pro Ile Pro Val Ser Phe Ser Pro
385                 390                 395                 400

Val Asp Thr Asn Ser Thr Ser Arg Asp Pro Val Glu Lys Lys Asp Glu
                405                 410                 415

Thr Pro Phe Gly Val Ser Val Ala Val Gly Leu Ala Val Ser Ala Ala
            420                 425                 430

Leu Phe Leu Ser Ala Leu Leu Leu Val Leu Asn Lys Cys Gly Gln Arg
        435                 440                 445

Ser Lys Phe Gly Ile Asn Arg Pro Ala Val Leu Ala Pro Glu Asp Gly
        450                 455                 460

Leu Ala Met Ser Leu His Phe Met Thr Leu Gly Gly Ser Ser Leu Ser
465                 470                 475                 480

Pro Thr Glu Gly Lys Gly Ser Gly Leu Gln Gly His Ile Met Glu Asn
                485                 490                 495

Pro Gln Tyr Phe Ser Asp Thr Cys Val His His Ile Lys Arg Gln Asp
            500                 505                 510

Ile Ile Leu Lys Trp Glu Leu Gly Glu Gly Ala Phe Gly Lys Val Phe
        515                 520                 525

Leu Ala Glu Cys Tyr Asn Leu Leu Asn Asp Gln Asp Lys Met Leu Val
        530                 535                 540

Ala Val Lys Ala Leu Lys Glu Thr Ser Glu Asn Ala Arg Gln Asp Phe
545                 550                 555                 560

His Arg Glu Ala Glu Leu Leu Thr Met Leu Gln His Gln His Ile Val
                565                 570                 575

Arg Phe Phe Gly Val Cys Thr Glu Gly Gly Pro Leu Leu Met Val Phe
            580                 585                 590

Glu Tyr Met Arg His Gly Asp Leu Asn Arg Phe Leu Arg Ser His Gly
        595                 600                 605

Pro Asp Ala Lys Leu Leu Ala Gly Gly Glu Asp Val Ala Pro Gly Pro
610                 615                 620

Leu Gly Leu Gly Gln Leu Leu Ala Val Ala Ser Gln Val Ala Ala Gly
625                 630                 635                 640

Met Val Tyr Leu Ala Ser Leu His Phe Val His Arg Asp Leu Ala Thr
                645                 650                 655

Arg Asn Cys Leu Val Gly Gln Gly Leu Val Val Lys Ile Gly Asp Phe
            660                 665                 670

Gly Met Ser Arg Asp Ile Tyr Ser Thr Asp Tyr Tyr Arg Val Gly Gly
        675                 680                 685

Arg Thr Met Leu Pro Ile Arg Trp Met Pro Pro Glu Ser Ile Leu Tyr
        690                 695                 700

Arg Lys Phe Ser Thr Glu Ser Asp Val Trp Ser Phe Gly Val Val Leu
705                 710                 715                 720

Trp Glu Ile Phe Thr Tyr Gly Lys Gln Pro Trp Tyr Gln Leu Ser Asn
                725                 730                 735

Thr Glu Ala Ile Glu Cys Ile Thr Gln Gly Arg Glu Leu Glu Arg Pro
            740                 745                 750

Arg Ala Cys Pro Pro Asp Val Tyr Ala Ile Met Arg Gly Cys Trp Gln
        755                 760                 765
```

Arg Glu Pro Gln Gln Arg Leu Ser Met Lys Asp Val His Ala Arg Leu
        770                 775                 780

Gln Ala Leu Ala Gln Ala Pro Pro Ser Tyr Leu Asp Val Leu Gly
785                 790                 795

<210> SEQ ID NO 7
<211> LENGTH: 6
<212> TYPE: PRT
<213> ORGANISM: Homo sapiens

<400> SEQUENCE: 7

Met Gln Val Ser Lys Arg
1               5

<210> SEQ ID NO 8
<211> LENGTH: 17
<212> TYPE: DNA
<213> ORGANISM: Artificial Sequence
<220> FEATURE:
<223> OTHER INFORMATION: siRNA forward oligonucleotide
<220> FEATURE:
<221> NAME/KEY: misc_feature
<222> LOCATION: (1)..(17)
<223> OTHER INFORMATION: n is A, T, G, C or U

<400> SEQUENCE: 8
nnnnnnnnnn nnnnnnn                                                17

<210> SEQ ID NO 9
<211> LENGTH: 17
<212> TYPE: DNA
<213> ORGANISM: Artificial Sequence
<220> FEATURE:
<223> OTHER INFORMATION: siRNA reverse oligonucleotde
<220> FEATURE:
<221> NAME/KEY: misc_feature
<222> LOCATION: (1)..(17)
<223> OTHER INFORMATION: n is A, T, G, C or U

<400> SEQUENCE: 9
nnnnnnnnnn nnnnnnn                                                17

<210> SEQ ID NO 10
<211> LENGTH: 19
<212> TYPE: DNA
<213> ORGANISM: Artificial sequence
<220> FEATURE:
<223> OTHER INFORMATION: Sp35 forward primer

<400> SEQUENCE: 10
agagacatgc gattggtga                                              19

<210> SEQ ID NO 11
<211> LENGTH: 21
<212> TYPE: DNA
<213> ORGANISM: Artificial sequence
<220> FEATURE:
<223> OTHER INFORMATION: Sp35 reverse primer

<400> SEQUENCE: 11
agagatgtag acgaggtcat t                                           21

<210> SEQ ID NO 12
<211> LENGTH: 19
<212> TYPE: DNA
<213> ORGANISM: Artificial sequence
<220> FEATURE:

```
<223> OTHER INFORMATION: TrkA forward primer

<400> SEQUENCE: 12
tgacttcgtt gatgctggc                                                19

<210> SEQ ID NO 13
<211> LENGTH: 21
<212> TYPE: DNA
<213> ORGANISM: Artificial sequence
<220> FEATURE:
<223> OTHER INFORMATION: TrkA reverse primer

<400> SEQUENCE: 13
ctgtagggcc tgcccctcca c                                             21

<210> SEQ ID NO 14
<211> LENGTH: 55
<212> TYPE: RNA
<213> ORGANISM: Artificial sequence
<220> FEATURE:
<223> OTHER INFORMATION: Small-hairpin RNA (shRNA)

<400> SEQUENCE: 14
ugaucgucau ccugcuagac uucaagagag ucuagcagga ugacgaucuu uuuuc         55

<210> SEQ ID NO 15
<211> LENGTH: 6
<212> TYPE: PRT
<213> ORGANISM: Artificial Sequence
<220> FEATURE:
<223> OTHER INFORMATION: extracellular domain

<400> SEQUENCE: 15

Val Ser Phe Ser Pro Val
1               5
```

METHODS FOR PROMOTING MYELINATION, NEURONAL SURVIVAL AND OLIGODENDROCYTE DIFFERENTIATION VIA ADMINISTRATION OF SP35 OR TRKA ANTAGONISTS

CROSS-REFERENCE TO RELATED APPLICATIONS

The present application is the National Stage of International Application No. PCT/US2007/016589, filed Jul. 24, 2007, which claims the benefit of U.S. Provisional Application No. 60/836,652, filed Aug. 10, 2006 and U.S. Provisional Application No. 60/832,586, filed Jul. 24, 2006, all of which are incorporated herein by reference in their entireties.

REFERENCE TO SEQUENCE LISTING SUBMITTED ELECTRONICALLY VIA EFS-WEB

The content of the electronically submitted Substitute Sequence Listing (Name: 21591050002 SubstituteSequenceListing.ascii.txt; Size: 30,872 bytes; and Date of Creation: Jun. 17, 2013) is herein incorporated by reference in its entirety.

BACKGROUND OF THE INVENTION

1. Field of the Invention

This invention relates to neurology, neurobiology and molecular biology. More particularly, this invention relates to methods for promoting myelination and increased neuronal survival and treating demyelination and dysmyelination disease by the administration of a TrkA antagonist. The invention also relates to methods of inhibiting or decreasing Sp35 expression by the use of a TrkA antagonist. Additionally, the invention relates generally to methods for blocking Sp35 and TrkA and inhibiting or decreasing TrkA phosphorylation by the administration of a Sp35 antagonist.

2. Background Art

Nerve cell function is influenced by contact between neurons and other cells in their immediate environment (Rutishauser, et al., 1988, Physiol. Rev. 68:819). These cells include specialized glial cells, oligodendrocytes in the central nervous system (CNS), and Schwann cells in the peripheral nervous system (PNS), which sheathe the neuronal axon with myelin (Lemke, 1992, in *An Introduction to Molecular Neurobiology*, Z. Hall, Ed., p. 281, Sinauer).

The formation of the myelin sheath is an exquisite and dynamic example of cell-cell interaction that involves the myelin-forming cell and the neuronal axon. It is generally thought that during development axons control whether they will become myelinated by expressing appropriate signals to either promote or inhibit this process (Colello and Pott, *Mol. Neurobiol.* 15:83-100 (1997)).

CNS neurons have the inherent potential to regenerate after injury, but they are inhibited from doing so by inhibitory proteins present in myelin (Brittis et al., 2001, Neuron 30:11-14; Jones et al, 2002, J. Neurosci. 22:2792-2803; Grimpe et al, 2002, J. Neurosci.:22:3144-3160).

Several myelin inhibitory proteins found on oligodendrocytes have been characterized. Known examples of myelin inhibitory proteins include NogoA (Chen et al., Nature, 2000, 403, 434-439; Grandpre et al., Nature 2000, 403, 439-444), myelin associated glycoprotein (MAG) (McKerracher et al., 1994, Neuron 13:805-811; Mukhopadhyay et al., 1994, Neuron 13:757-767) and oligodendrocyte glycoprotein (OM-gp), Mikol et al., 1988, J. Cell. Biol. 106:1273-1279). Each of these proteins has been separately shown to be a ligand for the neuronal Nogo receptor-1 (NgR1) (Wang et al., Nature 2002, 417, 941-944; Grandpre et al., Nature 2000, 403, 439-444; Chen et al., Nature, 2000, 403, 434-439; Domeniconi et al., Neuron 2002, published online Jun. 28, 2002).

Recent studies of Nerve Growth Factor (NGF), and its receptor TrkA, suggest that different axonal signals control central and peripheral myelination. Indeed, as was previously reported, NGF has opposite effects on Schwann Cells (SC) and oligodendrocyte myelination (Chan et al., *Neuron* 43:183-91 (2004)).

Many diseases of the nervous system are associated with demyelination and dysmyelination, including multiple sclerosis (MS), progressive multi focal leukoencephalopathy (PML), encephalomyelitis (EPL), central pontine myelolysis (CPM), Wallerian Degeneration and some inherited diseases such as adrenoleukodystrophy, Alexander's disease, and Pelizaeus Merzbacher disease (PMZ). Among these diseases, MS is the most widespread, affecting approximately 2.5 million people worldwide.

MS generally begins with a relapsing-remitting pattern of neurological involvement, which then progresses to a chronic phase with increasing neurological damage. MS is associated with the destruction of myelin, oligodendrocytes and axons localized to chronic lesions. The demyelination observed in MS is not always permanent and remyelination has been documented in early stages of the disease. Remyelination of neurons requires oligodendrocytes.

Various disease-modifying treatments are available for MS, including the use of corticosteroids and immunomodulators such as interferon beta. In addition, because of the central role of oligodendrocytes and myelination in MS, there have been efforts to develop therapies to increase oligodendrocyte numbers or enhance myelination. See, e.g., Cohen et al., U.S. Pat. No. 5,574,009; Chang et al., *N. Engl. J. Med.* 346:165-73 (2002).

The use of Sp35 antagonists to promote myelination and oligodendrocyte and neuronal survival has been described, for example, in U.S. Published Application No. 2006/0009388 A1 and Mi et al., *Nat. Neurosci.* 7:221-228 (2004), both of which are herein incorporated by reference in their entireties. However, there remains an urgent need to devise additional therapies for MS.

BRIEF SUMMARY OF THE INVENTION

The present invention is based on the discovery that Sp35 is co-expressed and interacts with TrkA in central nervous system (CNS) neurons. Specifically, NGF, through its cognate receptor TrkA, induces Sp35 expression and inhibition of axonal myelination and oligodendrocyte differentiation via Sp35 function. While Sp35 expressed by oligodendrocytes was previously identified as an inhibitor of differentiation (Mi et al., *Nat. Neurosci.* 8:745-51 (2005)), axonal expression of Sp35 inhibits oligodendrocyte differentiation with equal potency. Inhibition of Sp35 on either cell type is sufficient to promote differentiation and myelination.

Based on these discoveries, the invention relates generally to promoting myelination and treating a disease, disorder or injury relating to dysmyelination or demyelination by administration of a TrkA antagonist. The invention also relates generally to methods of promoting CNS neuronal survival by the administration of a TrkA antagonist. Additionally, the invention relates generally to methods of inhibiting or decreasing Sp35 expression by administration of a TrkA antagonist. The invention also generally relates to methods of blocking Sp35-TrkA interaction and inhibiting or decreasing TrkA phosphorylation by the administration of an Sp35 antagonist.

In certain embodiments, the invention includes a method for promoting myelination of central nervous system (CNS) neurons in a mammal, comprising contacting a mixture of CNS neurons and oligodendrocytes with a composition comprising a TrkA antagonist. In other embodiments, the method is for promoting myelination comprising administering to a mammal, in need thereof, an effective amount of a composition comprising a TrkA antagonist.

In certain embodiments, the invention includes methods for promoting oligodendrocyte differentiation comprising contacting oligodendrocytes or oligodendrocyte progenitor cells with a TrkA antagonist. Additional methods of the invention include methods for promoting oligodendrocyte differentiation comprising administering to a mammal in need thereof an effective amount of a composition comprising a TrkA antagonist.

In certain embodiments, the invention includes a method for inhibiting or decreasing Sp35 expression in central nervous system (CNS) neurons in a mammal, comprising contacting CNS neurons with a composition comprising a TrkA antagonist.

In additional embodiments, the mammal has been diagnosed with a disease, disorder, injury associated with demyelination or dysmyelination. In some embodiments, the disease, disorder or injury is selected from the group consisting of multiple sclerosis (MS), progressive multifocal leukoencephalopathy (PML), encephalomyelitis (EPL), central pontine myelolysis (CPM), adrenoleukodystrophy, Alexander's disease, Pelizaeus Merzbacher disease (PMZ), Wallerian Degeneration, optic neuritis, transverse myelitis, amylotrophic lateral sclerosis (ALS), Huntington's disease, Alzheimer's disease, Parkinson's disease, spinal cord injury, traumatic brain injury, post radiation injury, neurologic complications of chemotherapy, stroke, acute ischemic optic neuropathy, vitamin E deficiency, isolated vitamin E deficiency syndrome, AR, Bassen-Kornzweig syndrome, Marchiafava-Bignami syndrome, metachromatic leukodystrophy, trigeminal neuralgia, acute dissmeminated encephalitis, Guillian-Barre syndrome, Marie-Charcot-Tooth disease and Bell's palsy.

In various embodiments of the above methods, the TrkA antagonist may be any molecule which interferes with the ability of TrkA to negatively regulate CNS myelination and/or neuronal survival and/or inhibiting or decreasing Sp35 expression. In certain embodiments, the TrkA antagonist is selected from the group consisting of a TrkA antagonist compound, a TrkA antagonist polypeptide, a TrkA antagonist antibody or fragment thereof, a TrkA antagonist polynucleotide (e.g. RNA interference), a TrkA aptamer, or a combination of two or more TrkA antagonists.

In certain embodiments, the TrkA antagonist is a TrkA antagonist compound. Certain TrkA antagonist compounds of the invention include, but are not limited to, K252a and derivatives there of as described in U.S. Pat. No. 5,468,872, which is incorporated herein by reference in its entirety; lidocaine; bupivacaine; procaine; 1H-[1,2,4]oxadiazolo[4,3-□]quinoxalin-1-one (ODQ); methylmercury; endocannabanoid anandamide; CEP-701; CEP-751; PD098059; Tamoxifen; Tunicamycin; 3-morpholinosyndnomine (Sin-1); Tryphostin AG879; herbimycin A; genistein; 5-azacytidine; and tryphostin RG508964.

In certain embodiments, the TrkA antagonist is a TrkA antagonist polypeptide. Certain TrkA antagonist polypeptides of the invention include, but are not limited to, PTEN; SHP-1; pregnancy zone protein; human alpha (2)-macroglobulin (alpha 2M); methylamine-activated alpha 2M (MA-alpha 2M); seratonin-activated alpha 2M (5HT-alpha 2M); Pertussis toxin; the protein produced by the myc myelocytomatesis viral related oncogene (MYCN); and Caveolin. In certain embodiments, the TrkA antagonist polypeptide is a soluble peptide of SEQ ID NO:4. In other embodiments, the TrkA antagonist polypeptide comprises amino acids 1 to 441 of SEQ ID NO:4. In some embodiments, the TrkA antagonist is a fusion polypeptide comprising a non-TrkA moiety. In some embodiments, the non-TrkA moiety is selected from the group consisting of an antibody Ig moiety, a serum albumin moiety, a targeting moiety, a reporter moiety, and a purification-facilitating moiety. In some embodiments, the antibody Ig moiety is a hinge and Fc moiety.

In alternative embodiments, the TrkA antagonist is an antibody or fragment thereof which binds to a TrkA polypeptide. TrkA antagonist antibodies for use in the methods of the present invention include, but are not limited to, MC192, MNAC13 monoclonal antibody and the Fab fragment of AB1577 (Chemicon).

In other embodiments, the TrkA antagonist is TrkA antagonist polynucleotide such as an antisense polynucleotide, an aptamer, a ribozyme, a small interfering RNA (siRNA), or a small-hairpin RNA (shRNA).

In additional embodiments, the TrkA antagonist is a TrkA aptamer. A TrkA aptamer is a small polypeptide or a polynucleotide which binds TrkA and interferes with the ability of TrkA to negatively regulate CNS myelination and/or neuronal survival and/or inhibit or decrease Sp35 expression.

In other embodiments of the above methods, the TrkA antagonist is administered by a method comprising (a) introducing into CNS neurons a polynucleotide which encodes a TrkA antagonist through operable linkage to an expression control sequence; and (b) allowing expression of said TrkA antagonist. In some embodiments the CNS neurons are in a mammal and said introducing comprises (a) administering to said mammal a polynucleotide which encodes a TrkA antagonist through operable linkage to an expression control sequence. In some embodiments, the cultured host cell is derived from the mammal to be treated. In certain embodiments, the polynucleotide is introduced into the host cell or CNS neuron via transfection, electroporation, viral transduction or direct microinjection.

In additional embodiments the polynucleotide encoding the TrkA antagonist is administered to a mammal, at or near the site of the disease, disorder or injury. In some embodiments, the polynucleotide is administered as an expression vector. In certain embodiments, the vector is a viral vector which is selected from the group consisting of an adenoviral vector, an alphavirus vector, an enterovirus vector, a pestivirus vector, a lentiviral vector, a baculoviral vector, a herpesvirus vector, an Epstein Barr viral vector, a papovaviral vector, a poxvirus vector, a vaccinia viral vector, a parvovirus, and a herpes simplex viral vector. In some embodiments, the vector is administered by a route selected from the group consisting of topical administration, intraocular administration, parenteral administration, intrathecal administration, subdural administration and subcutaneous administration.

Additional methods of the present invention include methods for blocking Sp35 and TrkA interaction comprising contacting a mixture of CNS neurons and oligodendrocytes with a composition comprising an Sp35 antagonist. Other embodiments of the invention include methods for inhibiting or decreasing TrkA phosphorylation comprising contacting CNS neurons with a composition comprising an Sp35 antagonist.

In various embodiments of the above methods, the Sp35 antagonist may be any molecule which interferes with the ability of Sp35 to negatively regulate myelination and/or neuronal survival and/or blocking Sp35 and TrkA interaction and/or inhibiting or decreasing TrkA phosphorylation. In certain embodiments, the Sp35 antagonist is selected from the group consisting of a soluble Sp35 polypeptide, an Sp35 antibody or fragment thereof, an Sp35 antagonist polynucleotide (e.g. RNA interference), an Sp35 aptamer, or a combination of two or more Sp35 antagonists.

In certain embodiments, the Sp35 antagonist is a soluble Sp35 polypeptide. Certain soluble Sp35 polypeptides of the invention include, but are not limited to, soluble Sp35 polypeptides which comprise or lack one or more of the following domains: (i) an Sp35 Leucine-Rich Repeat (LRR) domain, (ii) an Sp35 basic region C-terminal to the LRR domain, and (iii) an Sp35 immunoglobulin (Ig) domain. In some embodiments, the soluble Sp35 polypeptide lacks an Sp35 Ig domain, an Sp35 LRR domain, a transmembrane domain, and a cytoplasmic domain. Additional Sp35 soluble polypeptides of the invention include polypeptides which lack a transmembrane domain and a cytoplasmic domain. In some embodiments, the soluble Sp35 polypeptide comprises an Sp35 LRR domain and lacks an Sp35 Ig domain, an Sp35 basic region, a transmembrane domain, and a cytoplasmic domain. In some embodiments, the soluble Sp35 polypeptide comprises amino acid residues 34-532 of SEQ ID NO: 2 or 36-532 of SEQ ID NO:2.

In some embodiments, the Sp35 antagonist is a fusion polypeptide comprising a non-Sp35 moiety. In some embodiments, the non-Sp35 moiety is selected from the group consisting of an antibody Ig moiety, a serum albumin moiety, a targeting moiety, a reporter moiety, and a purification-facilitating moiety. In some embodiments, the antibody Ig moiety is a hinge and Fc moiety.

In alternative embodiments, the Sp35 antagonist is an antibody or fragment thereof which binds to an Sp35 polypeptide comprising one or more of the following Sp35 domains: (i) an Sp35 Leucine-Rich Repeat (LRR) domain, (ii) an Sp35 basic region C-terminal to the LRR domain, and (iii) an Sp35 immunoglobulin (Ig) domain. Additionally, the Sp35 antibody or fragment thereof specifically binds to an epitope within a polypeptide comprising an Sp35 polypeptide fragment as described herein. In additional embodiments, the Sp35 antibody or fragment thereof is selected from the group consisting of 201', 3A3, 3A6, 3B5, 1A7, 1D5, 1G7, 2B10, 2C11, 2F3, 3P1B1.1F9, 3P1D10.2C3, 3P1E11.3B7, 3P2C6.3G10.2H7, 3P2C9.2G4, 3P4A6.1D9, 3P4A1.2B9, 3P4C2.2D2, 3P4C5.1D8, 3P4C8.2G9, 6P4F4.1Ds, 6P4F4.1F9, 7P1D5.1G9, 1B6.4, 2C7.2, 2D6.1, 2F7.3, 2H3.2, 3C11.1, 3E3.1, 3H11.2, 3G8.1, 2B8.1, 3B5.230-C12 (Li01), 38-D01 (Li02), 35-E04 (Li03), 36-009 (Li04), 30-A11 (Li05), 34-F02 (Li06), 29-E07 (Li07), 34-G04 (Li08), 36-A12 (Li09), 28-D02 (Li10), 30-B01 (Li11), 34-B03 (Li12), Li13, Li32, Li33, Li34, 3383 (L1a.1), 3495(L1a.2), 3563 (L1a.3), 3564 (L1a.4), 3565 (L1a.5), 3566 (L1a.6), 3567 (L1a.7), 3568 (L1a.8), 3569 (L1a.9), 3570 (L1a.10), 3571 (L1a.11), 3582 (L1a.12), 1968 (L1a.13), 3011, 3012, 3013, 3418, 3422, 3562, D05, D07, D08, D10 and D11.

In other embodiments, the Sp35 antagonist is an Sp35 antagonist polynucleotide such as an antisense polynucleotide, an aptamer, a ribozyme, a small interfering RNA (siRNA), or a small-hairpin RNA (shRNA).

In additional embodiments, the Sp35 antagonist is an Sp35 aptamer. An Sp35 aptamer is a small polypeptide or a polynucleotide which binds Sp35 and interferes with Sp35 and TrkA interaction and/or inhibits or decreases TrkA phosphorylation.

In other embodiments of the above methods, the Sp35 antagonist is administered by a methods comprising (a) introducing into CNS neurons a polynucleotide which encodes an Sp35 antagonist through operable linkage to an expression control sequence; and (b) allowing expression of said Sp35 antagonist. In some embodiments the CNS neurons are in a mammal and said introducing comprises (a) administering to said mammal a polynucleotide which encodes an Sp35 antagonist through operable linkage to an expression control sequence. In some embodiments, the cultured host cell is derived from the mammal to be treated. In certain embodiments, the polynucleotide is introduced into the host cell or CNS neuron via transfection, electroporation, viral transduction or direct microinjection.

In some embodiments, the polynucleotide is administered as an expression vector. In certain embodiments, the vector is a viral vector which is selected from the group consisting of an adenoviral vector, an alphavirus vector, an enterovirus vector, a pestivirus vector, a lentiviral vector, a baculoviral vector, a herpesvirus vector, an Epstein Barr viral vector, a papovaviral vector, a poxvirus vector, a vaccinia viral vector, a parvovirus, and a herpes simplex viral vector.

BRIEF DESCRIPTION OF THE DRAWINGS/FIGURES

FIG. 1—Immunofluorescence of TrkA and Sp35 (LINGO-1) in different types of neurons from brain and spinal cord tissues.

FIG. 2—Immunofluorescence of TrkA and Sp35 (LINGO-1) in DRG neurons in culture.

FIG. 3—Immunoprecipiation of Sp35 (LINGO-1) and TrkA in 293T cells transfected with Sp35 and TrkA, TrkA alone, Sp35 and p75, Sp35 and p75 and TrkA or TrkA and p75.

FIG. 4—Western blot of DRG—oligodendrocyte co-culture cell lysates transfected with either GFP (control), dominant negative Sp35 (DN) or full length Sp35 (FL). Antibodies were used to detect phosphorylated TrkA (p-TrkA) or unphosphorylated TrkA (TrkA).

FIGS. 5A-5C—Immunofluorescence of DRG-oligodendrocyte co-cultures in the presence of Sp35-Fc (FIG. 5A) or control Fc (FIG. 5B) and nerve growth factor (NGF). An antibody to the myelin protein MBP was used for the immunofluorescence (FIGS. 5A and 5B). FIG. 5C is a graph depicting the number of MBP+ cells/well of DRG-oligodendrocyte co-culture treated with various concentrations of control-Fc or Sp35-Fc polypeptides.

FIG. 6—Western blot of DRG-oligodendrocyte co-cultures infected with viruses encoding full length (FL) or dominant negative (DN) Sp35 (LINGO-1), Nogo Receptor (NgR), Taj, p75 and TrkA. Antibodies to MAG and MBP were used to detect the myelin proteins.

FIG. 7—Western blot of DRG-oligodendrocyte co-cultures treated with the TrkA inhibitor K525a or Sp35-Fc or control-Fc. Antibodies to MBP were used to detect myelin proteins.

FIG. 8—Western blot of phosphorylated TrkA (p-TrkA) and Sp35 (LINGO-1) in DRG-oligodendrocyte co-cultures treated with various amounts of NGF.

FIGS. 9A and B—RT-PCR of TrkA, Sp35 (LINGO-1) and GAPDH expression in oliogodendrocyte progenitor cells (OPCs), schwann cells (SCs) and dorsal root ganglion cells (DRGs) in the presence or absence of NGF or brain-derived neurotrophic factor (BDNF) (FIG. 9A). Western blot of Sp35 in DRG neurons and oligodendrocytes in the presence of various amounts of NGF (FIG. 9B).

FIG. 10—Immunofluorescence of Sp35 expression in DRG neurons in the presence and absence of NGF.

FIG. 11—Western blot of DRG-oligodendrocyte co-cultures infected with viruses encoding full length (FL) or dominant negative (DN) Sp35 (LINGO-1) and or full length (FL) or dominant negative (DN) TrkA. Antibodies to the proteins MAG and MBP were used to detect myelin proteins.

Figure 12:
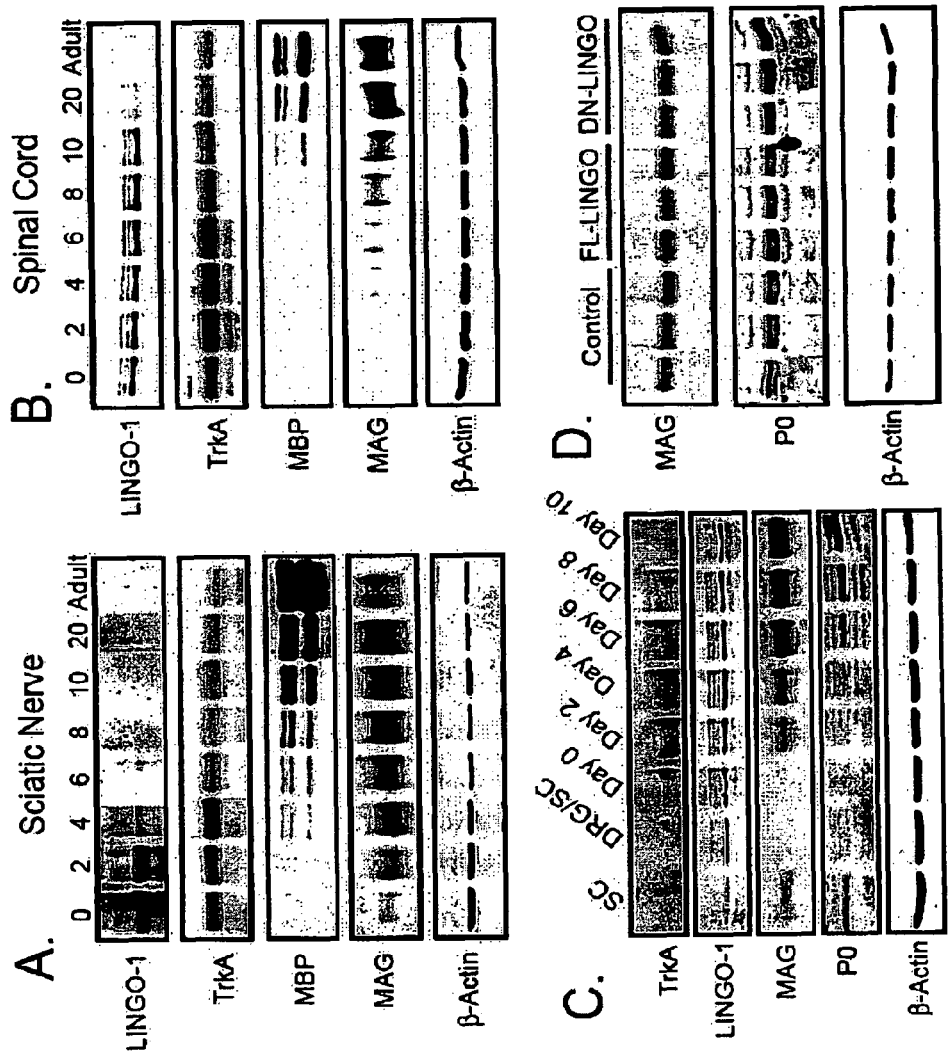

FIG. 12A-D—Western blot of Sp35 (LINGO-1), TrkA, MBP, MAG and β-actin expression at various postnatal days in rat sciatic nerve (FIG. 12A) and spinal cord (FIG. 12B). Western blot of Sp35 (LINGO-1), TrkA, P0, MAG and β-actin expression in DRG/SC co-cultures at various days post induction of myelination by addition of absorbic acid (FIG. 12C). Western blot of MAG, P0 and β-actin expression in DRG/SC co-cultures transfected with lentiviruses expressing full-length Sp35 (FL-LINGO) and dominant-negative Sp35 (DN-LINGO) (FIG. 12D).

Figure 13:
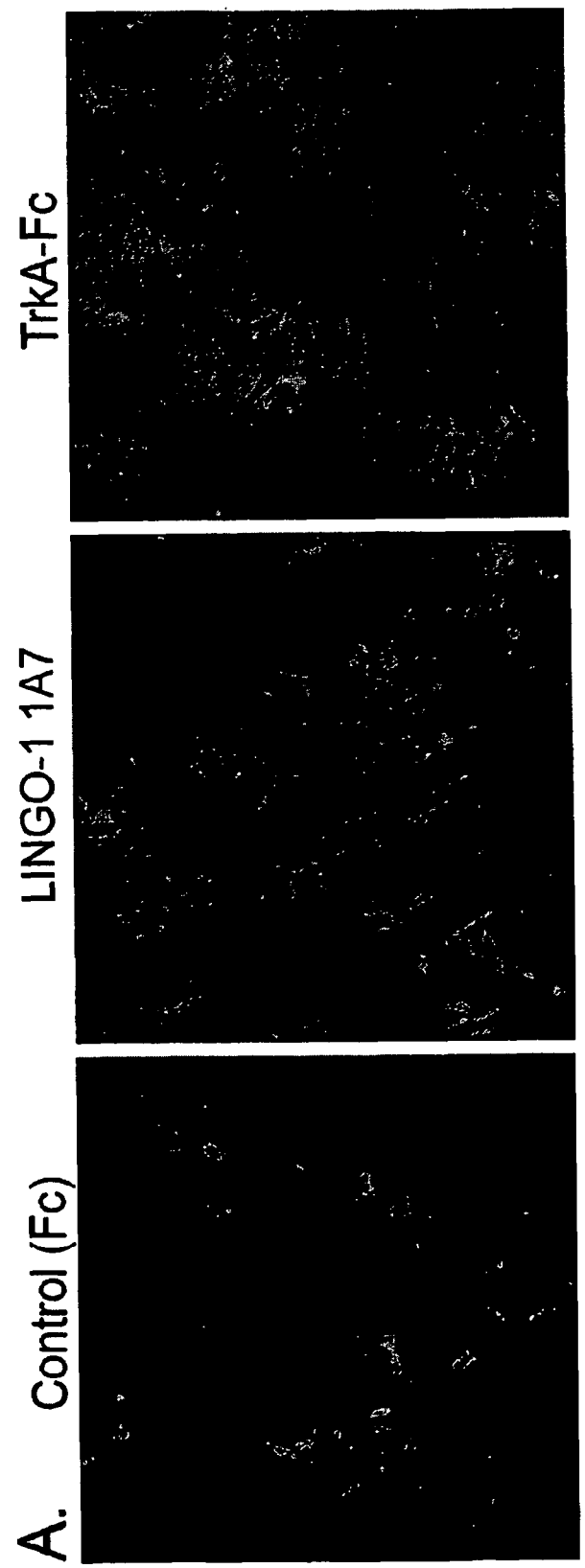

FIG. 13—Immunofluorescence of MBP expression in oligodendrocyte and DRG co-cultures in the presence of 100 ng/ml NGF and IgG (Fc—control) or 1A7 Sp35 antibody or TrkA-Fc in the absence of NGF.

DETAILED DESCRIPTION OF THE INVENTION

Definitions

Unless defined otherwise, all technical and scientific terms used herein have the same meaning as commonly understood by one of ordinary skill in the art to which this invention belongs. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference.

Although methods and materials similar or equivalent to those described herein can be used in practice or testing of the present invention, suitable methods and materials are described below. The materials, methods and examples are illustrative only and are not intended to be limiting. Other features and advantages of the invention will be apparent from the detailed description and from the claims.

In order to further define this invention, the following terms and definitions are provided.

It is to be noted that the term "a" or "an" entity, refers to one or more of that entity; for example, "an immunoglobulin molecule," is understood to represent one or more immunoglobulin molecules. As such, the terms "a" (or "an"), "one or more," and "at least one" can be used interchangeably herein.

Throughout this specification and claims, the word "comprise," or variations such as "comprises" or "comprising," indicate the inclusion of any recited integer or group of integers but not the exclusion of any other integer or group of integers. The term "comprising" is inclusive or open-ended and does not exclude additional, unrecited elements or method steps. The phrase "consisting essentially of" indicates the inclusion of the specified materials or steps as well as those which do not materially affect the basic and novel characteristics of the claimed invention. As used herein, the term "consisting" refers only to indicated material or method steps.

As used herein, a "therapeutically effective amount" refers to an amount effective, at dosages and for periods of time necessary, to achieve a desired therapeutic result. A therapeutic result may be, e.g., lessening of symptoms, prolonged survival, improved mobility, and the like. A therapeutic result need not be a "cure".

As used herein, the term "treatment" or "treating" refers to the administration of an agent to an animal in order to ameliorate or lessen the symptoms of a disease. Additionally, the terms "treatment" or "treating" refers to the administration of an agent to an animal to prevent the progression of a disease.

As used herein, a "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

As used herein, "oligodendrocyte progenitor cells" include any cell which can give rise to a mature myelinating oligodendrocyte. Non limiting examples include: A2B5 progenitor cells (which express A2B5 protein), pre-myelinating oligodendrocytes (which express O1 and O4 proteins). For a general review of oligodendrocyte biology, see, e.g., Baumann and Pham-Dinh, *Physiol. Rev.* 81: 871-927 (2001) which is incorporated herein by reference.

As used herein, a "polynucleotide" can contain the nucleotide sequence of the full length cDNA sequence, including the untranslated 5' and 3' sequences, the coding sequences, as well as fragments, epitopes, domains, and variants of the nucleic acid sequence. The polynucleotide can be composed of any polyribonucleotide or polydeoxyribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotides can be composed of triple-stranded regions comprising RNA or DNA or both RNA and DNA. polynucleotides may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

In the present invention, a "polypeptide" can be composed of amino acids joined to each other by peptide bonds or modified peptide bonds, i.e., peptide isosteres, and may contain amino acids other than the 20 gene-encoded amino acids (e.g. non-naturally occurring amino acids). The polypeptides of the present invention may be modified by either natural processes, such as posttranslational processing, or by chemical modification techniques which are well known in the art. Such modifications are well described in basic texts and in more detailed monographs, as well as in a voluminous research literature. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslational natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, Proteins—Structure And Molecular Properties, 2nd Ed., T. E. Creighton, W.H. Freeman and Company, New York (1993); Posttranslational Covalent Modification of Proteins, B. C. Johnson, Ed., Academic Press, New York, pgs. 1-12 (1983); Seifter et al., *Meth Enzymol* 182:626-646 (1990); Rattan et al., *Ann NY Acad Sci* 663:48-62 (1992).)

The terms "fragment," "variant," "derivative" and "analog" when referring to an Sp35 or TrkA antagonist of the present invention include any antagonist molecules which retain at least some ability to inhibit Sp35 activity or TrkA activity. Sp35 and TrkA antagonists as described herein may include fragment, variant, or derivative molecules therein without limitation, so long as the Sp35 or TrkA antagonist still serves its function. Soluble Sp35 or TrkA polypeptides of the present invention may include Sp35 or TrkA proteolytic fragments, deletion fragments and in particular, fragments which more easily reach the site of action when delivered to an animal. Polypeptide fragments further include any portion of the polypeptide which comprises an antigenic or immunogenic epitope of the native polypeptide, including linear as well as three-dimensional epitopes. Soluble Sp35 or TrkA polypeptides of the present invention may comprise variant Sp35 or TrkA regions, including fragments as described above, and also polypeptides with altered amino acid sequences due to amino acid substitutions, deletions, or insertions. Variants may occur naturally, such as an allelic variant. By an "allelic variant" is intended alternate forms of a gene occupying a given locus on a chromosome of an organism. *Genes II*, Lewin, B., ed., John Wiley & Sons, New York (1985). Non-naturally occurring variants may be produced using art-known mutagenesis techniques. Soluble Sp35 or TrkA polypeptides may comprise conservative or non-conservative amino acid substitutions, deletions or additions. Sp35 or TrkA antagonists of the present invention may also include derivative molecules. For example, soluble Sp35 or TrkA polypeptides of the present invention may include Sp35 or TrkA regions which have been altered so as to exhibit additional features not found on the native polypeptide. Examples include fusion proteins and protein conjugates.

In the present invention, a "polypeptide fragment" refers to a short amino acid sequence of an Sp35 or TrkA polypeptide. Protein fragments may be "free-standing," or comprised within a larger polypeptide of which the fragment forms a part or region. Representative examples of polypeptide fragments of the invention include, for example, fragments comprising about 5 amino acids, about 10 amino acids, about 15 amino acids, about 20 amino acids, about 30 amino acids, about 40 amino acids, about 50 amino acids, about 60 amino acids, about 70 amino acids, about 80 amino acids, about 90 amino acids, and about 100 amino acids or more in length.

In certain embodiments, Sp35 or TrkA antagonists for use in the methods disclosed herein are "antibody" or "immunoglobulin" molecules, or immunospecific fragments thereof, e.g., naturally occurring antibody or immunoglobulin molecules or engineered antibody molecules or fragments that bind antigen in a manner similar to antibody molecules. The terms "antibody" and "immunoglobulin" are used interchangeably herein. Additionally, immunoglobulin molecules used in the methods of the invention are also described as "immunospecific" or "antigen-specific" or "antigen-binding" molecules and are used interchangeably to refer to antibody molecules and fragments thereof. An antibody or immunoglobulin comprises at least the variable domain of a heavy chain, and normally comprises at least the variable domains of a heavy chain and a light chain. Basic immunoglobulin structures in vertebrate systems are relatively well understood. See, e.g., Harlow et al., Antibodies: A Laboratory Manual, (Cold Spring Harbor Laboratory Press, 2nd ed. 1988), incorporated herein by reference.

As will be discussed in more detail below, the term "immunoglobulin" comprises five broad classes of polypeptides that can be distinguished biochemically. All five classes are clearly within the scope of the present invention, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Both the light and heavy chains are divided into regions of structural and functional homology. The terms "constant" and "variable" are used functionally. In this regard, it will be appreciated that the variable domains of both the light ($V_L$) and heavy ($V_H$) chain portions determine antigen recognition and specificity. Conversely, the constant domains of the light chain ($C_L$) and the heavy chain ($C_H1$, $C_H2$ or $C_H3$) confer important biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the $C_H3$ and $C_L$ domains actually comprise the carboxy-terminus of the heavy and light chain, respectively.

Light chains are classified as either kappa or lambda ($\kappa$, $\lambda$). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain. Those skilled in the art will appreciate that heavy chains are classified as gamma, mu, alpha, delta, or epsilon, ($\gamma$, $\beta$, $\delta$, $\epsilon$) with some subclasses among them (e.g., $\gamma1$-$\gamma4$). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgA_1$, etc. are well characterized and are known to confer functional specialization. Modified versions of each of these classes and isotypes are readily discernable to the skilled artisan in view of the instant disclosure and, accordingly, are within the scope of the instant invention.

As indicated above, the variable region allows the antibody to selectively recognize and specifically bind epitopes on antigens. That is, the $V_L$ domain and $V_H$ domain of an antibody combine to form the variable region that defines a three dimensional antigen binding site. This quaternary antibody structure forms the antigen binding site present at the end of each arm of the Y. More specifically, the antigen binding site is defined by three complementary determining regions (CDRs) on each of the $V_H$ and $V_L$ chains. In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., *Nature* 363:446-448 (1993).

In naturally occurring antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see, "Sequences of Proteins of Immunological Interest," Kabat, E., et al., U.S. Department of Health and Human Services, (1983); and Chothia and Lesk, *J. Mol. Biol.*, 196: 901-917 (1987), which are incorporated herein by reference in their entireties).

In camelid species, however, the heavy chain variable region, referred to as $V_H H$, forms the entire CDR. The main differences between camelid $V_H H$ variable regions and those derived from conventional antibodies ($V_H$) include (a) more hydrophobic amino acids in the light chain contact surface of $V_H$ as compared to the corresponding region in $V_H H$, (b) a longer CDR3 in $V_H H$, and (c) the frequent occurrence of a disulfide bond between CDR1 and CDR3 in $V_H H$.

In one embodiment, an antigen binding molecule for use in the methods of the invention comprises at least one heavy or light chain CDR of an antibody molecule. In another embodiment, an antigen binding molecule for use in the methods of the invention comprises at least two CDRs from one or more antibody molecules. In another embodiment, an antigen binding molecule for use in the methods of the invention comprises at least three CDRs from one or more antibody molecules. In another embodiment, an antigen binding molecule for use in the methods of the invention comprises at least four CDRs from one or more antibody molecules. In another embodiment, an antigen binding molecule for use in the methods of the invention comprises at least five CDRs from one or more antibody molecules. In another embodiment, an antigen binding molecule for use in the methods of the invention comprises at least six CDRs from one or more antibody molecules. Exemplary antibody molecules comprising at least one CDR that can be included in the subject antigen binding molecules are known in the art and exemplary molecules are described herein.

Antibodies or immunospecific fragments thereof for use in the methods of the invention include, but are not limited to, polyclonal, monoclonal, multispecific, human, humanized, primatized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a $V_L$ or $V_H$ domain, fragments produced by a Fab expression library, and anti-idiotypic (anti-Id) antibodies (including, e.g., anti-Id antibodies to binding molecules disclosed herein). ScFv molecules are known in the art and are described, e.g., in U.S. Pat. No. 5,892,019. Immunoglobulin or antibody molecules of the invention can be of any type (e.g., IgG, IgE, IgM, IgD, IgA, and IgY), class (e.g., IgG$_1$, IgG$_2$, IgG$_3$, IgG$_4$, IgA$_1$ and IgA$_2$) or subclass of immunoglobulin molecule.

Antibody fragments, including single-chain antibodies, may comprise the variable region(s) alone or in combination with the entirety or a portion of the following: hinge region, $C_H 1$, $C_H 2$, and $C_H 3$ domains of the heavy chain, or $C_L$ of the light chain. Also included in the invention are antigen-binding fragments also comprising any combination of variable region(s) with a hinge region, $C_H 1$, $C_H 2$, $C_H 3$, or $C_L$ domain. Antibodies or immunospecific fragments thereof for use in the methods disclosed herein may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks). As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example, in U.S. Pat. No. 5,939,598 by Kucherlapati et al.

As used herein, the term "heavy chain portion" includes amino acid sequences derived from an immunoglobulin heavy chain. A polypeptide comprising a heavy chain portion comprises at least one of: a $C_H 1$ domain, a hinge (e.g., upper, middle, and/or lower hinge region) domain, a $C_H 2$ domain, a $C_H 3$ domain, or a variant or fragment thereof. For example, a heavy chain portion may comprise a polypeptide chain comprising a $C_H 1$ domain; a polypeptide chain comprising a $C_H 1$ domain, at least a portion of a hinge domain, and a $C_H 2$ domain; a polypeptide chain comprising a $C_H 1$ domain and a $C_H 3$ domain; a polypeptide chain comprising a $C_H 1$ domain, at least a portion of a hinge domain, and a $C_H 3$ domain, or a polypeptide chain comprising a $C_H 1$ domain, at least a portion of a hinge domain, a $C_H 2$ domain, and a $C_H 3$ domain. The heavy chain portion may also include a polypeptide comprising a polypeptide chain comprising a $C_H 3$ domain. Further, a binding polypeptide for use in the invention may lack at least a portion of a $C_H 2$ domain (e.g., all or part of a $C_H 2$ domain). As set forth above, it will be understood by one of ordinary skill in the art that these domains (e.g., the heavy chain portions) may be modified such that they vary in amino acid sequence from the naturally occurring immunoglobulin molecule.

In certain Sp35 or TrkA antagonist antibodies or immunospecific fragments thereof for use in the methods disclosed herein, the heavy chain portions of one polypeptide chain of a multimer are identical to those on a second polypeptide chain of the multimer. Alternatively, heavy chain portion-containing monomers for use in the methods of the invention are not identical. For example, each monomer may comprise a different target binding site, forming, for example, a bispecific antibody.

The heavy chain portions of a binding polypeptide for use in the methods disclosed herein may be derived from different immunoglobulin molecules. For example, a heavy chain portion of a polypeptide may comprise a $C_H1$ domain derived from an $IgG_1$ molecule and a hinge region derived from an $IgG_3$ molecule. In another example, a heavy chain portion can comprise a hinge region derived, in part, from an $IgG_1$ molecule and, in part, from an $IgG_3$ molecule. In another example, a heavy chain portion can comprise a chimeric hinge derived, in part, from an $IgG_1$ molecule and, in part, from an $IgG_4$ molecule.

As used herein, the term "light chain portion" includes amino acid sequences derived from an immunoglobulin light chain. Preferably, the light chain portion comprises at least one of a $V_L$ or $C_L$ domain.

An isolated nucleic acid molecule encoding a non-natural variant of a polypeptide derived from an immunoglobulin (e.g., an immunoglobulin heavy chain portion or light chain portion) can be created by introducing one or more nucleotide substitutions, additions or deletions into the nucleotide sequence of the immunoglobulin such that one or more amino acid substitutions, additions or deletions are introduced into the encoded protein. Mutations may be introduced by standard techniques, such as site-directed mutagenesis and PCR-mediated mutagenesis. Preferably, conservative amino acid substitutions are made at one or more non-essential amino acid residues.

Antibodies or immunospecific fragments thereof for use in the methods disclosed herein may also be described or specified in terms of their binding affinity to a polypeptide of the invention. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $5\times10^{-6}$M, $10^{-6}$ M, $5\times10^{-7}$ M, $10^{-7}$ M, $5\times10^{-8}$ M, $10^{-8}$M, $5\times$M, $10^{-9}$ M, $5\times10^{-10}$ M, $10^{-10}$ M, $5\times10^{-11}$ M, $10^{-11}$ M, $5\times10^{-12}$M, $10^{-12}$M, $5\times10^{-13}$ M, $10^{-13}$ M, $5\times10^{-14}$ M, $10^{-14}$ M, $5\times10^{-15}$M, or $10^{-15}$M.

Antibodies or immunospecific fragments thereof for use in the methods disclosed herein act as antagonists of Sp35 or TrkA as described herein. For example, an antibody for use in the methods of the present invention may function as an antagonist, blocking or inhibiting the suppressive activity of the Sp35 or TrkA polypeptide.

As used herein, the term "chimeric antibody" will be held to mean any antibody wherein the immunoreactive region or site is obtained or derived from a first species and the constant region (which may be intact, partial or modified in accordance with the instant invention) is obtained from a second species. In certain embodiments the target binding region or site will be from a non-human source (e.g. mouse or primate) and the constant region is human.

As used herein, the term "engineered antibody" refers to an antibody in which the variable domain in either the heavy and light chain or both is altered by at least partial replacement of one or more CDRs from an antibody of known specificity and, if necessary, by partial framework region replacement and sequence changing. Although the CDRs may be derived from an antibody of the same class or even subclass as the antibody from which the framework regions are derived, it is envisaged that the CDRs will be derived from an antibody of different class and preferably from an antibody from a different species. An engineered antibody in which one or more "donor" CDRs from a non-human antibody of known specificity is grafted into a human heavy or light chain framework region is referred to herein as a "humanized antibody." It may not be necessary to replace all of the CDRs with the complete CDRs from the donor variable region to transfer the antigen binding capacity of one variable domain to another. Rather, it may only be necessary to transfer those residues that are necessary to maintain the activity of the target binding site. Given the explanations set forth in, e.g., U.S. Pat. Nos. 5,585,089, 5,693,761, 5,693,762, and 6,180,370, it will be well within the competence of those skilled in the art, either by carrying out routine experimentation or by trial and error testing to obtain a functional engineered or humanized antibody.

As used herein, the terms "linked," "fused" or "fusion" are used interchangeably. These terms refer to the joining together of two more elements or components, by whatever means including chemical conjugation or recombinant means. An "in-frame fusion" refers to the joining of two or more open reading frames (ORFs) to form a continuous longer ORF, in a manner that maintains the correct reading frame of the original ORFs. Thus, the resulting recombinant fusion protein is a single protein containing two or more segments that correspond to polypeptides encoded by the original ORFs (which segments are not normally so joined in nature.) Although the reading frame is thus made continuous throughout the fused segments, the segments may be physically or spatially separated by, for example, in-frame linker sequence.

In the context of polypeptides, a "linear sequence" or a "sequence" is an order of amino acids in a polypeptide in an amino to carboxyl terminal direction in which residues that neighbor each other in the sequence are contiguous in the primary structure of the polypeptide.

The term "expression" as used herein refers to a process by which a gene produces a biochemical, for example, an RNA or polypeptide. The process includes any manifestation of the functional presence of the gene within the cell including, without limitation, gene knockdown as well as both transient expression and stable expression. It includes without limitation transcription of the gene into messenger RNA (mRNA), transfer RNA (tRNA), small hairpin RNA (shRNA), small interfering RNA (siRNA) or any other RNA product and the translation of such mRNA into polypeptide(s). If the final desired product is biochemical, expression includes the creation of that biochemical and any precursors.

By "subject" or "individual" or "animal" or "patient" or "mammal," is meant any subject, particularly a mammalian subject, for whom diagnosis, prognosis, or therapy is desired. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. In certain embodiments, the mammal is a human subject.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

Sp35 (LINGO-1/LRRN6)

Naturally occurring human Sp35 is a glycosylated nervous-system-specific protein consisting of 614 amino acids (SEQ ID NO: 2). The human Sp35 polypeptide contains an LRR domain consisting of 14 leucine-rich repeats (including N- and C-terminal caps), an Ig domain, a transmembrane region, and a cytoplasmic domain. The cytoplasmic domain contains a canonical tyrosine phosphorylation site. In addition, the naturally occurring Sp35 protein contains a signal sequence, a short basic region between the LRRCT and Ig domain, and a transmembrane region between the Ig domain and the cytoplasmic domain. The human. Sp35 gene contains alternative translation start codons, so that six additional amino acids (MQVSKR; SEQ ID NO:7) may or may not be present at the N-terminus of the Sp35 signal sequence. Table 1 lists the Sp35 domains and other regions; according to amino acid residue number, based on the sequence of SEQ ID NO:2. The Sp35 polypeptide is characterized in more detail in PCT Publication No. WO 2004/085648 and U.S. Published Application No. 2006/0009388 A1, which are incorporated herein by reference in their entireties.

TABLE 1

| Domain or Region | Beginning Residue | Ending Residue |
| --- | --- | --- |
| Signal Sequence | 1 | 33 or 35 |
| LRRNT | 34 or 36 | 64 |
| LRR | 66 | 89 |
| LRR | 90 | 113 |
| LRR | 114 | 137 |
| LRR | 138 | 161 |
| LRR | 162 | 185 |
| LRR | 186 | 209 |
| LRR | 210 | 233 |
| LRR | 234 | 257 |
| LRR | 258 | 281 |
| LRR | 282 | 305 |
| LRR | 306 | 329 |
| LRR | 330 | 353 |
| LRRCT | 363 | 414 or 416 |
| Basic | 415 or 417 | 424 |
| Ig | 419 | 493 |
| Connecting sequence | 494 | 551 |
| Transmembrane | 552 | 576 |
| Cytoplasmic | 577 | 614 |

Tissue distribution and developmental expression of Sp35 have been studied in humans and rats. Sp35 biology has been studied in an experimental animal (rat) model. Expression of rat Sp35 is localized to nervous-system neurons and brain oligodendrocytes, as determined by northern blot and immuno-histochemical staining. Rat Sp35 mRNA expression level is regulated developmentally, peaking shortly after birth, i.e., ca. postnatal day one. In a rat spinal cord transection injury model, Sp35 is up-regulated at the injury site, as determined by RT-PCR. In addition, Sp35 has been shown to interact with Nogo66 Receptor (Nogo receptor). See, e.g., International Patent Application No. PCT/US2004/00832, PCT Publication No. WO2004/08564.

Sp35 (LINGO-1) is an additional component of the Nogo Receptor-1-p75-Taj neurotrophin receptor complex. See Mi et al., Nat. Neurosci. 7:221-228 (2004), which is incorporated herein by reference. Unlike Nogo receptor 1, Sp35 gene expression is increased when adult nerve cells in the spinal cord are exposed to traumatic injuries, suggesting that Sp35 has an important biological role for CNS neurological function. Id.

The nucleotide sequence for the full-length human Sp35 molecule is as follows:

(SEQ ID NO: 1)
ATGCTGGCGGGGGGCGTGAGGAGCATGCCCAGCCCCTCCTGGCCTGCTG

GCAGCCCATCCTCCTGCTGGTGCTGGGCTCAGTGCTGTCAGGCTCGGCCA

CGGGCTGCCCGCCCCGCTGCGAGTGCTCCGCCCAGGACCGCGCTGTGCTG

TGCCACCGCAAGCGCTTTGTGGCAGTCCCCGAGGGCATCCCCACCGAGAC

GCGCCTGCTGGACCTAGGCAAGAACCGCATCAAAACGCTCAACCAGGACG

AGTTCGCCAGCTTCCCGCACCTGGAGGAGCTGGAGCTCAACGAGAACATC

GTGAGCGCCGTGGAGCCCGGCGCCTTCAACAACCTCTTCAACCTCCGGAC

GCTGGGTCTCCGCAGCAACCGCCTGAAGCTCATCCCGCTAGGCGTCTTCA

CTGGCCTCAGCAACCTGACCAAGCTGGACATCAGCGAGAACAAGATTGTT

ATCCTGCTGGACTACATGTTTCAGGACCTGTACAACCTCAAGTCACTGGA

GGTTGGCGACAATGACCTCGTCTACATCTCTCACCGCGCCTTCAGCGGCC

TCAACAGCCTGGAGCAGCTGACGCTGGAGAAATGCAACCTGACCTCCATC

CCCACCGAGGCGCTGTCCCACCTGCACGGCCTCATCGTCCTGAGGCTCCG

GCACCTCAACATCAATGCCATCCGGGACTACTCCTTCAAGAGGCTCTACC

GACTCAAGGTCTTGGAGATCTCCCACTGGCCCTACTTGGACACCATGACA

CCCAACTGCCTCTACGGCCTCAACCTGACGTCCCTGTCCATCACACACTG

CAATCTGACCGCTGTGCCCTACCTGGCCGTCCGCCACCTAGTCTATCTCC

GCTTCCTCAACCTCTCCTACAACCCCATCAGCACCATTGAGGGCTCCATG

TTGCATGAGCTGCTCCGGCTGCAGGAGATCCAGCTGGTGGGCGGGCAGCT

GGCCGTGGTGGAGCCCTATGCCTTCCGCGGCCTCAACTACCTGCGCGTGC

TCAATGTCTCTGGCAACCAGCTGACCACACTGGAGGAATCAGTCTTCCAC

TCGGTGGGCAACCTGGAGACACTCATCCTGGACTCCAACCCGCTGGCCTG

CGACTGTCGGCTCCTGTGGGTGTTCCGGCGCCGCTGGCGGCTCAACTTCA

ACCGGCAGCAGCCCACGTGCGCCACGCCCGAGTTTGTCCAGGGCAAGGAG

TTCAAGGACTTCCCTGATGTGCTACTGCCCAACTACTTCACCTGCCGCCG

CGCCCGCATCCGGGACCGCAAGGCCCAGCAGGTGTTTGTGGACGAGGGCC

ACACGGTGCAGTTTGTGTGCCGGGCCGATGGCGACCCGCCGCCCGCCATC

CTCTGGCTCTCACCCCGAAAGCACCTGGTCTCAGCCAAGAGCAATGGGCG

-continued

```
GCTCACAGTCTTCCCTGATGGCACGCTGGAGGTGCGCTACGCCCAGGTAC

AGGACAACGGCACGTACCTGTGCATCGCGGCCAACGCGGGCGGCAACGAC

TCCATGCCCGCCCACCTGCATGTGCGCAGCTACTCGCCCGACTGGCCCCA

TCAGCCCAACAAGACCTTCGCTTTCATCTCCAACCAGCCGGGCGAGGGAG

AGGCCAACAGCACCCGCGCCACTGTGCCTTTCCCCTTCGACATCAAGACC

CTCATCATCGCCACCACCATGGGCTTCATCTCTTTCCTGGGCGTCGTCCT

CTTCTGCCTGGTGCTGCTGTTTCTCTGGAGCCGGGGCAAGGGCAACACAA

AGCACAACATCGAGATCGAGTATGTGCCCCGAAAGTCGGACGCAGGCATC

AGCTCCGCCGACGCGCCCCGCAAGTTCAACATGAAGATGATATGA.
```

The polypeptide sequence for the full-length human Sp35 polypeptide is as follows:

(SEQ ID NO: 2)
```
MLAGGVRSMPSPLLACWQPILLLVLGSVLSGSATGCPPRCECSAQDRAVL

CHRKRFVAVPEGIPTETRLLDLGKNRIKTLNQDEFASFPHLEELELNENI

VSAVEPGAFNNLFNLRTLGLRSNRLKLIPLGVFTGLSNLTKLDISENKIV

ILLDYMFQDLYNLKSLEVGDNDLVYISHRAFSGLNSLEQLTLEKCNLTSI

PTEALSHLHGLIVLRLRHLNINAIRDYSFKRLYRLKVLEISHWPYLDTMT

PNCLYGLNLTSLSITHCNLTAVPYLAVRHLVYLRFLNLSYNPISTIEGSM

LHELLRLQEIQLVGGQLAVVEPYAFRGLNYLRVLNVSGNQLTTLEESVFH

SVGNLETLILDSNPLACDCRLLWVFRRRWRLNFNRQQPTCATPEFVQGKE

FKDFPDVLLPNYFTCRRARIRDRKAQQVFVDEGHTVQFVCRADGDPPPAI

LWLSPRKHLVSAKSNGRLTVFPDGTLEVRYAQVQDNGTYLCIAANAGGND

SMPAHLHVRSYSPDWPHQPNKTFAFISNQPGEGEANSTRATVPFPFDIKT

LIIATTMGFISFLGVVLFCLVLLFLWSRGKGNTKHNIEIEYVPRKSDAGI

SSADAPRKFNMKMI.
```

TrkA or gp140$^{trk}$

The neurotrophins are a small family of highly homologous growth factors responsible for differentiation, survival and function of neurons. In mammals, the known neurotrophins are nerve growth factor (NGF), brain-derived neurotrophic factor (BDNF), neurotrophin-3 (NT-3), neurotrophin-4 (NT-4), also known as NT-4/5 or NT-5, and neurotrophin-6 (NT-6). Barbacid, *J. of Neurobiol.* 25:1386-1403 (1994). Neurotrophins bind two receptor types, the p75 neurotrophin receptor (p75$^{NTR}$) and the three members (in mammals) of the Trk receptor family of tyrosine kinases (TrkA, TrkB and TrkC). Binding of a neurotrophin to a Trk receptor extracellular domain initiates a signal transduction pathway. The binding of the neurotrophin leads to autophosphorylation of the receptor which induces homodimerization. Autophosphorylation of TrkA leads to coupling of the signaling pathway to phosphatidylinositol and the p21$^{RAS}$ pathway.

There are two tyrosine protein kinase isoforms of 790 and 796 amino acid residues of TrkA. Barbacid, *J. of Neurobiol.* 25:1386-1403 (1994). The two isoforms differ in the presence of 6 amino acid residues (VSFSPV (SEQ ID NO:15)) located in the extracellular domain. The 796 amino acid TrkA molecule is primarily expressed in neuronal cells, while the 790 amino acid form has been found in non neuronal cells. Barbacid, *J. of Neurobiol.* 25:1386-1403 (1994). The extracellular domain of the TrkA receptor is composed of a cysteine-cluster (CCI), a leucine-rich motif composed of three tandem leucine rich motifs (LRM) of 24 amino acids, and a second cysteine-cluster (CCII), followed by two immunoglobulin-like domains (IgI and IgII of the C2 type similar to the neuronal cell adhesion N-CAM molecules). See Urfer et al., *J. of Biol. Chem.* 273:5829-5840 (1998) and Barbacid, *J. of Neurobiol.* 25:1386-1403 (1994). The extracellular domain is 391 amino acids in length and spans from about amino acid 33 to about amino acid 423 of SEQ ID NO:4. See UniProtKB/Swiss-Prot Entry P04629.

The following nucleotide sequence was reported as the mRNA for human TrkA receptor and is accession number NM_002529 in Genbank.

(SEQ ID NO: 3)
```
TGCAGCTGGGAGCGCACAGACGGCTGCCCCGCCTGAGCGAGGCGGGCGCC

GCCGCGATGCTGCGAGGCGGACGGCGCGGGCAGCTTGGCTGGCACAGCTG

GGCTGCGGGGCCGGGCAGCCTGCTGGCTTGGCTGATACTGGCATCTGCGG

GCGCCGCACCCTGCCCCGATGCCTGCTGCCCCACGGCTCCTCGGGACTG

CGATGCACCCGGGATGGGGCCCTGGATAGCCTCCACCACCTGCCCGGCGC

AGAGAACCTGACTGAGCTCTACATCGAGAACCAGCAGCATCTGCAGCATC

TGGAGCTCCGTGATCTGAGGGGCCTGGGGGAGCTGAGAAACCTCACCATC

GTGAAGAGTGGTCTCCGTTTCGTGGCGCCAGATGCCTTCCATTTCACTCC

TCGGCTCAGTCGCCTGAATCTCTCCTTCAACGCTCTGGAGTCTCTCTCCT

GGAAAACTGTGCAGGGCCTCTCCTTACAGGAACTGGTCCTGTCGGGGAAC

CCTCTGCACTGTTCTTGTGCCCTGCGCTGGCTACAGCGCTGGGAGGAGGA

GGGACTGGGCGGAGTGCCTGAACAGAAGCTGCAGTGTCATGGGCAAGGGC

CCCTGGCCCACATGCCCAATGCCAGCTGTGGTGTGCCCACGCTGAAGGTC

CAGGTGCCCAATGCCTCGGTGGATGTGGGGGACGACGTGCTGCTGCGGTG

CCAGGTGGAGGGCGGGGCCTGGAGCAGGCCGGCTGGATCCTCACAGAGC

TGGAGCAGTCAGCCACGGTGATGAAATCTGGGGGTCTGCCATCCCTGGGG

CTGACCCTGGCCAATGTCACCAGTGACCTCAACAGGAAGAACGTGACGTG

CTGGGCAGAGAACGATGTGGGCCGGGCAGAGGTCTCTGTTCAGGTCAACG

TCTCCTTCCCGGCCAGTGTGCAGCTGCACACGGCGGTGGAGATGCACCAC

TGGTGCATCCCCTTCTCTGTGGATGGGCAGCCGGCACCGTCTCTGCGCTG

GCTCTTCAATGGCTCCGTGCTCAATGAGACCAGCTTCATCTTCACTGAGT

TCCTGGAGCCGGCAGCCAATGAGACCGTGCGGCACGGGTGTCTGCGCCTC

AACCAGCCCACCCACGTCAACAACGGCAACTACACGCTGCTGGCTGCCAA

CCCCTTCGGCCAGGCCTCCGCCTCCATCATGGCTGCCTTCATGGACAACC

CTTTCGAGTTCAACCCCGAGGACCCCATCCCTGTCTCCTTCTCGCCGGTG

GACACTAACAGCACATCTGGAGACCCGGTGGAGAAGAAGGACGAAACACC

TTTTGGGGTCTCGGTGGCTGTGGGCCTGGCCGTCTTTGCCTGCCTCTTCC

TTTCTACGCTGCTCCTTGTGCTCAACAAATGTGGACGGAGAAACAAGTTT

GGGATCAACCGCCCGGCTGTGCTGGCTCCAGAGGATGGGCTGGCCATGTC

CCTGCATTTCATGACATTGGGTGGCAGCTCCCTGTCCCCACCGACGGCA

AAGGCTCTGGGCTCCAAGGCCACATCATCGAGAACCCACAATACTTCAGT
```

-continued

```
GATGCCTGTGTTCACCACATCAAGCGCCGGGACATCGTGCTCAAGTGGGA
GCTGGGGGAGGGCGCCTTTGGGAAGGTCTTCCTTGCTGAGTGCCACAACC
TCCTGCCTGAGCAGGACAAGATGCTGGTGGCTGTCAAGGCACTGAAGGAG
GCGTCCGAGAGTGCTCGGCAGGACTTCCAGCGTGAGGCTGAGCTGCTCAC
CATGCTGCAGCACCAGCACATCGTGCGCTTCTTCGGCGTCTGCACCGAGG
GCCGCCCCTGCTCATGGTCTTTGAGTATATGCGGCACGGGGACCTCAAC
CGCTTCCTCCGATCCCATGGACCTGATGCCAAGCTGCTGGCTGGTGGGGA
GGATGTGGCTCCAGGCCCCCTGGGTCTGGGGCAGCTGCTGGCCGTGGCTA
GCCAGGTCGCTGCGGGATGGTGTACCTGGCGGGTCTGCATTTTGTGCAC
CGGGACCTGGCCACACGCAACTGTCTAGTGGGCCAGGGACTGGTGGTCAA
GATTGGTGATTTTGGCATGAGCAGGGATATCTACAGCACCGACTATTACC
GTGTGGGAGGCCGCACCATGCTGCCCATTCGCTGGATGCCGCCCGAGAGC
ATCCTGTACCGTAAGTTCACCACCGAGAGCGACGTGTGGAGCTTCGGCGT
GGTGCTCTGGGAGATCTTCACCTACGGCAAGCAGCCCTGGTACCAGCTCT
CCAACACGGAGGCAATCGACTGCATCACGCAGGGACGTGAGTTGGAGCGG
CCACGTGCCTGCCCACCAGAGGTCTACGCCATCATGCGGGGCTGCTGGCA
GCGGGAGCCCCAGCAACGCCACAGCATCAAGGATGTGCACGCCCGGCTGC
AAGCCCTGGCCCAGGCACCTCCTGTCTACCTGGATGTCCTGGGCTAGGGG
GCCGGCCCAGGGGCTGGGAGTGGTTAGCCGGAATACTGGGGCCTGCCCTC
AGCATCCCCATAGCTCCCAGCAGCCCCAGGGTGATCTCAAAGTATCTAA
TTCACCCTCAGCATGTGGGAAGGGACAGGTGGGGGCTGGGAGTAGAGGAT
GTTCCTGCTTCTCTAGGCAAGGTCCCGTCATAGCAATTATATTTATTATC
CCTTGAAAAAAAA
```

The following polypeptide sequence was reported as the human TrkA polypeptide sequence (796 amino acid form) and has the accession number NP_002520 in Genbank.

```
                                          (SEQ ID NO: 4)
MLRGGRRGQLGWHSWAAGPGSLLAWLILASAGAAPCPDACCPHGSSGLRC
TRDGALDSLHHLPGAENLTELYIENQQHLQHLELRDLRGLGELRNLTIVK
SGLRFVAPDAFHFTPRLSRLNLSFNALESLSWKTVQGLSLQELVLSGNPL
HCSCALRWLQRWEEEGLGGVPEQKLQCHGQGPLAHMPNASCGVPTLKVQV
PNASVDVGDDVLLRCQVEGRGLEQAGWILTELEQSATVMKSGGLPSLGLT
LANVTSDLNRKNVTCWAENDVGRAEVSVQVNVSFPASVQLHTAVEMHHWC
IPFSVDGQPAPSLRWLFNGSVLNETSFIFTEFLEPAANETVRHGCLRLNQ
PTHVNNGNYTLLAANPFGQASASIMAAFMDNPFEFNPEDPIPVSFSPVDT
NSTSGDPVEKKDETPFGVSVAVGLAVFACLFLSTLLLVLNKCGRRNKFGI
NRPAVLAPEDGLAMSLHFMTLGGSSLSPTEGKGSGLQGHIIENPQYFSDA
CVHHIKRRDIVLKWELGEGAFGKVFLAECHNLLPEQDKMLVAVKALKEAS
ESARQDFQREAELLTMLQHQHIVRFFGVCTEGRPLLMVFEYMRHGDLNRF
LRSHGPDAKLLAGGEDVAPGPLGLGQLLAVASQVAAGMVYLAGLHFVHRD
LATRNCLVGQGLVVKIGDFGMSRDIYSTDYYRVGGRTMLPIRWMPPESIL
YRKFTTESDVWSFGVVLWEIFTYGKQPWYQLSNTEAIDCITQGRELERPR
ACPPEVYAIMRGCWQREPQQRHSIKDVHARLQALAQAPPVYLDVLG.
```

The following nucleotide sequence was reported as the mRNA for rat TrkA receptor and is accession number M85214 in Genbank.

```
                                          (SEQ ID NO: 5)
gcggcggcgg ccaggagcgc acggacggcc gcgcggcccg
agctaggcgg gcgccgccgc gatgctgcga ggccagcggc
acgggcagct gggttggcat cgcccggccg cggggctagg
cggtctggtg acttcgttga tgctggcttg tgcttgcgcc
gcatcctgtc gtgagacctg ctgtcccgtg ggccctcgg
ggttgcgctg caccagggca gggaccctga ataccctccg
cggcctgcgg ggcgccggga acctgacgga gctctatgtg
gaaaaccagc gggatctgca acgcctggag tttgaggacc
tgcagggcct gggggagttg agaagcctaa ccatcgtgaa
gagtggcctc cgctttgtgg ccctgatgc cttccatttc
accctcggc tcagtcacct gaatctctcc tccaatgctt
tggagtccct ctcctggaaa actgtgcagg gcctctccct
acaggacttg accctgtcag ggaacccact gcactgttcc
tgtgccctat tgtggctcca gcgctgggag caggaggatt
tgtgtggtgt gtatacacaa aagcttcagg gctctgggtc
tggagaccag ttcctcccac tgggacacaa caacagttgt
ggtgtaccct cagtgaagat ccagatgccc aatgactctg
tggaagtggg ggatgacgtt tttctgcagt gccaggtgga
ggggcaggcc ctacagcagg ctgactggat cctcacagag
ctggaaggga cagccaccat gaagaaatct ggagatctgc
catccctggg gctaactctg tcaatgtca ccagtgatct
caacaagaag aatgtgacgt gctgggcaga gaatgatgtg
ggccgggctg aggtctctgt ccaagtcagc gtctccttcc
cagccagtgt gcatctgggc aaagccgtgg aacagcatca
ctggtgcatt cccttctctg tggacgggca gccagcaccg
tccctgcgct ggttcttcaa cggctctgtg ctcaatgaga
ccagcttcat cttcactcag ttcttggagt cagcgctgac
caatgagacc atgcggcatg gctgccttcg cctcaaccag
cccacgcatg tcaacaacgg gaactacacc ctgctggctg
ccaaccccta tggccaggct gctgcctcca tcatggctgc
ctttatggac aaccctttg agttcaaccc tgaggacccc
atccctgtct ccttctcgcc agtggacact aacagcacat
caagagaccc agtggagaag aaggacgaaa ccctttggg
ggtctctgtg gctgtgggcc tggccgtctc cgccgccctc
ttcctttctg ccctcctcct agtgctcaac aaatgtggac
```

```
agaggagcaa atttgggatc aaccgccctg ctgtgctggc gccagaggat gggctggcca tgtccctaca cttcatgaca ctgggtggca gttctctttc ccctactgag ggcaaaggct ccggactcca gggccacatc atggagaacc cacagtactt cagtgatacc tgtgtccacc atatcaagcg ccaggacatc attctcaagt gggagctagg ggagggagcc tttggaaagg tctttcttgc tgagtgctac aaccttctga atgatcagga caagatgctg gtggctgtca aggcactgaa ggagacatct gagaatgctc gtcaggactt ccatcgtgag gcagagctgc tcaccatgct acagcaccaa cacatcgtac gcttctttgg agtctgcacg gagggtggcc cattgctcat ggtcttcgag tacatgcgcc atggggacct caaccgtttc ctccggtccc acggacctga tgcaaaactg ctggctggcg gcgaggatgt ggctcctggt cctttgggcc ttgggcagct tctggctgtg gctagccagg tggctgctgg tatggtgtac ctagccagcc tgcactttgt gcaccgggac ctggccacac gcaactgtct ggtgggtcag ggactagtgg tcaagattgg agacttcggc atgagcaggg acatctacac cacagactac taccgtgtgg gaggtcggac catgctgccc atccgctgga tgcctccaga gagcatcctc taccgcaagt tcagcaccga gagtgatgtg tggagcttcg gggtggtgct ctgggagatc ttcacctatg gaaagcaacc ctggtaccag ctctccaaca ctgaggcgat cgagtgcatc acgcagggcc gggagctgga gcggccgcgc gcctgccctc ctgatgtcta cgccatcatg cgcggctgct ggcagcgtga gccgcaacag cgcctcagca tgaaggatgt gcacgcgcgg ctgcaggcct tggcacaggc gccaccgagt tacctggacg ttctgggcta ggagtctgga tgtcaggcta ccctgggctc cctcagcgcc cagcagctat cacactcaag tcttaccctc agcatgtgga ggggaccagc aggcggggag cagagggtgg ctttgcttca tggccagcat ccatcataat agcaattata tttattatcc ctgaaaaaaa aaa
```

The following polypeptide sequence was reported as the rat TrkA polypeptide sequence (799 amino acids) and has the accession number P35739 in Genbank.

```
                                    (SEQ ID NO: 6)
mlrgqrhgql gwhrpaaglg glvtslmlac acaascretc cpvgpsglrc tragtlntlr glrgagnlte lyvenqrdlq rlefedlqgl gelrsltivk sglrfvapda fhftprlshl nlssnalesl swktvqglsl qdltlsgnpl hcscallwlq rweqedlcgv ytqklqgsgs gdqflplghn nscgvpsvki qmpndsvevg ddvflqcqve gqalqqadwi ltelegtatm kksgdlpslg ltlvnvtsdl nkknvtcwae ndvgraevsv qvsvsfpasv hlgkaveqhh wcipfsvdgq papslrwffn gsvlnetsfi ftqflesalt netmrhgclr lnqpthvnng nytllaanpy gqaaasimaa fmdnpfefnp edpipvsfsp vdtnstsrdp vekkdetpfg vsvavglavs aalflsalll vlnkcgqrsk fginrpavla pedglamslh fmtlggssls ptegkgsglq ghimenpqyf sdtcvhhikr qdiilkwelg egafgkvfla ecynllndqd kmlvavkalk etsenarqdf hreaelltml qhqhivrffg vcteggpllm vfeymrhgdl nrflrshgpd akllaggedv apgplglgql lavasqvaag mvylaslhfv hrdlatrncl vgqglvvkig dfgmsrdiys tdyyrvggrt mlpirwmppe silyrkfste sdvwsfgvvl weiftygkqp wyqlsnteai ecitqgrele rpracppdvy aimrgcwqre pqqrlsmkdv harlqalaqa ppsyldvlg
```

Table 2 lists the TrkA domains and other regions, according to amino acid residue number, based on SEQ ID NO:4. As one of skill in the art will appreciate, the beginning and ending residues of the domains listed below may vary depending upon the computer modeling program used or the method used for determining the domain.

TABLE 2

| Domain or Region | Beginning Residue | Ending Residue |
|---|---|---|
| Signal Peptide | 1 | 32 |
| Cysteine-rich 1 | 36 | 68 |
| LRR1 | 90 | 113 |
| LLR2 | 115 | 137-140 |
| Cysteine-rich 2 | 141 | 192 |
| Ig-Like 1 | 194-211 | 269-283 |
| Ig-Like 2 | 299 | 365 |
| Transmembrane | 408-424 | 433-439 |
| Tyrosine Kinase Catalytic Domain | 510 | 775-781 |

Methods Using Antagonists of TrkA or Sp35

One embodiment of the present invention provides methods for promoting myelination of CNS neurons comprising contacting a mixture of CNS neurons and oligodendrocytes with an effective amount of a TrkA antagonist. A TrkA antagonist for the purposes of the methods of the present invention may be any molecule which relieves the inhibition of CNS myelination and/or promotes CNS neuronal cell survival and/or decreases or inhibits Sp35 expression. TrkA antagonists for use in the methods of the present invention are selected from the group consisting of a TrkA antagonist compound, a TrkA antagonist polypeptide, a TrkA antibody, a TrkA antagonist polynucleotide, a TrkA aptamer, and a combination of two or more of said TrkA antagonists.

Further embodiments of the invention include a method of promoting myelination of CNS neurons in a mammal comprising administering to a mammal, in need thereof, an effective amount of a composition comprising a TrkA antagonist selected from the group consisting of a TrkA antagonist compound, a TrkA antagonist polypeptide, a TrkA antibody, a TrkA antagonist polynucleotide, a TrkA aptamer, and a combination of two or more of said TrkA antagonists.

Other embodiments of the invention include methods for promoting oligodendrocyte differentiation by contacting oligodendrocytes or oligodendrocyte precursor cells with an effective amount of a TrkA antagonist selected from the group consisting of a TrkA antagonist compound, a TrkA antagonist polypeptide, a TrkA antibody, a TrkA antagonist polynucleotide, a TrkA aptamer, and a combination of two or more of said TrkA antagonists. In certain embodiments, soluble TrkA antagonist polypeptides for use in methods for promoting oligodendrocyte differentiation do not include soluble TrkA antagonist polypeptides comprising the entire extracellular domain of TrkA. Additionally, in certain embodiments, soluble TrkA antagonist polypeptides for use in methods for promoting oligodendrocyte differentiation do not include soluble TrkA antagonist polypeptides which comprise amino acids 1-$X_2$ of SEQ ID NO:4, where $X_2$ can be 405 to 423, or amino acids 1-405 of SEQ ID NO:6. Additionally, in certain embodiments, soluble TrkA antagonist polypeptides for use in methods for promoting oligodendrocyte differentiation do not include soluble TrkA antagonist polypeptides which comprise amino acids 1-$X_2$ of SEQ ID NO:4, where $X_2$ can be 405 to 423, or amino acids 1-405 of SEQ ID NO:6 and wherein said soluble TrkA antagonist polypeptide is fused to an Fc moiety.

An additional embodiment of the present invention provides methods for treating a disease, disorder or injury associated with dysmyelination or demyelination, (e.g., Multiple Sclerosis) in an animal (e.g. a mammal) suffering from such disease, the method comprising, consisting essentially of, or consisting of administering to the mammal in need thereof a therapeutically effective amount of a TrkA antagonist wherein the TrkA antagonist is selected from the group consisting of a TrkA antagonist compound, a TrkA antagonist polypeptide, a TrkA antibody, a TrkA antagonist polynucleotide, a TrkA aptamer, and a combination of two or more of said TrkA antagonists.

Other embodiments of the invention include methods for promoting survival of CNS neurons in a mammal in need thereof comprising administering an effective amount of a composition comprising a TrkA antagonist wherein the TrkA antagonist is selected from the group consisting of a TrkA antagonist compound, a TrkA antagonist polypeptide, a TrkA antibody, a TrkA antagonist polynucleotide, a TrkA aptamer, and a combination of two or more of said TrkA antagonists.

Further embodiments of the invention include methods for promoting oligodendrocyte differentiation in a mammal, comprising administering to a mammal in need thereof an effective amount of a composition comprising a TrkA antagonist selected from the group consisting of a TrkA antagonist compound, a TrkA antagonist polypeptide, a TrkA antibody, a TrkA antagonist polynucleotide, a TrkA aptamer, and a combination of two or more of said TrkA antagonists. In certain embodiments, soluble TrkA antagonist polypeptides for use in methods for promoting oligodendrocyte differentiation do not include soluble TrkA antagonist polypeptides comprising the entire extracellular domain of TrkA. Additionally, in certain embodiments, soluble TrkA antagonist polypeptides for use in methods for promoting oligodendrocyte differentiation do not include soluble TrkA antagonist polypeptides which comprise amino acids 1-$X_2$ of SEQ ID NO:4, where $X_2$ can be 405 to 423, or amino acids 1-405 of SEQ ID NO:6. Additionally, in certain embodiments, soluble TrkA antagonist polypeptides for use in methods for promoting oligodendrocyte differentiation do not include soluble TrkA antagonist polypeptides which comprise amino acids 1-$X_2$ of SEQ ID NO:4, where $X_2$ can be 405 to 423, or amino acids 1-405 of SEQ ID NO:6 and wherein said soluble TrkA antagonist polypeptide is fused to an Fc moiety.

Additional embodiments of the invention include methods for decreasing or inhibiting Sp35 expression, relative to Sp35 expression in the absence of a TrkA inhibitor, comprising contacting CNS neurons with a composition comprising a TrkA antagonist wherein the TrkA antagonist is selected from the group consisting of a TrkA antagonist compound, a TrkA antagonist polypeptide, a TrkA antibody, a TrkA antagonist polynucleotide, a TrkA aptamer, and a combination of two or more of said TrkA antagonists.

Further embodiments of the invention include methods for blocking Sp35 and TrkA interaction comprising contacting a mixture of neurons and oligodendrocytes with a composition comprising an Sp35 antagonist wherein the Sp35 antagonist is selected from the group consisting of a soluble Sp35 polypeptide, an Sp35 antibody, an Sp35 antagonist polynucleotide, an Sp35 aptamer, and a combination of two or more of said Sp35 antagonists.

Additional embodiments of the invention include methods for inhibiting or decreasing TrkA phosphorylation, relative to TrkA phosphorylation in the absence of a TrkA inhibitor comprising contacting CNS neurons with a composition comprising an Sp35 antagonist wherein the Sp35 antagonist is selected from the group consisting of a soluble Sp35 polypeptide, an Sp35 antibody, an Sp35 antagonist polynucleotide, an Sp35 aptamer, and a combination of two or more of said Sp35 antagonists In methods of the present invention, an Sp35 or TrkA antagonist can be administered via direct administration of a soluble Sp35 or TrkA antagonist polypeptide, Sp35 or TrkA antibody, Sp35 or TrkA antagonist polynucleotide, Sp35 or TrkA aptamer, or combinations thereof to the patient. Alternatively, the Sp35 or TrkA antagonist can be administered via an expression vector which produces the specific Sp35 or TrkA antagonist.

In certain embodiments of the invention, an Sp35 or TrkA antagonist is administered in a method that includes: (1) transforming or transfecting an implantable host cell with a nucleic acid, e.g., a vector, that expresses an Sp35 or TrkA antagonist; and (2) implanting the transformed host cell into a mammal, at the site of a disease, disorder or injury. For example, the transformed host cell can be implanted at certain affected sites (e.g. the transformed host cell can be implanted at the site of a chronic lesion of MS). In some embodiments of the invention, the implantable host cell is removed from a mammal, temporarily cultured, transformed or transfected with an isolated nucleic acid encoding an Sp35 or TrkA antagonist, and implanted back into the same mammal from which it was removed. The cell can be, but is not required to be, removed from the same site at which it is implanted. Such embodiments, sometimes known as ex vivo gene therapy, can provide a continuous supply of the Sp35 or TrkA antagonist, localized at the site of action, for a limited period of time.

Diseases or disorders which may be treated or ameliorated by the methods of the present invention include diseases, disorders or injuries which relate to dysmyelination or demyelination of CNS neurons. Such diseases include, but are not limited to, diseases and disorders in which the myelin which surrounds the neuron is either absent, incomplete, not formed properly or is deteriorating. Such disease include, but are not limited to, multiple sclerosis (MS), progressive multifocal leukoencephalopathy (PML), encephalomyelitis (EPL), central pontine myelolysis (CPM), adrenoleukodystrophy, Alexander's disease, Pelizaeus Merzbacher disease (PMZ), Wallerian Degeneration, optic neuritis, transverse myelitis, amylotrophic lateral sclerosis (ALS), Huntington's disease, Alzheimer's disease, Parkinson's disease, spinal cord injury, traumatic brain injury, post radiation injury, neurologic complications of chemotherapy, stroke, acute ischemic optic neuropathy, vitamin E deficiency, isolated vitamin E deficiency syndrome, AR, Bassen-Kornzweig syndrome, Marchiafava-Bignami syndrome, metachromatic leukodystrophy, trigeminal neuralgia, acute dissmeminated encephalitis, Guillian-Barre syndrome, Marie-Charcot-Tooth disease and Bell's palsy.

A TrkA antagonist, e.g., a TrkA antagonist compound, an antagonist TrkA polypeptide, a TrkA antibody, a TrkA antagonist polynucleotide, or a TrkA aptamer, to be used in methods disclosed herein, can be prepared and used as a therapeutic agent that stops, reduces, prevents, or inhibits the ability of TrkA to negatively regulate myelination and/or neuronal survival and/or increase Sp35 expression.

An Sp35 antagonist, e.g., a soluble Sp35, an Sp35 antibody, an Sp35 antagonist polynucleotide, or an Sp35 aptamer, to be used in methods disclosed herein, can be prepared and used as a therapeutic agent that stops, reduces, prevents, or inhibits the ability of Sp35 to interact with TrkA and/or stops, reduces, prevents, or inhibits TrkA phosphorylation.

TrkA Antagonist Compounds

TrkA antagonists in the methods of the present invention include a TrkA compound antagonist which comprises any chemical or synthetic compound which inhibits or reduces the activity of TrkA or inhibits or reduces the phosphorylation of TrkA when compared to the state of TrkA in the absence of the antagonist compound.

TrkA antagonist compounds include, but are not limited to, K252a and derivatives there of as described in U.S. Pat. No. 5,468,872, which is incorporated herein by reference in its entirety; lidocaine [137-58-6]; bupivacaine 2180-92-9]; procaine [59-46-1]; 1H-[1,2,4]oxadiazolo[4,3-α]quinoxalin-1-one (ODQ) [41443-28-1]; methylmercury [22967-92-6]; endocannabanoid anandamide; CEP-701 [111358-88-4]; CEP-751 (KT-6587); PD098059 [167869-21-8]; Tamoxifen [10540-29-1]; Tunicamycin [11089-65-9]; 3-morpholino-syndnomine (Sin-1) [16142-27-1]; Tryphostin AG879 [148741-30-4]; herbimycin A [70563-58-5]; genistein [446-72-0]; 5-azacytidine [320-67-1]; and tryphostin RG508964 or tryphostin RG50872 [10537-47-0].

One of ordinary skill in the art would know how to screen and test for other TrkA compounds which would be useful in the methods of the present invention.

Soluble Sp35 and Antagonist TrkA Polypeptides

Soluble Sp35 Polypeptides

Sp35 antagonists to be used in the methods of the present invention include those polypeptides which block, inhibit or interfere with the biological function of naturally occurring Sp35. Specifically, soluble Sp35 polypeptides of the present invention include fragments, variants, or derivative thereof of a soluble Sp35 polypeptide. Table 1 above describes the various domains of the Sp35 polypeptide. Soluble Sp35 polypeptides lack the transmembrane domain and typically lack the intracellular domain of the Sp35 polypeptide. For example, certain soluble Sp35 polypeptides lack amino acids 552-576 which comprise the transmembrane domain of Sp35 and/or amino acids 577-614 which comprise the intracellular domain of Sp35. Additionally, certain soluble Sp35 polypeptides comprise the LRR domains, Ig domain, basic region and/or the entire extracellular domain (corresponding to amino acids 34 to 532 of SEQ ID NO: 2) of the Sp35 polypeptide. As one of skill in the art would appreciate, the entire extracellular domain of Sp35 may comprise additional or fewer amino acids on either the C-terminal or N-terminal end of the extracellular domain polypeptide.

As such, soluble Sp35 polypeptides for use in the methods of the present invention include, but are not limited to, an Sp35 polypeptide comprising, consisting essentially of, or consisting of amino acids 41 to 525 of SEQ ID NO:2; 40 to 526 of SEQ ID NO:2; 39 to 527 of SEQ ID NO:2; 38 to 528 of SEQ ID NO:2; 37 to 529 of SEQ ID NO:2; 36 to 530 of SEQ ID NO:2; 35 to 531 of SEQ ID NO:2; 34 to 531 of SEQ ID NO:2; 46 to 520 of SEQ ID NO:2; 45 to 521 of SEQ ID NO:2; 44 to 522 of SEQ ID NO:2; 43 to 523 of SEQ ID NO:2; and 42 to 524 of SEQ ID NO:2 or fragments, variants, or derivatives of such polypeptides. Sp35 polypeptide antagonists may include any combination of domains as described in Table 1.

Additional soluble Sp35 polypeptides for use in the methods of the present invention include, but are not limited to, an Sp35 polypeptide comprising, consisting essentially of, or consisting of amino acids 1 to 33 of SEQ ID NO:2; 1 to 35 of SEQ ID NO:2; 34 to 64 of SEQ ID NO:2; 36 to 64 of SEQ ID NO:2; 66 to 89 of SEQ ID NO:2; 90 to 113 of SEQ ID NO:2; 114 to 137 of SEQ ID NO:2; 138 to 161 of SEQ ID NO:2; 162 to 185 of SEQ ID NO:2; 186 to 209 of SEQ ID NO:2; 210 to 233 of SEQ ID NO:2; 234 to 257 of SEQ ID NO:2; 258 to 281 of SEQ ID NO:2; 282 to 305 of SEQ ID NO:2; 306 to 329 of SEQ ID NO:2; 330 to 353 of SEQ ID NO:2; 363 to 416 of SEQ ID NO:2; 417 to 424 of SEQ ID NO:2; 419 to 493 of SEQ ID NO:2; and 494 to 551 of SEQ ID NO:2 or fragments, variants, or derivatives of such polypeptides.

Further soluble Sp35 polypeptides for use in the methods of the present invention include, but are not limited to, an Sp35 polypeptide comprising, consisting essentially of, or consisting of amino acids 1 to 33 of SEQ ID NO:2; 1 to 35 of SEQ ID NO:2; 1 to 64 of SEQ ID NO:2; 1 to 89 of SEQ ID NO:2; 1 to 113 of SEQ ID NO:2; 1 to 137 of SEQ ID NO:2; 1 to 161 of SEQ ID NO:2; 1 to 185 of SEQ ID NO:2; 1 to 209 of SEQ ID NO:2; 1 to 233 of SEQ ID NO:2; 1 to 257 of SEQ ID NO:2; 1 to 281 of SEQ ID NO:2; 1 to 305 of SEQ ID NO:2; 1 to 329 of SEQ ID NO:2; 1 to 353 of SEQ ID NO:2; 1 to 416 of SEQ ID NO:2; 1 to 424 of SEQ ID NO:2; 1 to 493 of SEQ ID NO:2; 1 to 551 of SEQ ID NO:2; 1 to 531 of SEQ ID NO:2 and 1 to 532 of SEQ ID NO:2 or fragments, variants, or derivatives of such polypeptides.

Still further soluble Sp35 polypeptides for use in the methods of the present invention include, but are not limited to, an Sp35 polypeptide comprising, consisting essentially of, or consisting of amino acids 34 to 64 of SEQ ID NO:2; 34 to 89 of SEQ ID NO:2; 34 to 113 of SEQ ID NO:2; 34 to 137 of SEQ ID NO:2; 34 to 161 of SEQ ID NO:2; 34 to 185 of SEQ ID NO:2; 34 to 209 of SEQ ID NO:2; 34 to 233 of SEQ ID NO:2; 34 to 257 of SEQ ID NO:2; 34 to 281 of SEQ ID NO:2; 34 to 305 of SEQ ID NO:2; 34 to 329 of SEQ ID NO:2; 34 to 353 of SEQ ID NO:2; 34 to 416 of SEQ ID NO:2; 34 to 424 of SEQ ID NO:2; 34 to 493 of SEQ ID NO:2; and 34 to 551 of SEQ ID NO:2 or fragments, variants, or derivatives of such polypeptides.

Additional soluble Sp35 polypeptides for use in the methods of the present invention include, but are not limited to, an Sp35 polypeptide comprising, consisting essentially of, or consisting of amino acids 34 to 530 of SEQ ID NO:2; 34 to 531 of SEQ ID NO:2; 34 to 532 of SEQ ID NO:2; 34 to 533 of SEQ ID NO:2; 34 to 534 of SEQ ID NO:2; 34 to 535 of SEQ ID NO:2; 34 to 536 of SEQ ID NO:2; 34 to 537 of SEQ ID NO:2; 34 to 538 of SEQ ID NO:2; 34 to 539 of SEQ ID NO:2; 30 to 532 of SEQ ID NO:2; 31 to 532 of SEQ ID NO:2; 32 to 532 of SEQ ID NO:2; 33 to 532 of SEQ ID NO:2; 34 to 532 of SEQ ID NO:2; 35 to 532 of SEQ ID NO:2; 36 to 532 of SEQ ID NO:2; 30 to 531 of SEQ ID NO:2; 31 to 531 of SEQ ID NO:2; 32 to 531 of SEQ ID NO:2; 33 to 531 of SEQ ID NO:2; 34 to 531 of SEQ ID NO:2; 35 to 531 of SEQ ID NO:2; and 36 to 531 of SEQ ID NO:2 or fragments, variants, or derivatives of such polypeptides.

Still further soluble Sp35 polypeptides for use in the methods of the present invention include, but are not limited to, an Sp35 polypeptide comprising, consisting essentially of, or consisting of amino acids 36 to 64 of SEQ ID NO:2; 36 to 89 of SEQ ID NO:2; 36 to 113 of SEQ ID NO:2; 36 to 137 of SEQ ID NO:2; 36 to 161 of SEQ ID NO:2; 36 to 185 of SEQ ID NO:2; 36 to 209 of SEQ ID NO:2; 36 to 233 of SEQ ID NO:2; 36 to 257 of SEQ ID NO:2; 36 to 281 of SEQ ID NO:2; 36 to 305 of SEQ ID NO:2; 36 to 329 of SEQ ID NO:2; 36 to 353 of SEQ ID NO:2; 36 to 416 of SEQ ID NO:2; 36 to 424 of SEQ ID NO:2; 36 to 493 of SEQ ID NO:2; and 36 to 551 of SEQ ID NO:2 or fragments, variants, or derivatives of such polypeptides.

Additional soluble Sp35 polypeptides for use in the methods of the present invention include, but are not limited to, an Sp35 polypeptide comprising, consisting essentially of, or consisting of amino acids 36 to 530 of SEQ ID NO:2; 36 to 531 of SEQ ID NO:2; 36 to 532 of SEQ ID NO:2; 36 to 533 of SEQ ID NO:2; 36 to 534 of SEQ ID NO:2; 36 to 535 of SEQ ID NO:2; 36 to 536 of SEQ ID NO:2; 36 to 537 of SEQ ID NO:2; 36 to 538 of SEQ ID NO:2; and 36 to 539 of SEQ ID NO:2; or fragments, variants, or derivatives of such polypeptides.

Additional soluble Sp35 polypeptides, fragments, variants or derivatives thereof include polypeptides comprising the Ig domain of Sp35. For example, an Sp35 polypeptide comprising, consisting essentially of, or consisting of amino acids 417 to 493 of SEQ ID NO:2; 417 to 494 of SEQ ID NO:2; 417 to 495 of SEQ ID NO:2; 417 to 496 of SEQ ID NO:2; 417 to 497 of SEQ ID NO:2; 417 to 498 of SEQ ID NO:2; 417 to 499 of SEQ ID NO:2; 417 to 500 of SEQ ID NO:2; 417 to 492 of SEQ ID NO:2; 417 to 491 of SEQ ID NO:2; 412 to 493 of SEQ ID NO:2; 413 to 493 of SEQ ID NO:2; 414 to 493 of SEQ ID NO:2; 415 to 493 of SEQ ID NO:2; 416 to 493 of SEQ ID NO:2; 411 to 493 of SEQ ID NO:2; 410 to 493 of SEQ ID NO:2; 410 to 494 of SEQ ID NO:2; 411 to 494 of SEQ ID NO:2; 412 to 494 of SEQ ID NO:2; 413 to 494 of SEQ ID NO:2; 414 to 494 of SEQ ID NO:2; 415 to 494 of SEQ ID NO:2; 416 to 494 of SEQ ID NO:2; 417 to 494 of SEQ ID NO:2; and 418 to 494 of SEQ ID NO:2 or fragments, variants, or derivatives of such polypeptides.

Soluble Sp35 polypeptides for use in the methods of the present invention also includes two or more soluble Sp35 polypeptides disclosed herein. The two or more soluble Sp35 polypeptides for use in the methods of the invention may be fused together to form a single polypeptide comprising multiple Sp35 soluble polypeptides disclosed herein or may be individual soluble Sp35 polypeptides comprising a composition for use in the methods of the present invention.

Various exemplary soluble Sp35 polypeptides and methods and materials for obtaining these molecules for practicing the present invention are described below and/or may be found, e.g., in International Patent Application No. PCT/US2004/008323, PCT Publication No. WO2004/085648, and U.S. Published Application No. 2006/017673, which are incorporated herein by reference in their entireties.

TrkA Antagonist Polypeptides

TrkA antagonist polypeptides for use in the methods of the present invention include any polypeptide which would block, inhibit, interfere or reduce the activity of TrkA. Such proteins include but are not limited to PTEN; SHP-1; pregnancy zone protein; human alpha (2)-macroglobulin (alpha 2m); methylamine-activated alpha 2M (MA-alpha 2M); seratonin-activated alpha 2M (5HT-alpha 2M); Pertussis toxin; the protein produced by the myc myelocytomatesis viral related oncogene (MYCN); and Caveolin. Additionally, TrkA antagonist polypeptides for use in the methods of the present invention include, but are not limited to TrkA polypeptides, including soluble polypeptides.

Specifically, soluble TrkA polypeptides for use in the methods of the present invention include fragments, variants, or derivative thereof of a soluble TrkA polypeptide. Table 2 above describes the various domains of the TrkA polypeptide. Soluble TrkA polypeptides lack the transmembrane domain and typically lack the intracellular domain of the TrkA polypeptide. For example, certain soluble TrkA polypeptides lack amino acids 408-433, 408-439, 424-433 or 424-439 of SEQ ID NO:4 which comprise the transmembrane domain of TrkA and/or amino acids 434-796 or 440-796 of SEQ ID NO:4 which comprise the intracellular domain of TrkA. Additionally, certain soluble TrkA polypeptides comprise a Cysteine Cluster (CCI and/or CCII), a leucine-rich motif and/or one or more leucine rich repeats, an Ig domain (IgI and/or IgII), and/or a portion of or the entire extracellular domain (corresponding to amino acids 36 to 423 or 36 to 407 of SEQ ID NO:4), of the TrkA polypeptide. As one of skill in the art would appreciate, the extracellular domain of TrkA may comprise additional or fewer amino acids on either the C-terminal or N-terminal end of the extracellular domain polypeptide.

In certain embodiments, soluble TrkA antagonist polypeptides for use in methods for promoting oligodendrocyte differentiation do not include soluble TrkA antagonist polypeptides comprising the entire extracellular domain of TrkA. Additionally, in certain embodiments, soluble TrkA antagonist polypeptides for use in methods for promoting oligodendrocyte differentiation do not include soluble TrkA antagonist polypeptides which comprise amino acids 1-X2 of SEQ ID NO:4, where X2 can be 405 to 423, or amino acids 1-405 of SEQ ID NO:6. Additionally, in certain embodiments, soluble TrkA antagonist polypeptides for use in methods for promoting oligodendrocyte differentiation do not include soluble TrkA antagonist polypeptides which comprise amino acids 1-X2 of SEQ ID NO:4, where X2 can be 405 to 423, or amino acids 1-405 of SEQ ID NO:6 and wherein said soluble TrkA antagonist polypeptide is fused to an Fc moiety.

Soluble TrkA polypeptides for use in the methods of the present invention include, but are not limited to, a TrkA polypeptide comprising, consisting essentially of, or consisting of amino acids X to Y of SEQ ID NO:4, wherein X is amino acids 1 to 40 of SEQ ID NO:4 and Y is amino acids 60 to 450 of SEQ ID NO:4 or fragments, variants, or derivatives of such polypeptides. In certain embodiments of the present invention a TrkA polypeptide for use in methods for promoting oligodendrocyte differentiation comprising, consisting essentially of, or consisting of amino acids X to Y of SEQ ID NO:4, wherein X is amino acids 1 to 40 of SEQ ID NO:4 and Y is amino acids 60 to 450 of SEQ ID NO:4 does not include amino acids 1 to 405 of SEQ ID NO:4.

Soluble TrkA polypeptides for use in the methods of the present invention include, but are not limited to, a TrkA polypeptide comprising, consisting essentially of, or consisting of amino acids 36 to 68 of SEQ ID NO:4; 90 to 113 of SEQ ID NO:4; 115 to 137 of SEQ ID NO:4, 90 to 137 of SEQ ID NO:4; 141 to 192 of SEQ ID NO:4; 211 to 269 of SEQ ID NO:4; 211 to 283 of SEQ ID NO:4, 194 to 269 of SEQ ID NO:4, 194 to 283 of SEQ ID NO:4, 299 to 365 of SEQ ID NO:4; 366 to 407 of SEQ ID NO:4; 366 to 424 of SEQ ID NO:4 or fragments, variants, or derivatives of such polypeptides. TrkA polypeptide antagonists may include any combination of domains as described in Table 2.

Additional soluble TrkA polypeptides, fragments, variants or derivatives thereof for use in the methods of the present invention include, but are not limited to, a TrkA polypeptide comprising, consisting essentially of, or consisting of amino acids 1 to 68 of SEQ ID NO:4; 1 to 113 of SEQ ID NO:4, 1 to 137 of SEQ ID NO:4, 1 to 140 of SEQ ID NO:4; 1 to 192 of SEQ ID NO:4; 1 to 269 of SEQ ID NO:4; 1 to 283 of SEQ ID NO:4, 1 to 365 of SEQ ID NO:4; 1 to 407 of SEQ ID NO:4; 1 to 441 of SEQ ID NO:4; 1 to 439 of SEQ ID NO:4, 36 to 68 of SEQ ID NO:4; 36 to 113 of SEQ ID NO:4, 36 to 137 of SEQ ID NO:4, 36 to 140 of SEQ ID NO:4; 36 to 192 of SEQ ID NO:4, 36 to 269 of SEQ ID NO:4; 36 to 283 of SEQ ID NO:4, 36 to 365 of SEQ ID NO:4; 36 to 407 of SEQ ID NO:4; 36 to 439 of SEQ ID NO:4 or fragments, variants, or derivatives of such polypeptides.

Additional soluble TrkA polypeptides, fragments, variants or derivatives thereof include polypeptides comprising one or more of the Ig domains of TrkA. For example, an TrkA polypeptide comprising, consisting essentially of, or consisting of amino acids 194 to 269 of SEQ ID NO:4; 194 to 283 of SEQ ID NO:4, 211 to 269 of SEQ ID NO:4; 211 to 283 of SEQ ID NO:4; 299 to 365 of SEQ ID NO:4; 194 to 365 of SEQ ID NO:4; or 211 to 365 of SEQ ID NO:4; or fragments, variants, or derivatives of such polypeptides.

Additional TrkA polypeptides, fragments, variants or derivatives thereof for use in the methods of the present invention include, but are not limited to a TrkA polypeptide comprising, consisting essentially of, or consisting of the extracellular domain and a portion of or the entire transmembrane domain. For example, a TrkA polypeptide comprising, consisting essentially of, or consisting of amino acids X1 to Y1 of SEQ ID NO:4, wherein X1 is amino acid 1 to 36 of SEQ ID NO:4 and Y1 is amino acids 360 to 445 or fragments, variants, or derivatives of such polypeptides (e.g. amino acids 1 to 441 of SEQ ID NO:4 or 36 to 441 of SEQ ID NO:4).

Additional TrkA polypeptides, fragments, variants or derivatives thereof for use in the methods of the present invention include, but are not limited to a TrkA polypeptide comprising, consisting essentially of, or consisting of the full-length TrkA protein (either the 790 amino acid form or the 796 amino acid form of SEQ ID NO:4) fused to an immunoglobulin domain. For example, a TrkA polypeptide comprising, consisting essentially of, or consisting of amino acids 1 to 796 of SEQ ID NO:4; 36 to 796 of SEQ ID NO:4 fused to an IgG domain. Additional TrkA polypeptides, fragments, variants or derivatives thereof described herein may also be fused to an immunoglobulin domain.

Additional TrkA antagonist polypeptides for use in the methods of the present invention also includes two or more TrkA antagonist polypeptides disclosed herein. The two or more TrkA antagonist polypeptides for use in the methods of the invention may be fused together to form a single polypeptide comprising multiple TrkA antagonist polypeptides disclosed herein or may be individual TrkA antagonist polypeptides comprising a composition for use in the methods of the present invention.

Soluble Sp35 and TrkA polypeptides for use in the methods of the present invention described herein may be cyclic. Cyclization of the soluble Sp35 or TrkA polypeptides reduces the conformational freedom of linear peptides and results in a more structurally constrained molecule. Many methods of peptide cyclization are known in the art, for example, "backbone to backbone" cyclization by the formation of an amide bond between the N-terminal and the C-terminal amino acid residues of the peptide. The "backbone to backbone" cyclization method includes the formation of disulfide bridges between two ω-thio amino acid residues (e.g. cysteine, homocysteine). Certain soluble Sp35 or TrkA peptides of the present invention include modifications on the N- and C-terminus of the peptide to form a cyclic Sp35 or TrkA polypeptide. Such modifications include, but are not limited to, cysteine residues, acetylated cysteine residues, cysteine residues with a NH2 moiety and biotin. Other methods of peptide cyclization are described in Li & Roller, Curr. Top. Med. Chem. 3:325-341 (2002), which is incorporated by reference herein in its entirety.

Soluble Sp35 or antagonist TrkA polypeptides described herein may have various alterations such as substitutions, insertions or deletions. For examples, substitutions include, but are not limited to the following substitutions: valine at position 6 of the Sp35 polypeptide of SEQ ID NO:2 to methionine; serine at position 294 of the Sp35 polypeptide of SEQ ID NO:2 to glycine; valine at position 348 of the Sp35 polypeptide of SEQ ID NO:2 to alanine; arginine at position 419 of the Sp35 polypeptide to histidine; arginine at position 456 to glutamic acid; and histidine at position 458 of SEQ ID NO:2 to valine.

Corresponding fragments of soluble Sp35 or antagonist TrkA polypeptides at least 70%, 75%, 80%, 85%, 90%, or 95% identical to polypeptides of SEQ ID NO:2 or SEQ ID NO:4 described herein are also contemplated.

As known in the art, "sequence identity" between two polypeptides is determined by comparing the amino acid sequence of one polypeptide to the sequence of a second polypeptide. When discussed herein, whether any particular polypeptide is at least about 70%, 75%, 80%, 85%, 90% or 95% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, Advances in Applied Mathematics 2:482-489 (1981), to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full length of the reference polypeptide sequence and that gaps in homology of up to 5% of the total number of amino acids in the reference sequence are allowed.

Soluble Sp35 or antagonist TrkA polypeptides for use in the methods of the present invention may include any combination of two or more soluble Sp35 or antagonist TrkA polypeptides.

Antibodies or Antigen-Binding Fragments Thereof

In one embodiment, an Sp35 or TrkA antagonist for use in the methods of the invention is an antibody molecule, or immunospecific fragment thereof. Unless it is specifically noted, as used herein, a "fragment thereof" in reference to an antibody refers to an immunospecific fragment, i.e., an antigen-specific fragment. In one embodiment, an antibody for use in the methods of the invention is a bispecific binding molecule, binding polypeptide, or antibody, e.g., a bispecific antibody, minibody, domain deleted antibody, or fusion protein having binding specificity for more than one epitope, e.g., more than one antigen or more than one epitope on the same antigen. In one embodiment, a bispecific antibody has at least one binding domain specific for at least one epitope on Sp35 or TrkA. A bispecific antibody may be a tetravalent antibody that has two target binding domains specific for an epitope of Sp35 or TrkA and two target binding domains specific for a second target. Thus, a tetravalent bispecific antibody may be bivalent for each specificity.

Sp35 or TrkA antagonists for use in the methods of the present invention also include Sp35 or TrkA-specific antibodies or antigen-binding fragments, variants, or derivatives which are antagonists of Sp35 or TrkA activity. For example, binding of certain Sp35 or TrkA antibodies to Sp35 or TrkA, as expressed on CNS neurons, blocks inhibition of myelination.

Certain antagonist antibodies for use in the methods described herein specifically or preferentially bind to a particular Sp35 polypeptide fragment or domain. Such Sp35 polypeptide fragments include, but are not limited to, an Sp35 polypeptide comprising, consisting essentially of, or consisting of amino acids 34 to 532; 34 to 417, 34 to 425, 34 to 493, 66 to 532, 66 to 417 (LRR domain), 66 to 426, 66 to 493, 66 to 532, 417 to 532, 417 to 425 (the Sp35 basic region), 417 to 424 (the Sp35 basic region), 417 to 493, 417 to 532, 419 to 493 (the Sp35 Ig region), or 425 to 532 of SEQ ID NO:2, or an Sp35 variant polypeptide at least 70%, 75%, 80%, 85%, 90%, or 95% identical to amino acids 34 to 532; 34 to 417, 34 to 425, 34 to 493, 66 to 532, 66 to 417, 66 to 426, 66 to 493, 66 to 532, 417 to 532, 417 to 425 (the Sp35 basic region), 417 to 493, 417 to 532, 419 to 493 (the Sp35 Ig region), or 425 to 532 of SEQ ID NO:2.

Additional Sp35 peptide fragments to which certain Sp35 specific antibodies, or antigen-binding fragments, variants, or derivatives thereof for use in the methods of the present invention bind include, but are not limited to, those fragments comprising, consisting essentially of, or consisting of one or more leucine-rich-repeats (LRR) of Sp35. Such fragments, include, for example, fragments comprising, consisting essentially of, or consisting of amino acids 66 to 89, 66 to 113, 66 to 137, 90 to 113, 114 to 137, 138 to 161, 162 to 185, 186 to 209, 210 to 233, 234 to 257, 258 to 281, 282 to 305, 306 to 329, or 330 to 353 of SEQ ID NO:2. Corresponding fragments of a variant Sp35 polypeptide at least 70%, 75%, 80%, 85%, 90%, or 95% identical to amino acids 66 to 89, 66 to 113, 90 to 113, 114 to 137, 138 to 161, 162 to 185, 186 to 209, 210 to 233, 234 to 257, 258 to 281, 282 to 305, 306 to 329, or 330 to 353 of SEQ ID NO:2 are also contemplated.

Additional Sp35 peptide fragments to which certain antibodies, or antigen-binding fragments, variants, or derivatives thereof of the present invention bind include, but are not limited to those fragments comprising, consisting essentially of, or consisting of one or more cysteine rich regions flanking the LRR of Sp35. Such fragments, include, for example, a fragment comprising, consisting essentially of, or consisting of amino acids 34 to 64 of SEQ ID NO:2 (the N-terminal LRR flanking region (LRRNT)), or a fragment comprising, consisting essentially of, or consisting of amino acids 363 to 416 of SEQ ID NO:2 (the C-terminal LRR flanking region (LRRCT)). Corresponding fragments of a variant Sp35 polypeptide at least 70%, 75%, 80%, 85%, 90%, or 95% identical to amino acids 34 to 64 and 363 to 416 of SEQ ID NO:2 are also contemplated.

In other embodiments, the Sp35 antagonists to be used in the methods described herein include an antibody, or antigen-binding fragment, variant, or derivative thereof which specifically or preferentially binds to at least one epitope of Sp35, where the epitope comprises, consists essentially of, or consists of at least about four to five amino acids of SEQ ID NO:2, at least seven, at least nine, or between at least about 15 to about 30 amino acids of SEQ ID NO:2. The amino acids of a given epitope of SEQ ID NO:2 as described may be, but need not be, contiguous or linear. In certain embodiments, at least one epitope of Sp35 comprises, consists essentially of, or consists of a non-linear epitope formed by the extracellular domain of Sp35 as expressed on the surface of a cell or as a soluble fragment, e.g., fused to an IgG Fc region. Thus, in certain embodiments the at least one epitope of Sp35 comprises, consists essentially of, or consists of at least 4, at least 5, at least 6, at least 7, at least 8, at least 9, at least 10, at least 15, at least 20, at least 25, between about 15 to about 30, or at least 10, 15, 20, 25, 30, 35, 40, 45, 50, 55, 60, 65, 70, 75, 80, 85, 90, 95, or 100 contiguous or non-contiguous amino acids of SEQ ID NO:2, where non-contiguous amino acids form an epitope through protein folding.

Certain antagonist antibodies for use in the methods described herein specifically or preferentially bind to a particular TrkA polypeptide fragment or domain. Certain non-limiting examples of TrkA antagonist antibodies include, but are not limited to monoclonal antibodies which prevent or lessen the binding of NGF to the TrkA receptor (e.g. MNAC13; AB1577 (chemicon); and MC192.

Exemplary antibodies or fragments thereof for use in the methods of the present invention include, but are not limited to, isolated antibodies or antigen binding fragments thereof which specifically binds to the same Sp35 epitope as a reference monoclonal antibody selected from the group consisting of 201', 3A3, 3A6, 3B5, 1A7, 1D5, 1G7, 2B10, 2C11, 2F3, 3P1B1.1F9, 3P1D10.2C3, 3P1E11.3B7, 3P2C6.3G10.2H7, 3P2C9.2G4, 3P4A6.1D9, 3P4A1.2B9, 3P4C2.2D2, 3P4C5.1D8, 3P4C8.2G9, 6P4F4.1Ds, 6P4F4.1F9, 7P1D5.1G9, 1B6.4, 2C7.2, 2D6.1, 2F7.3, 2H3.2, 3C11.1, 3E3.1, 3H11.2, 3G8.1, 2B8.1, 3B5.230-C12 (Li01), 38-D01 (Li02), 35-E04 (Li03), 36-009 (Li04), 30-A11 (Li05), 34-F02 (Li06), 29-E07 (Li07), 34-G04 (Li08), 36-A12 (Li09), 28-D02 (Li10), 30-B01 (Li11), 34-B03 (Li12), Li13, Li32, Li33, Li34, 3383 (L1a.1), 3495(L1a.2), 3563 (L1a.3), 3564 (L1a.4), 3565 (L1a.5), 3566 (L1a.6), 3567 (L1a.7), 3568 (L1a.8), 3569 (L1a.9), 3570 (L1a.10), 3571 (L1a.11), 3582 (L1a.12), 1968 (L1a.13), 3011, 3012, 3013, 3418, 3422, 3562, D05, D07, D08, D10 and D11, as described in the International Application PCT/US06/26271 entitled "Sp35 Antibodies and Uses Thereof" to Mi et al, filed Jul. 7, 2006 and is incorporated by reference in its entirety.

In other embodiments, the Sp35 and TrkA antagonists to be used in the methods of the present invention include Sp35 or TrkA antibodies, or antigen-binding fragments, variants, or derivatives thereof which specifically or preferentially bind to at least one epitope of Sp35 or TrkA, where the epitope comprises, consists essentially of, or consists of, in addition to one, two, three, four, five, six or more contiguous or non-contiguous amino acids of SEQ ID NO:2 or SEQ ID NO:4, respectively, as described above, and an additional moiety which modifies the protein, e.g., a carbohydrate moiety may be included such that the Sp35 or TrkA antibody binds with higher affinity to modified target protein than it does to an unmodified version of the protein. Alternatively, the Sp35 or TrkA antibody does not bind the unmodified version of the target protein at all.

In certain embodiments, the Sp35 or TrkA antagonists to be used in the methods of the present invention include an antibody, or antigen-binding fragment, variant, or derivative thereof of the invention binds specifically to at least one epitope of Sp35 or TrkA or fragment or variant described above, i.e., binds to such an epitope more readily than it would bind to an unrelated, or random epitope; binds preferentially to at least one epitope of Sp35 or TrkA or fragment or variant described above, i.e., binds to such an epitope more readily than it would bind to a related, similar, homologous, or analogous epitope; competitively inhibits binding of a reference antibody which itself binds specifically or preferentially to a certain epitope of Sp35 or TrkA or fragment or variant described above; or binds to at least one epitope of Sp35 or TrkA or fragment or variant described above with an affinity characterized by a dissociation constant $K_D$ of less than about $5\times10^{-2}$ M, about $10^{-2}$ M, about $5\times10^{-3}$ M, about $10^{-3}$ M, about $5\times10^{-4}$ M, about $10^{-4}$ M, about $5\times10^{-5}$ M, about $10^{-5}$ M, about $5\times10^{-6}$ M, about $10^{-6}$ M, about $5\times10^{-7}$ M, about $10^{-7}$ M, about $5\times10^{-8}$ M, about $10^{-8}$ M, about $5\times10^{-9}$ M, about $10^{-9}$ M, about $5\times10^{-10}$ M, about $10^{-10}$ M, about $5\times10^{-11}$ M, about $10^{-11}$ M, about $5\times10^{-12}$ M, about $10^{-12}$ M, about $5\times10^{-13}$ M, about $10^{-13}$ M, about $5\times10^{-14}$ M, about $10^{-14}$ M, about $5\times10^{-15}$ M, or about $10^{-15}$ M. In a particular aspect, the antibody or fragment thereof preferentially binds to a human Sp35 or TrkA polypeptide or fragment thereof, relative to a murine Sp35 or TrkA polypeptide or fragment thereof.

As used in the context of antibody binding dissociation constants, the term "about" allows for the degree of variation inherent in the methods utilized for measuring antibody affinity. For example, depending on the level of precision of the instrumentation used, standard error based on the number of samples measured, and rounding error, the term "about $10^{-2}$ M" might include, for example, from 0.05 M to 0.005 M.

In specific embodiments, the Sp35 or TrkA antagonists for use in the methods of the present invention include an antibody, or antigen-binding fragment, variant, or derivative thereof of the invention binds Sp35 or TrkA polypeptides or fragments or variants thereof with an off rate (k(off)) of less than or equal to $5\times10^{-2}$ sec$^{-1}$, $10^{-2}$ sec$^{-1}$, $5\times10^{-3}$ sec$^{-1}$ or $10^{-3}$ sec$^{-1}$. Alternatively, an antibody, or antigen-binding fragment, variant, or derivative thereof of the invention binds Sp35 or TrkA polypeptides or fragments or variants thereof with an off rate (k(off)) of less than or equal to $5\times10^{-4}$ sec$^{-1}$, 10–4 sec$^{-1}$, $5\times10^{-5}$ sec$^{-1}$, or $10^{-5}$ sec$^{-1}$ $5\times10^{-6}$ sec$^{-1}$, $10^{-6}$ sec$^{-1}$, $5\times10^{-7}$ sec$^{-1}$ or $10^{-7}$ sec$^{-1}$.

In other embodiments, the Sp35 or TrkA antagonists for use in the methods of the present invention include an antibody, or antigen-binding fragment, variant, or derivative thereof of the invention binds Sp35 or TrkA polypeptides or fragments or variants thereof with an on rate (k(on)) of greater than or equal to $10^3$ M$^{-1}$ sec$^{-1}$, $5\times10^3$ M$^{-1}$ sec$^{-1}$, $10^4$ M$^{-1}$ sec$^{-1}$ or $5\times10^4$ M$^{-1}$ sec$^{-1}$. Alternatively, an antibody, or antigen-binding fragment, variant, or derivative thereof of the invention binds Sp35 or TrkA polypeptides or fragments or variants thereof with an on rate (k(on)) greater than or equal to $10^5$ M$^{-1}$ sec$^{-1}$, $5\times10^5$ M$^{-1}$ sec$^{-1}$, $10^6$ M$^{-1}$ sec$^{-1}$, or $5\times10^6$ M$^{-1}$ sec$^{-1}$ or $10^7$ M$^{-1}$ sec$^{-1}$.

Certain methods of the present invention comprise administration of an Sp35 or TrkA antagonist antibody, or immunospecific fragment thereof, in which at least a fraction of one or more of the constant region domains has been deleted or otherwise altered so as to provide desired biochemical characteristics such as reduced effector functions, the ability to non-covalently dimerize, increased ability to localize at the site of a tumor, reduced serum half-life, or increased serum half-life when compared with a whole, unaltered antibody of approximately the same immunogenicity. For example, certain antibodies for use in the methods described herein are domain deleted antibodies which comprise a polypeptide chain similar to an immunoglobulin heavy chain, but which lack at least a portion of one or more heavy chain domains. For instance, in certain antibodies, one entire domain of the constant region of the modified antibody will be deleted, for example, all or part of the CH2 domain will be deleted.

In certain Sp35 or TrkA antagonist antibodies or immunospecific fragments thereof for use in the methods described herein, the Fc portion may be mutated to decrease effector function using techniques known in the art. For example, the deletion or inactivation (through point mutations or other means) of a constant region domain may reduce Fc receptor binding of the circulating modified antibody thereby increasing tumor localization. In other cases it may be that constant region modifications consistent with the instant invention moderate complement binding and thus reduce the serum half life and nonspecific association of a conjugated cytotoxin. Yet other modifications of the constant region may be used to modify disulfide linkages or oligosaccharide moieties that allow for enhanced localization due to increased antigen specificity or antibody flexibility. The resulting physiological profile, bioavailability and other biochemical effects of the modifications, such as tumor localization, biodistribution and serum half-life, may easily be measured and quantified using well-known immunological techniques without undue experimentation.

Modified forms of antibodies or immunospecific fragments thereof for use in the methods disclosed herein can be made from whole precursor or parent antibodies using techniques known in the art. Exemplary techniques are discussed in more detail herein.

In certain embodiments both the variable and constant regions of Sp35 or TrkA antagonist antibodies or immunospecific fragments thereof for use in the methods disclosed herein are fully human. Fully human antibodies can be made using techniques that are known in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140. Other techniques are known in the art. Fully human antibodies can likewise be produced by various display technologies, e.g., phage display or other viral display systems, as described in more detail elsewhere herein.

Sp35 or TrkA antagonist antibodies or immunospecific fragments thereof for use in the methods disclosed herein can be made or manufactured using techniques that are known in the art. In certain embodiments, antibody molecules or fragments thereof are "recombinantly produced," i.e., are produced using recombinant DNA technology. Exemplary techniques for making antibody molecules or fragments thereof are discussed in more detail elsewhere herein.

Sp35 or TrkA antagonist antibodies or immunospecific fragments thereof for use in the methods disclosed herein include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

In preferred embodiments, an Sp35 or TrkA antagonist antibody or immunospecific fragment thereof for use in the methods disclosed herein will not elicit a deleterious immune response in the animal to be treated, e.g., in a human. In one embodiment, Sp35 or TrkA antagonist antibodies or immunospecific fragments thereof for use in the methods disclosed herein can be modified to reduce their immunogenicity using art-recognized techniques. For example, antibodies can be humanized, primatized, deimmunized, or chimeric antibodies can be made. These types of antibodies are derived from a non-human antibody, typically a murine or primate antibody, that retains or substantially retains the antigen-binding properties of the parent antibody, but which is less immunogenic in humans. This may be achieved by various methods, including (a) grafting the entire non-human variable domains onto human constant regions to generate chimeric antibodies; (b) grafting at least a part of one or more of the non-human complementarity determining regions (CDRs) into a human framework and constant regions with or without retention of critical framework residues; or (c) transplanting the entire non-human variable domains, but "cloaking" them with a human-like section by replacement of surface residues. Such methods are disclosed in Morrison et al., *Proc. Natl. Acad. Sci.* 81:6851-6855 (1984); Morrison et al., *Adv. Immunol.* 44:65-92 (1988); Verhoeyen et al., *Science* 239:1534-1536 (1988); Padlan, *Molec. Immun.* 28:489-498 (1991); Padlan, *Molec. Immun.* 31:169-217 (1994), and U.S. Pat. Nos. 5,585,089, 5,693,761, 5,693,762, and 6,190,370, all of which are hereby incorporated by reference in their entirety.

De-immunization can also be used to decrease the immunogenicity of an antibody. As used herein, the term "de-immunization" includes alteration of an antibody to modify T cell epitopes (see, e.g., WO9852976A1, WO0034317A2). For example, $V_H$ and $V_L$ sequences from the starting antibody are analyzed and a human T cell epitope "map" from each V region showing the location of epitopes in relation to complementarity-determining regions (CDRs) and other key residues within the sequence. Individual T cell epitopes from the T cell epitope map are analyzed in order to identify alternative amino acid substitutions with a low risk of altering activity of the final antibody. A range of alternative $V_H$ and $V_L$ sequences are designed comprising combinations of amino acid substitutions and these sequences are subsequently incorporated into a range of binding polypeptides, e.g., Sp35 or TrkA antagonist antibodies or immunospecific fragments thereof for use in the methods disclosed herein, which are then tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

Sp35 or TrkA antagonist antibodies or fragments thereof for use in the methods of the present invention may be generated by any suitable method known in the art. Polyclonal antibodies can be produced by various procedures well known in the art. For example, a Sp35 or TrkA immunospecific fragment can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, Cold Spring Harbor Laboratory Press, 2nd ed. (1988); Hammerling et al., in: *Monoclonal Antibodies and T-Cell Hybridomas* Elsevier, N.Y., 563-681 (1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Thus, the term "monoclonal antibody" is not limited to antibodies produced through hybridoma technology. Monoclonal antibodies can be prepared using a wide variety of techniques known in the art including the use of hybridoma and recombinant and phage display technology.

Using art recognized protocols, in one example, antibodies are raised in mammals by multiple subcutaneous or intraperitoneal injections of the relevant antigen (e.g., purified Sp35 or TrkA antigens or cells or cellular extracts comprising such antigens) and an adjuvant. This immunization typically elicits an immune response that comprises production of antigen-reactive antibodies from activated splenocytes or lymphocytes. While the resulting antibodies may be harvested from the serum of the animal to provide polyclonal preparations, it is often desirable to isolate individual lymphocytes from the spleen, lymph nodes or peripheral blood to provide homogenous preparations of monoclonal antibodies (mAbs). Preferably, the lymphocytes are obtained from the spleen.

In this well known process (Kohler et al., *Nature* 256:495 (1975)) the relatively short-lived, or mortal, lymphocytes from a mammal which has been injected with antigen are fused with an immortal tumor cell line (e.g. a myeloma cell line), thus producing hybrid cells or "hybridomas" which are both immortal and capable of producing the genetically coded antibody of the B cell. The resulting hybrids are segregated into single genetic strains by selection, dilution, and regrowth with each individual strain comprising specific genes for the formation of a single antibody. They produce antibodies which are homogeneous against a desired antigen and, in reference to their pure genetic parentage, are termed "monoclonal."

Hybridoma cells thus prepared are seeded and grown in a suitable culture medium that preferably contains one or more substances that inhibit the growth or survival of the unfused, parental myeloma cells. Those skilled in the art will appreciate that reagents, cell lines and media for the formation, selection and growth of hybridomas are commercially available from a number of sources and standardized protocols are well established. Generally, culture medium in which the hybridoma cells are growing is assayed for production of monoclonal antibodies against the desired antigen. Preferably, the binding specificity of the monoclonal antibodies produced by hybridoma cells is determined by in vitro assays such as immunoprecipitation, radioimmunoassay (RIA) or enzyme-linked immunoabsorbent assay (ELISA). After hybridoma cells are identified that produce antibodies of the desired specificity, affinity and/or activity, the clones may be subcloned by limiting dilution procedures and grown by standard methods (Goding, *Monoclonal Antibodies: Principles and Practice*, Academic Press, pp 59-103 (1986)). It will further be appreciated that the monoclonal antibodies secreted by the subclones may be separated from culture medium, ascites fluid or serum by conventional purification procedures such as, for example, protein-A, hydroxylapatite chromatography, gel electrophoresis, dialysis or affinity chromatography.

Antibody fragments that recognize specific epitopes may be generated by known techniques. For example, Fab and F(ab')$_2$ fragments may be produced by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the $C_H1$ domain of the heavy chain.

Those skilled in the art will also appreciate that DNA encoding antibodies or antibody fragments (e.g., antigen binding sites) may also be derived from antibody phage libraries. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Exemplary methods are set forth, for example, in EP 368 684 B1; U.S. Pat. No. 5,969,108, Hoogenboom, H. R. and Chames, *Immunol. Today* 21:371 (2000); Nagy et al. *Nat. Med.* 8:801 (2002); Huie et al., *Proc. Natl. Acad. Sci. USA* 98:2682 (2001); Lui et al., *J. Mol. Biol.* 315:1063 (2002), each of which is incorporated herein by reference. Several publications (e.g., Marks et al., *Bio/Technology* 10:779-783 (1992)) have described the production of high affinity human antibodies by chain shuffling, as well as combinatorial infection and in vivo recombination as a strategy for constructing large phage libraries. In another embodiment, ribosomal display can be used to replace bacteriophage as the display platform (see, e.g., Hanes et al., *Nat. Biotechnol.* 18:1287 (2000); Wilson et al., *Proc. Natl. Acad. Sci. USA* 98:3750 (2001); or Irving et al., *J. Immunol. Methods* 248:31 (2001)). In yet another embodiment, cell surface libraries can be screened for antibodies (Boder et al., *Proc. Natl. Acad. Sci. USA* 97:10701 (2000); Daugherty et al., *J. Immunol. Methods* 243:211 (2000)). Such procedures provide alternatives to traditional hybridoma techniques for the isolation and subsequent cloning of monoclonal antibodies.

In phage display methods, functional antibody domains are displayed on the surface of phage particles which carry the polynucleotide sequences encoding them. In particular, DNA sequences encoding $V_H$ and $V_L$ regions are amplified from animal cDNA libraries (e.g., human or murine cDNA libraries of lymphoid tissues) or synthetic cDNA libraries. In certain embodiments, the DNA encoding the $V_H$ and $V_L$ regions are joined together by an scFv linker by PCR and cloned into a phagemid vector (e.g., p CANTAB 6 or pComb 3 HSS). The vector is electroporated in *E. coli* and the *E. coli* is infected with helper phage. Phage used in these methods are typically filamentous phage including fd and M13 and the $V_H$ or $V_L$ regions are usually recombinantly fused to either the phage gene III or gene VIII. Phage expressing an antigen binding domain that binds to an antigen of interest (i.e., a Sp35 or TrkA polypeptide or a fragment thereof) can be selected or identified with antigen, e.g., using labeled antigen or antigen bound or captured to a solid surface or bead.

Additional examples of phage display methods that can be used to make the antibodies include those disclosed in Brinkman et al., *J. Immunol. Methods* 182:41-50 (1995); Ames et al., *J. Immunol. Methods* 184:177-186 (1995); Kettleborough et al., *Eur. J. Immunol.* 24:952-958 (1994); Persic et al., *Gene* 187:9-18 (1997); Burton et al., *Advances in Immunology* 57:191-280 (1994); PCT Application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria. For example, techniques to recombinantly produce Fab, Fab' and F(ab')$_2$ fragments can also be employed using methods known in the art such as those disclosed in PCT publication WO 92/22324; Mullinax et al., *BioTechniques* 12(6):864-869 (1992); and Sawai et al., *AJRI* 34:26-34 (1995); and Better et al., *Science* 240:1041-1043 (1988) (said references incorporated by reference in their entireties).

Examples of techniques which can be used to produce single-chain Fvs and antibodies include those described in U.S. Pat. Nos. 4,946,778 and 5,258,498; Huston et al., *Methods in Enzymology* 203:46-88 (1991); Shu et al., *PNAS* 90:7995-7999 (1993); and Skerra et al., *Science* 240:1038-1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See, e.g., Morrison, *Science* 229:1202 (1985); Oi et al., *BioTechniques* 4:214 (1986); Gillies et al., *J. Immunol. Methods* 125:191-202 (1989); U.S. Pat. Nos. 5,807,715; 4,816,567; and 4,816,397, which are incorporated herein by reference in their entireties. Humanized antibodies are antibody molecules from non-human species antibody that binds the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, and preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., *Nature* 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, *Molecular Immunology* 28(4/5):489-498 (1991); Studnicka et al., *Protein Engineering* 7(6):805-814 (1994); Roguska. et al., *PNAS* 91:969-973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered nonfunctional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a desired target polypeptide. Monoclonal antibodies directed against the antigen can be obtained from the immunized, transgenic mice using conventional hybridoma technology. The human immunoglobulin transgenes harbored by the transgenic mice rearrange during B-cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar *Int. Rev. Immunol.* 13:65-93 (1995). For a detailed discussion of this technology for producing human antibodies and human monoclonal antibodies and protocols for producing such antibodies, see, e.g., PCT publications WO 98/24893; WO 96/34096; WO 96/33735; U.S. Pat. Nos. 5,413,923; 5,625,126; 5,633,425; 5,569,825; 5,661,016; 5,545,806; 5,814,318; and 5,939,598, which are incorporated by reference herein in their entirety. In addition, companies such as Abgenix, Inc. (Freemont, Calif.) and GenPharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., *Bio/Technology* 12:899-903 (1988)). See also, U.S. Pat. No. 5,565,332.

In another embodiment, DNA encoding desired monoclonal antibodies for use in the methods of the present invention may be readily isolated and sequenced using conventional procedures (e.g., by using oligonucleotide probes that are capable of binding specifically to genes encoding the heavy and light chains of murine antibodies). The isolated and subcloned hybridoma cells serve as a preferred source of such DNA. Once isolated, the DNA may be placed into expression vectors, which are then transfected into prokaryotic or eukaryotic host cells such as *E. coli* cells, simian COS cells, Chinese Hamster Ovary (CHO) cells or myeloma cells that do not otherwise produce immunoglobulins. More particularly, the isolated DNA (which may be synthetic as described herein) may be used to clone constant and variable region sequences for the manufacture antibodies as described in Newman et al., U.S. Pat. No. 5,658,570, filed Jan. 25, 1995, which is incorporated by reference herein. Essentially, this entails extraction of RNA from the selected cells, conversion to cDNA, and amplification by PCR using Ig specific primers. Suitable primers for this purpose are also described in U.S. Pat. No. 5,658,570. As will be discussed in more detail below, transformed cells expressing the desired antibody may be grown up in relatively large quantities to provide clinical and commercial supplies of the immunoglobulin.

In a specific embodiment, the amino acid sequence of the heavy and/or light chain variable domains may be inspected to identify the sequences of the complementarity determining regions (CDRs) by methods that are well known in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody. The framework regions may be naturally occurring or consensus framework regions, and preferably human framework regions (see, e.g., Chothia et al., *J. Mol. Biol.* 278:457-479 (1998) for a listing of human framework regions). Preferably, the polynucleotide generated by the combination of the framework regions and CDRs encodes an antibody that specifically binds to at least one epitope of a desired polypeptide, e.g., Sp35. Preferably, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., *Proc. Natl. Acad. Sci.* 81:851-855 (1984); Neuberger et al., *Nature* 312:604-608 (1984); Takeda et al., *Nature* 314:452-454 (1985)) by splicing genes from a mouse antibody molecule of appropriate antigen specificity together with genes from a human antibody molecule of appropriate biological activity can be used. As used herein, a chimeric antibody is a molecule in which different portions are derived from different animal species, such as those having a variable region derived from a murine monoclonal antibody and a human immunoglobulin constant region, e.g., humanized antibodies.

Alternatively, techniques described for the production of single chain antibodies (U.S. Pat. No. 4,694,778; Bird, *Science* 242:423-442 (1988); Huston et al., *Proc. Natl. Acad. Sci. USA* 85:5879-5883 (1988); and Ward et al., *Nature* 334:544-554 (1989)) can be adapted to produce single chain antibodies. Single chain antibodies are formed by linking the heavy and light chain fragments of the Fv region via an amino acid bridge, resulting in a single chain antibody. Techniques for the assembly of functional Fv fragments in *E coli* may also be used (Skerra et al., *Science* 242:1038-1041 (1988)).

Sp35 or TrkA antagonist antibodies may also be human or substantially human antibodies generated in transgenic animals (e.g., mice) that are incapable of endogenous immunoglobulin production (see e.g., U.S. Pat. Nos. 6,075,181, 5,939,598, 5,591,669 and 5,589,369 each of which is incorporated herein by reference). For example, it has been described that the homozygous deletion of the antibody heavy-chain joining region in chimeric and germ-line mutant mice results in complete inhibition of endogenous antibody production. Transfer of a human immunoglobulin gene array to such germ line mutant mice will result in the production of human antibodies upon antigen challenge. Another preferred means of generating human antibodies using SCID mice is disclosed in U.S. Pat. No. 5,811,524 which is incorporated herein by reference. It will be appreciated that the genetic material associated with these human antibodies may also be isolated and manipulated as described herein.

Yet another highly efficient means for generating recombinant antibodies is disclosed by Newman, *Biotechnology* 10: 1455-1460 (1992). Specifically, this technique results in the generation of primatized antibodies that contain monkey variable domains and human constant sequences. This reference is incorporated by reference in its entirety herein. Moreover, this technique is also described in commonly assigned U.S. Pat. Nos. 5,658,570, 5,693,780 and 5,756,096 each of which is incorporated herein by reference.

In another embodiment, lymphocytes can be selected by micromanipulation and the variable genes isolated. For example, peripheral blood mononuclear cells can be isolated from an immunized mammal and cultured for about 7 days in vitro. The cultures can be screened for specific IgGs that meet the screening criteria. Cells from positive wells can be isolated. Individual Ig-producing B cells can be isolated by FACS or by identifying them in a complement-mediated hemolytic plaque assay. Ig-producing B cells can be micromanipulated into a tube and the $V_H$ and $V_L$ genes can be amplified using, e.g., RT-PCR. The $V_H$ and $V_L$ genes can be cloned into an antibody expression vector and transfected into cells (e.g., eukaryotic or prokaryotic cells) for expression.

Alternatively, antibody-producing cell lines may be selected and cultured using techniques well known to the skilled artisan. Such techniques are described in a variety of laboratory manuals and primary publications. In this respect, techniques suitable for use in the invention as described below are described in *Current Protocols in Immunology*, Coligan et al., Eds., Green Publishing Associates and Wiley-Interscience, John Wiley and Sons, New York (1991) which is herein incorporated by reference in its entirety, including supplements.

Antibodies for use in the methods disclosed herein can be produced by any method known in the art for the synthesis of antibodies, in particular, by chemical synthesis or preferably, by recombinant expression techniques as described herein.

It will further be appreciated that the scope of this invention further encompasses all alleles, variants and mutations of antigen binding DNA sequences.

As is well known, RNA may be isolated from the original hybridoma cells or from other transformed cells by standard techniques, such as guanidinium isothiocyanate extraction and precipitation followed by centrifugation or chromatography. Where desirable, mRNA may be isolated from total RNA by standard techniques such as chromatography on oligo dT cellulose. Suitable techniques are familiar in the art.

In one embodiment, cDNAs that encode the light and the heavy chains of the antibody for use in the methods of the present invention may be made, either simultaneously or separately, using reverse transcriptase and DNA polymerase in accordance with well known methods. PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes.

DNA, typically plasmid DNA, may be isolated from the cells using techniques known in the art, restriction mapped and sequenced in accordance with standard, well known techniques set forth in detail, e.g., in the foregoing references relating to recombinant DNA techniques. Of course, the DNA may be synthetic according to the present invention at any point during the isolation process or subsequent analysis.

Recombinant expression of an antibody, or fragment, derivative or analog thereof, e.g., a heavy or light chain of an antibody which is an Sp35 antagonist, requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody for use in the methods described herein. Thus, the invention includes host cells containing a polynucleotide encoding an antibody of the invention, or a heavy or light chain thereof, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express antibody molecules for use in the methods described herein. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., *Gene* 45:101 (1986); Cockett et al., *Bio/Technology* 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited to, the *E. coli* expression vector pUR278 (Ruther et al., *EMBO J.* 2:1791 (1983)), in which the antibody coding sequence may be ligated individually into the vector in frame with the lacZ coding region so that a fusion protein is produced; pIN vectors (Inouye & Inouye, *Nucleic Acids Res.* 13:3101-3109 (1985); Van Heeke & Schuster, *J. Biol. Chem.* 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is typically used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, *Proc. Natl. Acad. Sci. USA* 81:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.* 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, HeLa, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression may be used. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which stably express the antibody molecule.

A number of selection systems may be used, including but not limited to the herpes simplex virus thymidine kinase (Wigler et al., *Cell* 11:223 (1977)), hypoxanthine-guanine phosphoribosyltransferase (Szybalska & Szybalski, *Proc. Natl. Acad. Sci. USA* 48:202 (1992)), and adenine phosphoribosyltransferase (Lowy et al., *Cell* 22:817 1980) genes, can be employed in tk-, hgprt- or aprt-cells, respectively. Also, antimetabolite resistance can be used as the basis of selection for the following genes: dhfr, which confers resistance to methotrexate (Wigler et al., *Natl. Acad. Sci. USA* 77:357 (1980); O'Hare et al., *Proc. Natl. Acad. Sci. USA* 78:1527 (1981)); gpt, which confers resistance to mycophenolic acid (Mulligan & Berg, *Proc. Natl. Acad. Sci. USA* 78:2072 (1981)); neo, which confers resistance to the aminoglycoside G-418 *Clinical Pharmacy* 12:488-505; Wu and Wu, *Biotherapy* 3:87-95 (1991); Tolstoshev, *Ann. Rev. Pharmacol. Toxicol.* 32:573-596 (1993); Mulligan, *Science* 260:926-932 (1993); and Morgan and Anderson, *Ann. Rev. Biochem.* 62:191-217 (1993); *TIB TECH* 11(5):155-215 (May, 1993); and hygro, which confers resistance to hygromycin (Santerre et al., *Gene* 30:147 (1984). Methods commonly known in the art of recombinant DNA technology which can be used are described in Ausubel et al. (eds.), *Current Protocols in Molecular Biology*, John Wiley & Sons, NY (1993); Kriegler, *Gene Transfer and Expression*, A Laboratory Manual, Stockton Press, NY (1990); and in Chapters 12 and 13, Dracopoli et al. (eds), *Current Protocols in Human Genetics*, John Wiley & Sons, NY (1994); Colberre-Garapin et al., *J. Mol. Biol.* 150:1 (1981), which are incorporated by reference herein in their entireties.

The expression levels of an antibody molecule can be increased by vector amplification (for a review, see Bebbington and Hentschel, *The use of vectors based on gene amplification for the expression of cloned genes in mammalian cells in DNA cloning*, Academic Press, New York, Vol. 3. (1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., *Mol. Cell. Biol.* 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain is advantageously placed before the heavy chain to avoid an excess of toxic free heavy chain (Proudfoot, *Nature* 322:52 (1986); Kohler, *Proc. Natl. Acad. Sci. USA* 77:2197 (1980)). The coding sequences for the heavy and light chains may comprise cDNA or genomic DNA.

Once an antibody molecule of the invention has been recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Alternatively, a preferred method for increasing the affinity of antibodies of the invention is disclosed in US 2002 0123057 A1, which is incorporated herein by reference.

In one embodiment, a binding molecule or antigen binding molecule for use in the methods of the invention comprises a synthetic constant region wherein one or more domains are partially or entirely deleted ("domain-deleted antibodies"). In certain embodiments compatible modified antibodies will comprise domain deleted constructs or variants wherein the entire $C_H2$ domain has been removed ($\Delta C_H2$ constructs). For other embodiments a short connecting peptide may be substituted for the deleted domain to provide flexibility and freedom of movement for the variable region. Those skilled in the art will appreciate that such constructs are particularly preferred due to the regulatory properties of the $C_H2$ domain on the catabolic rate of the antibody.

In certain embodiments, modified antibodies for use in the methods disclosed herein are minibodies. Minibodies can be made using methods described in the art (see, e.g., U.S. Pat. No. 5,837,821 or WO 94/09817A1).

In another embodiment, modified antibodies for use in the methods disclosed herein are $C_H2$ domain deleted antibodies which are known in the art. Domain deleted constructs can be derived using a vector (e.g., from Biogen DEC Incorporated) encoding an $IgG_1$ human constant domain (see, e.g., WO 02/060955A2 and WO02/096948A2, which are incorporated herein by reference). This exemplary vector was engineered to delete the $C_H2$ domain and provide a synthetic vector expressing a domain deleted $IgG_1$ constant region.

In one embodiment, an Sp35 or TrkA antagonist antibody or fragment thereof for use in the methods disclosed herein comprises an immunoglobulin heavy chain having deletion or substitution of a few or even a single amino acid as long as it permits association between the monomeric subunits. For example, the mutation of a single amino acid in selected areas of the $C_H2$ domain may be enough to substantially reduce Fc binding and thereby increase tumor localization. Similarly, it may be desirable to simply delete that part of one or more constant region domains that control the effector function (e.g. complement binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be synthetic through the mutation or substitution of one or more amino acids that enhances the profile of the resulting construct. In this respect it may be possible to disrupt the activity provided by a conserved binding site (e.g. Fc binding) while substantially maintaining the configuration and immunogenic profile of the modified antibody. Yet other embodiments comprise the addition of one or more amino acids to the constant region to enhance desirable characteristics such as effector function or provide for more cytotoxin or carbohydrate attachment. In such embodiments it may be desirable to insert or replicate specific sequences derived from selected constant region domains.

The present invention also provides the use of antibodies that comprise, consist essentially of, or consist of, variants (including derivatives) of antibody molecules (e.g., the $V_H$ regions and/or $V_L$ regions) described herein, which antibodies or fragments thereof immunospecifically bind to a Sp35 polypeptide. Standard techniques known to those of skill in the art can be used to introduce mutations in the nucleotide sequence encoding a binding molecule, including, but not limited to, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference $V_H$ region, $V_H$CDR1, $V_H$CDR2, $V_H$CDR3, $V_L$ region, $V_L$CDR1, $V_L$CDR2, or $V_L$CDR3. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity.

For example, it is possible to introduce mutations only in framework regions or only in CDR regions of an antibody molecule. Introduced mutations may be silent or neutral missense mutations, i.e., have no, or little, effect on an antibody's ability to bind antigen. These types of mutations may be useful to optimize codon usage, or improve a hybridoma's antibody production. Alternatively, non-neutral missense mutations may alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein may routinely be expressed and the functional and/or biological activity of the encoded protein can be determined using techniques described herein or by routinely modifying techniques known in the art.

Additional Antagonists and Combinations of Antagonists for Use in the Methods of the Invention In addition to the antagonists described previously, additional TrkA antagonists for use in the methods of the present invention include any polypeptide, antibody, compound or nucleotide which would block, inhibit, interfere or reduce the activity of TrkA. Such antagonist include polypeptides, antibodies, compounds or nucleotides which interfere with the binding of the TrkA ligand, Nerve Growth Factor (NGF), to the TrkA receptor and as such are also considered NGF antagonists. Such molecules include but are not limited to antibodies which disrupt the interact between NGF and TrkA, peptomimetic antagonists of TrkA and NGF analogs which do not activate the TrkA receptor. Examples of these types of molecules may be found, for example, in U.S. Pat. Nos. 6,881,719, 6,919,426, 6,034,119, and International Publication No. WO 95/21193, which are hereby incorporated by reference in their entireties.

The antagonists described herein for use in the methods of the present invention may be administered as compositions in various combinations. For example, various TrkA antagonist may be used in combination with Sp35 antagonists. Compositions for use in the methods of the present invention may also include multiple TrkA antagonists and Sp35 antagonists.

Additionally, compositions for use in the present invention may include other antagonists to proteins expressed in the CNS such as Nogo Receptor 1 (NgR1), Sp35 (LINGO-1), TAJ or Oligodendrocyte-myelin glycoprotein (OMgp). Anatagonists of NgR1 are described in U.S. Publication Nos. 2002/0077295 and 2005/0271655 A1 and International Application Publication Nos. WO 01/51520, WO 03/031462, WO 2004/014311 and WO 2005/016955, which are hereby incorporated by reference in their entireties. Antagonists of Sp35 (LINGO-1) may be found in U.S Publication No. 2006/0009388 A1 and International Publication No. WO 2004/085648, which are hereby incorporated by reference in their entireties. Examples of TAJ antagonists are described in U.S. Publication No. 2006/0058223 A1, which is hereby incorporated by reference in its entirety. OMgp antagonists are described in U.S. Provisional Application Nos. 60/730,357 and 60/735,170 which are hereby incorporated by reference in their entireties. Compositions for use in the methods of the present invention may also include any number and combination of TrkA, Sp35, NgR1, TAJ and OMgp antagonists.

Aptamers

In another embodiment, the Sp35 or TrkA antagonist for use in the methods of the present invention is an aptamer. An aptamer can be a nucleotide or a polypeptide which has a unique sequence, has the property of binding specifically to a desired target (e.g. a polypeptide), and is a specific ligand of a given target. Nucleotide aptamers of the invention include double stranded DNA and single stranded RNA molecules that bind to Sp35 or TrkA.

Nucleic acid aptamers are selected using methods known in the art, for example via the Systematic Evolution of Ligands by Exponential Enrichment (SELEX) process. SELEX is a method for the in vitro evolution of nucleic acid molecules with highly specific binding to target molecules as described in e.g. U.S. Pat. Nos. 5,475,096, 5,580,737, 5,567,588, 5,707,796, 5,763,177, 6,011,577, and 6,699,843, incorporated herein by reference in their entirety. Another screening method to identify aptamers is described in U.S. Pat. No. 5,270,163 (also incorporated herein by reference). The SELEX process is based on the capacity of nucleic acids for forming a variety of two- and three-dimensional structures, as well as the chemical versatility available within the nucleotide monomers to act as ligands (form specific binding pairs) with virtually any chemical compound, whether monomeric or polymeric, including other nucleic acid molecules and polypeptides. Molecules of any size or composition can serve as targets.

The SELEX method involves selection from a mixture of candidate oligonucleotides and step-wise iterations of binding, partitioning and amplification, using the same general selection scheme, to achieve desired binding affinity and selectivity. Starting from a mixture of nucleic acids, preferably comprising a segment of randomized sequence, the SELEX method includes steps of contacting the mixture with the target under conditions favorable for binding; partitioning unbound nucleic acids from those nucleic acids which have bound specifically to target molecules; dissociating the nucleic acid-target complexes; amplifying the nucleic acids dissociated from the nucleic acid-target complexes to yield a ligand enriched mixture of nucleic acids. The steps of binding, partitioning, dissociating and amplifying are repeated through as many cycles as desired to yield highly specific high affinity nucleic acid ligands to the target molecule.

Nucleotide aptamers may be used, for example, as diagnostic tools or as specific inhibitors to dissect intracellular signaling and transport pathways. See James *Curr. Opin. Pharmacol.* 1:540-546 (2001). The high affinity and specificity of nucleotide aptamers makes them good candidates for drug discovery. For example, aptamer antagonists to the toxin ricin have been isolated and have IC50 values in the nanomolar range. See Hesselberth J R et al. J Biol Chem 275:4937-4942 (2000). Nucleotide aptamers may also be used against infectious disease, malignancy and viral surface proteins to reduce cellular infectivity.

Nucleotide aptamers for use in the methods of the present invention may be modified (e.g., by modifying the backbone or bases or conjugated to peptides) as described herein for other polynucleotides.

Using the protein structure of Sp35 or TrkA, screening for aptamers that act on Sp35 or TrkA using the SELEX process would allow for the identification of aptamers that inhibit Sp35 or TrkA-mediated processes (e.g. Sp35 or TrkA-mediated inhibition of myelination).

Polypeptide aptamers for use in the methods of the present invention are random peptides selected for their ability to bind to and thereby block the action of Sp35 or TrkA. Polypeptide aptamers may include a short variable peptide domain attached at both ends to a protein scaffold. This double structural constraint greatly increases the binding affinity of the peptide aptamer to levels comparable to an antibody's (nanomolar range). See e.g., Hoppe-Seyler F et al.

*J. Mol. Med.* 78(8):426-430 (2000). The length of the short variable peptide is typically about 10 to 20 amino acids, and the scaffold may be any protein which has good solubility and compacity properties. One non-limiting example of a scaffold protein is the bacterial protein Thioredoxin-A. See, e.g., Cohen B A et al. *PNAS* 95(24): 14272-14277 (1998). An additional, non-limiting example, of a polypeptide aptamer for use in the methods of the present invention is a Ligand Regulated Peptide Aptamer (LiRPA). The LiRPA scaffold may be composed of three protein domains: FK506 binding protein (FKBP), FRBP-Rapamycin binding domain (FRB) and glutathione-S-transferase (GST). See, e.g., Binkowski B F et al., Chem & Biol 12(7): 847-855 (2005), incorporated herein by reference.

Polypeptide aptamers are peptides or small polypeptides that act as dominant inhibitors of protein function. Peptide aptamers specifically bind to target proteins, blocking their functional ability. Kolonin et al. *Proc. Natl. Acad. Sci.* 95: 14,266-14,271 (1998). Peptide aptamers that bind with high affinity and specificity to a target protein can be isolated by a variety of techniques known in the art. Peptide aptamers can be isolated from random peptide libraries by yeast two-hybrid screens (Xu, C. W., et al. *Proc. Natl. Acad. Sci.* 94:12,473-12,478 (1997)) or by ribosome display (Hanes et al. *Proc. Natl. Acad. Sci.* 94:4937-4942 (1997)). They can also be isolated from phage libraries (Hoogenboom, H. R., et al. *Immunotechnology* 4:1-20 (1998)) or chemically generated peptide libraries. Although the difficult means by which peptide aptamers are synthesized makes their use more complex than polynucleotide aptamers, they have unlimited chemical diversity.

Peptide aptamers for use in the methods of the present invention may be modified (e.g., conjugated to polymers or fused to proteins) as described for other polypeptides elsewhere herein.

Fusion Proteins and Conjugated Polypeptides, Aptamers, Compounds and Antibodies

Sp35 or TrkA antagonist polypeptides, aptamers, compounds and antagonist antibodies for use in the methods disclosed herein may further be recombinantly fused to a heterologous polypeptide at the N- or C-terminus or chemically conjugated (including covalent and non-covalent conjugations) to polypeptides or other compositions. For example, Sp35 or TrkA antagonist polypeptides, aptamers, compounds and antibodies may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

Sp35 or TrkA antagonist polypeptides, aptamers, compounds and antibodies for use in the methods disclosed herein include derivatives that are modified, i.e., by the covalent attachment of any type of molecule such that covalent attachment does not prevent the Sp35 or TrkA antagonist polypeptide, aptamer, compound or antibody from inhibiting the biological function of Sp35 or TrkA. For example, but not by way of limitation, the Sp35 or TrkA antagonist polypeptides, aptamers, compounds and antibodies of the present invention may be modified e.g., by glycosylation, acetylation, pegylation, phosphylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

Sp35 or TrkA antagonist polypeptides, aptamers and antibodies for use in the methods disclosed herein can be composed of amino acids joined to each other by peptide bonds or modified peptide bonds, i.e., peptide isosteres, and may contain amino acids other than the 20 gene-encoded amino acids. Sp35 or TrkA antagonist polypeptides, aptamers and antibodies may be modified by natural processes, such as posttranslational processing, or by chemical modification techniques which are well known in the art. Such modifications are well described in basic texts and in more detailed monographs, as well as in a voluminous research literature. Modifications can occur anywhere in the Sp35 or TrkA antagonist polypeptide or antibody, including the peptide backbone, the amino acid side-chains and the amino or carboxyl termini, or on moieties such as carbohydrates. It will be appreciated that the same type of modification may be present in the same or varying degrees at several sites in a given Sp35 or TrkA antagonist polypeptide, aptamer or antibody. Also, a given Sp35 or TrkA antagonist polypeptide, aptamer or antibody may contain many types of modifications. Sp35 or TrkA antagonist polypeptides, aptamers or antibodies may be branched, for example, as a result of ubiquitination, and they may be cyclic, with or without branching. Cyclic, branched, and branched cyclic Sp35 or TrkA antagonist polypeptides, aptamers and antibodies may result from posttranslational natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, *Proteins—Structure And Molecular Properties*, T. E. Creighton, W. H. Freeman and Company, New York 2nd Ed., (1993); *Posttranslational Covalent Modification Of Proteins*, B. C. Johnson, Ed., Academic Press, New York, pgs. 1-12 (1983); Seifter et al., *Meth Enzymol* 182:626-646 (1990); Rattan et al., *Ann NY Acad Sci* 663:48-62 (1992)).

The present invention also provides for fusion proteins comprising, consisting essentially of, or consisting of a Sp35 or TrkA antagonist polypeptide, aptamer or antibody fusion that inhibits or decreases Sp35 or TrkA function. Preferably, the heterologous polypeptide to which the Sp35 or TrkA antagonist polypeptide, aptamer or antibody is fused is useful for function or is useful to target the Sp35 or TrkA antagonist polypeptide or antibody. In certain embodiments of the invention a soluble Sp35 or TrkA antagonist polypeptide, e.g., an Sp35 polypeptide comprising the LRR domains, Ig domain, or the entire extracellular domain (corresponding to amino acids 34 to 532 of SEQ ID NO: 2), is fused to a heterologous polypeptide moiety to form a Sp35 antagonist fusion polypeptide or a TrkA Ig domain, cysteine domain or leucine rich repeat or the entire extracellular domain or TrkA polypeptide of SEQ ID NO:4 is fused to a heterologous polypeptide moiety to form a TrkA antagonist fusion polypeptide. Sp35 or TrkA antagonist fusion proteins, aptamers and antibodies can be used to accomplish various objectives, e.g., increased serum half-life, improved bioavailability, in vivo targeting to a specific organ or tissue type, improved recombinant expression efficiency, improved host cell secretion, ease of purification, and higher avidity. Depending on the objective(s) to be achieved, the heterologous moiety can be inert or biologically active. Also, it can be chosen to be stably fused to the Sp35 or TrkA antagonist polypeptide, aptamer or antibody or to be cleavable, in vitro or in vivo. Heterologous moieties to accomplish these other objectives are known in the art.

As an alternative to expression of an Sp35 or TrkA antagonist fusion polypeptide, aptamer or antibody, a chosen heterologous moiety can be preformed and chemically conjugated to the Sp35 or TrkA antagonist polypeptide, aptamer or antibody. In most cases, a chosen heterologous moiety will function similarly, whether fused or conjugated to the Sp35 or TrkA antagonist polypeptide, aptamer or antibody. Therefore, in the following discussion of heterologous amino acid sequences, unless otherwise noted, it is to be understood that the heterologous sequence can be joined to the Sp35 or TrkA antagonist polypeptide, aptamer or antibody in the form of a fusion protein or as a chemical conjugate.

Pharmacologically active polypeptides such as Sp35 or TrkA antagonist polypeptides, aptamers or antibodies often exhibit rapid in vivo clearance, necessitating large doses to achieve therapeutically effective concentrations in the body. In addition, polypeptides smaller than about 60 kDa potentially undergo glomerular filtration, which sometimes leads to nephrotoxicity. Fusion or conjugation of relatively small polypeptides such as Sp35 or TrkA antagonist polypeptides, aptamers or antibodies can be employed to reduce or avoid the risk of such nephrotoxicity. Various heterologous amino acid sequences, i.e., polypeptide moieties or "carriers," for increasing the in vivo stability, i.e., serum half-life, of therapeutic polypeptides are known.

Due to its long half-life, wide in vivo distribution, and lack of enzymatic or immunological function, essentially full-length human serum albumin (HSA), or an HSA fragment, is commonly used as a heterologous moiety. Through application of methods and materials such as those taught in Yeh et al., *Proc. Natl. Acad. Sci. USA* 89:1904-08 (1992) and Syed et al., *Blood* 89:3243-52 (1997), HSA can be used to form an Sp35 or TrkA antagonist fusion polypeptide, aptamer, antibody or polypeptide/antibody conjugate that displays pharmacological activity by virtue of the Sp35 or TrkA moiety while displaying significantly increased in vivo stability, e.g., 10-fold to 100-fold higher. The C-terminus of the HSA can be fused to the N-terminus of the soluble Sp35 or TrkA moiety. Since HSA is a naturally secreted protein, the HSA signal sequence can be exploited to obtain secretion of the soluble Sp35 or TrkA fusion protein into the cell culture medium when the fusion protein is produced in a eukaryotic, e.g., mammalian, expression system.

In certain embodiments, Sp35 or TrkA antagonist polypeptides, aptamers, compounds, antibodies and antibody fragments thereof for use in the methods of the present invention further comprise a targeting moiety. Targeting moieties include a protein or a peptide which directs localization to a certain part of the body, for example, to the brain or compartments therein. In certain embodiments, Sp35 or TrkA antagonist polypeptides, aptamers, compounds, antibodies or antibody fragments thereof for use in the methods of the present invention are attached or fused to a brain targeting moiety. The brain targeting moieties are attached covalently (e.g., direct, translational fusion, or by chemical linkage either directly or through a spacer molecule, which can be optionally cleavable) or non-covalently attached (e.g., through reversible interactions such as avidin, biotin, protein A, IgG, etc.). In other embodiments, the Sp35 or TrkA antagonist polypeptides, aptamers, compounds, antibodies or antibody fragments thereof for use in the methods of the present invention are attached to one more brain targeting moieties. In additional embodiments, the brain targeting moiety is attached to a plurality of Sp35 or TrkA antagonist polypeptides, aptamers, compounds, antibodies or antibody fragments thereof for use in the methods of the present invention.

A brain targeting moiety associated with an Sp35 a or TrkA antagonist polypeptide, aptamer, compound, antibody or antibody fragment thereof enhances brain delivery of such an Sp35 or TrkA antagonist polypeptide, aptamer, compound, antibody or antibody fragment thereof. A number of polypeptides have been described which, when fused to a protein or therapeutic agent, delivers the protein or therapeutic agent through the blood brain barrier (BBB). Non-limiting examples include the single domain antibody FC5 (Abulrob et al. (2005) *J. Neurochem.* 95, 1201-1214); mAB 83-14, a monoclonal antibody to the human insulin receptor (Pardridge et al. (1995) *Pharmacol. Res.* 12, 807-816); the B2, B6 and B8 peptides binding to the human transferrin receptor (hTfR) (Xia et al. (2000) *J. Virol.* 74, 11359-11366); the OX26 monoclonal antibody to the transferrin receptor (Pardridge et al. (1991) *J. Pharmacol. Exp. Ther.* 259, 66-70); and SEQ ID NOs: 1-18 of U.S. Pat. No. 6,306,365. The contents of the above references are incorporated herein by reference in their entirety.

Enhanced brain delivery of an Sp35 or TrkA composition is determined by a number of means well established in the art. For example, administering to an animal a radioactively, enzymatically or fluorescently labeled Sp35 or TrkA antagonist polypeptide, aptamer, compound, antibody or antibody fragment thereof linked to a brain targeting moiety; determining brain localization; and comparing localization with an equivalent radioactively labeled Sp35 or TrkA antagonist polypeptide, aptamer, compound, antibody or antibody fragment thereof that is not associated with a brain targeting moiety. Other means of determining enhanced targeting are described in the above references.

The signal sequence is a polynucleotide that encodes an amino acid sequence that initiates transport of a protein across the membrane of the endoplasmic reticulum. Signal sequences useful for constructing an immunofusin include antibody light chain signal sequences, e.g., antibody 14.18 (Gillies et al., *J. Immunol. Meth.* 125:191-202 (1989)), antibody heavy chain signal sequences, e.g., the MOPC141 antibody heavy chain signal sequence (Sakano et al., *Nature* 286:5774 (1980)). Alternatively, other signal sequences can be used. See, e.g., Watson, *Nucl. Acids Res.* 12:5145 (1984). The signal peptide is usually cleaved in the lumen of the endoplasmic reticulum by signal peptidases. This results in the secretion of an immunofusin protein containing the Fc region and the soluble Sp35 or TrkA moiety.

In some embodiments, the DNA sequence may encode a proteolytic cleavage site between the secretion cassette and the Sp35 or TrkA moiety. Such a cleavage site may provide, e.g., for the proteolytic cleavage of the encoded fusion protein, thus separating the Fc domain from the target protein. Useful proteolytic cleavage sites include amino acid sequences recognized by proteolytic enzymes such as trypsin, plasmin, thrombin, factor Xa, or enterokinase K.

The secretion cassette can be incorporated into a replicable expression vector. Useful vectors include linear nucleic acids, plasmids, phagemids, cosmids and the like. An exemplary expression vector is pdC, in which the transcription of the immunofusin DNA is placed under the control of the enhancer and promoter of the human cytomegalovirus. See, e.g., Lo et al., *Biochim. Biophys. Acta* 1088:712 (1991); and Lo et al., *Protein Engineering* 11:495-500 (1998). An appropriate host cell can be transformed or transfected with a DNA that encodes a soluble Sp35 or TrkA polypeptide and used for the expression and secretion of the soluble Sp35 or TrkA polypeptide. Host cells that are typically used include immortal hybridoma cells, myeloma cells, 293 cells, Chinese hamster ovary (CHO) cells, HeLa cells, and COS cells.

In one embodiment, a soluble Sp35 or TrkA antagonist polypeptide is fused to a hinge and Fc region, i.e., the C-terminal portion of an Ig heavy chain constant region. Potential advantages of an Sp35-Fc of TrkA-Fc fusion include solubility, in vivo stability, and multivalency, e.g., dimerization. The Fc region used can be an IgA, IgD, or IgG Fc region (hinge-$C_H2$-$C_H3$). Alternatively, it can be an IgE or IgM Fc region (hinge-$C_H2$-$C_H3$-$C_H4$). An IgG Fc region is generally used, e.g., an $IgG_1$ Fc region or $IgG_4$ Fc region. In one embodiment, a sequence beginning in the hinge region just upstream of the papain cleavage site which defines IgG Fc chemically (i.e. residue 216, taking the first residue of heavy chain constant region to be 114 according to the Kabat system), or analogous sites of other immunoglobulins, is used in the fusion. The precise site at which the fusion is made is not critical; particular sites are well known and may be selected in order to optimize the biological activity, secretion, or binding characteristics of the molecule. Materials and Methods for constructing and expressing DNA encoding Fc fusions are known in the art and can be applied to obtain soluble Sp35 or TrkA fusions without undue experimentation. Some embodiments of the invention employ an Sp35 or TrkA fusion protein such as those described in Capon et al., U.S. Pat. Nos. 5,428,130 and 5,565,335.

Fully intact, wild-type Fc regions display effector functions that normally are unnecessary and undesired in an Fc fusion protein used in the methods of the present invention. Therefore, certain binding sites typically are deleted from the Fc region during the construction of the secretion cassette. For example, since coexpression with the light chain is unnecessary, the binding site for the heavy chain binding protein, Bip (Hendershot et al., *Immunol. Today* 8:111-14 (1987)), is deleted from the $C_H2$ domain of the Fc region of IgE, such that this site does not interfere with the efficient secretion of the immunofusin. Transmembrane domain sequences, such as those present in IgM, also are generally deleted.

The $IgG_1$ Fc region is most often used. Alternatively, the Fc region of the other subclasses of immunoglobulin gamma (gamma-2, gamma-3 and gamma-4) can be used in the secretion cassette. The $IgG_1$ Fc region of immunoglobulin gamma-1 is generally used in the secretion cassette and includes at least part of the hinge region, the $C_H2$ region, and the $C_H3$ region. In some embodiments, the Fc region of immunoglobulin gamma-1 is a $C_H2$-deleted-Fc, which includes part of the hinge region and the $C_H3$ region, but not the $C_H2$ region. A $C_H2$-deleted-Fc has been described by Gillies et al. (1990) *Hum. Antibod. Hybridomas* 1:47. In some embodiments, the Fc region of one of IgA, IgD, IgE, or IgM, is used.

Sp35-Fc or TrkA-Fc fusion proteins can be constructed in several different configurations. In one configuration the C-terminus of the soluble Sp35 or TrkA moiety is fused directly to the N-terminus of the Fc hinge moiety. In a slightly different configuration, a short polypeptide, e.g., 2-10 amino acids, is incorporated into the fusion between the N-terminus of the soluble Sp35 or TrkA moiety and the C-terminus of the Fc moiety. Such a linker provides conformational flexibility, which may improve biological activity in some circumstances. If a sufficient portion of the hinge region is retained in the Fc moiety, the Sp35-Fc or TrkA-Fc fusion will dimerize, thus forming a divalent molecule. A homogeneous population of monomeric Fc fusions will yield monospecific, bivalent dimers. A mixture of two monomeric Fc fusions each having a different specificity will yield bispecific, bivalent dimers.

Any of a number of cross-linkers that contain a corresponding amino-reactive group and thiol-reactive group can be used to link Sp35 or TrkA antagonist polypeptides to serum albumin. Examples of suitable linkers include amine reactive cross-linkers that insert a thiol-reactive maleimide, e.g., SMCC, AMAS, BMPS, MBS, EMCS, SMPB, SMPH, KMUS, and GMBS. Other suitable linkers insert a thiol-reactive haloacetate group, e.g., SBAP, SIA, SLAB. Linkers that provide a protected or non-protected thiol for reaction with sulfhydryl groups to product a reducible linkage include SPDP, SMPT, SATA, and SATP. Such reagents are commercially available (e.g., Pierce Chemicals).

Conjugation does not have to involve the N-terminus of a soluble Sp35 or TrkA polypeptide or the thiol moiety on serum albumin. For example, soluble Sp35-albumin or TrkA-albumin fusions can be obtained using genetic engineering techniques, wherein the soluble Sp35 or TrkA moiety is fused to the serum albumin gene at its N-terminus, C-terminus, or both.

Soluble Sp35 or TrkA polypeptides can be fused at the N- or C-terminus to heterologous peptides in order to facilitate purification or identification of the soluble Sp35 or TrkA moiety. For example, a histidine tag can be fused to a soluble Sp35 or TrkA polypeptide to facilitate purification using commercially available chromatography media. Additionally, an epitope tag enables soluble Sp35 or TrkA fusion polypeptides to be readily purified by affinity purification using an anti-tag antibody or another type of affinity matrix that binds to the epitope tag. Many examples of such purification tags are known in the art and include, but are not limited to, poly-histidine (poly-his) or poly-histidine-glycine (poly-his-gly) tags; the influenza hemmaglutinin (HA) tag polypeptide and its antibody 12CA5 (Field et al., Mol. Cell. Biol., 8:2159 2165 (1988)); the c-myc tag and the 8F9, 3C7, 6E10, G4, B7 and 9E10 antibodies thereto (Evan et al., Molecular and Cellular Biology, 5:3610 3616 (1985)); and the Herpes Simplex virus glycoprotein D (gD) tag and its antibody (Paborsky et al., Protein Engineering, 3(6):547 553 (1990)). Other tag polypeptides include the Flag-peptide (Hopp et al., BioTechnology, 6:1204 1210 (1988)); the KT3 epitope peptide (Martin et al., Science 255:192 194 (1992)); an α-tubulin epitope peptide (Skinner et al., J. Biol. Chem., 266:15163 15166 (1991)); and the T7 gene 10 protein peptide tag (Lutz-Freyermuth et al., Proc. Natl. Acad. Sci. USA, 87:6393 6397 (1990)). The tag can be any peptide epitope which is recognized by an antibody and does not interfere with the function of the soluble Sp35 or TrkA polypeptide.

In some embodiments of the invention, a soluble Sp35 or TrkA fusion construct is used to enhance the production of a soluble Sp35 or TrkA moiety in bacteria. In such constructs a bacterial protein normally expressed and/or secreted at a high level is employed as the N-terminal fusion partner of a soluble Sp35 or TrkA polypeptide. See, e.g., Smith et al., *Gene* 67:31 (1988); Hopp et al., *Biotechnology* 6:1204 (1988); LaVallie et al., *Biotechnology* 11:187 (1993).

By fusing a soluble Sp35 or TrkA moiety at the amino and carboxy termini of a suitable fusion partner, bivalent or tetravalent forms of a soluble Sp35 or TrkA polypeptide can be obtained. For example, a soluble Sp35 or TrkA moiety can be fused to the amino and carboxy termini of an Ig moiety to produce a bivalent monomeric polypeptide containing two soluble Sp35 or TrkA moieties. Upon dimerization of two of these monomers, by virtue of the Ig moiety, a tetravalent form of a soluble Sp35 or TrkA protein is obtained. Such multivalent forms can be used to achieve increased binding affinity for the target. Multivalent forms of soluble Sp35 or TrkA also can be obtained by placing soluble Sp35 or TrkA moieties in tandem to form concatamers, which can be employed alone or fused to a fusion partner such as Ig or HSA.

Conjugated Polymers (Other than Polypeptides)

Some embodiments of the invention involve a soluble Sp35 or TrkA polypeptide, Sp35 or TrkA aptamer, TrkA antagonist compound or Sp35 or TrkA antibody wherein one or more polymers are conjugated (covalently linked) to the Sp35 or TrkA polypeptide, compound, aptamer or antibody for use in the methods of the present invention. Examples of polymers suitable for such conjugation include polypeptides (discussed above), aptamers, sugar polymers and polyalkylene glycol chains. Typically, but not necessarily, a polymer is conjugated to the soluble Sp35 or TrkA polypeptide, aptamer, TrkA antagonist compound or Sp35 or TrkA antibody for the purpose of improving one or more of the following: solubility, stability, or bioavailability.

The class of polymer generally used for conjugation to a Sp35 or TrkA antagonist polypeptide, TrkA antagonist compound, aptamer or TrkA or Sp35 antibody is a polyalkylene glycol. Polyethylene glycol (PEG) is most frequently used. PEG moieties, e.g., 1, 2, 3, 4 or 5 PEG polymers, can be conjugated to each Sp35 or TrkA antagonist polypeptide, aptamer, or antibody, or TrkA antagonist compound to increase serum half life, as compared to the Sp35 or TrkA antagonist polypeptide, aptamer, compound or antibody alone. PEG moieties are non-antigenic and essentially biologically inert. PEG moieties used in the practice of the invention may be branched or unbranched.

The number of PEG moieties attached to the Sp35 or TrkA antagonist polypeptide, aptamer, compound or antibody and the molecular weight of the individual PEG chains can vary. In general, the higher the molecular weight of the polymer, the fewer polymer chains attached to the polypeptide. Usually, the total polymer mass attached to the Sp35 or TrkA antagonist polypeptide, compound, aptamer or antibody is from 20 kDa to 40 kDa. Thus, if one polymer chain is attached, the molecular weight of the chain is generally 20-40 kDa. If two chains are attached, the molecular weight of each chain is generally 10-20 kDa. If three chains are attached, the molecular weight is generally 7-14 kDa.

The polymer, e.g., PEG, can be linked to the Sp35 or TrkA antagonist polypeptide, aptamer or antibody through any suitable, exposed reactive group on the polypeptide. The exposed reactive group(s) can be, e.g., an N-terminal amino group or the epsilon amino group of an internal lysine residue, or both. An activated polymer can react and covalently link at any free amino group on the Sp35 or TrkA antagonist polypeptide, aptamer or antibody. Free carboxylic groups, suitably activated carbonyl groups, hydroxyl, guanidyl, imidazole, oxidized carbohydrate moieties and mercapto groups of the Sp35 or TrkA antagonist polypeptide, aptamer or antibody (if available) also can be used as reactive groups for polymer attachment.

In a conjugation reaction, from about 1.0 to about 10 moles of activated polymer per mole of polypeptide, depending on polypeptide concentration, is typically employed. Usually, the ratio chosen represents a balance between maximizing the reaction while minimizing side reactions (often non-specific) that can impair the desired pharmacological activity of the Sp35 or TrkA antagonist polypeptide or antibody. Preferably, at least 50% of the biological activity (as demonstrated, e.g., in any of the assays described herein or known in the art) of the Sp35 or TrkA antagonist polypeptide, aptamer or antibody is retained, and most preferably nearly 100% is retained.

The polymer can be conjugated to the Sp35 or TrkA antagonist polypeptide, aptamer or antibody using conventional chemistry. For example, a polyalkylene glycol moiety can be coupled to a lysine epsilon amino group of the Sp35 or TrkA antagonist polypeptide, aptamer or antibody. Linkage to the lysine side chain can be performed with an N-hydroxylsuccinimide (NHS) active ester such as PEG succinimidyl succinate (SS-PEG) and succinimidyl propionate (SPA-PEG). Suitable polyalkylene glycol moieties include, e.g., carboxymethyl-NHS and norleucine-NHS, SC. These reagents are commercially available. Additional amine-reactive PEG linkers can be substituted for the succinimidyl moiety. These include, e.g., isothiocyanates, nitrophenylcarbonates (PNP), epoxides, benzotriazole carbonates, SC-PEG, tresylate, aldehyde, epoxide, carbonylimidazole and PNP carbonate. Conditions are usually optimized to maximize the selectivity and extent of reaction. Such optimization of reaction conditions is within ordinary skill in the art.

PEGylation can be carried out by any of the PEGylation reactions known in the art. See, e.g., *Focus on Growth Factors* 3:4-10 (1992), and European patent applications EP 0 154 316 and EP 0 401 384. PEGylation may be carried out using an acylation reaction or an alkylation reaction with a reactive polyethylene glycol molecule (or an analogous reactive water-soluble polymer).

PEGylation by acylation generally involves reacting an active ester derivative of polyethylene glycol. Any reactive PEG molecule can be employed in the PEGylation. PEG esterified to N-hydroxysuccinimide (NHS) is a frequently used activated PEG ester. As used herein, "acylation" includes without limitation the following types of linkages between the therapeutic protein and a water-soluble polymer such as PEG: amide, carbamate, urethane, and the like. See, e.g., *Bioconjugate Chem.* 5:133-140, 1994. Reaction parameters are generally selected to avoid temperature, solvent, and pH conditions that would damage or inactivate the soluble Sp35 or TrkA polypeptide, aptamer or antibody.

Generally, the connecting linkage is an amide and typically at least 95% of the resulting product is mono-, di- or tri-PEGylated. However, some species with higher degrees of PEGylation may be formed in amounts depending on the specific reaction conditions used. Optionally, purified PEGylated species are separated from the mixture, particularly unreacted species, by conventional purification methods, including, e.g., dialysis, salting-out, ultrafiltration, ion-exchange chromatography, gel filtration chromatography, hydrophobic exchange chromatography, and electrophoresis.

PEGylation by alkylation generally involves reacting a terminal aldehyde derivative of PEG with Sp35 or TrkA antagonist polypeptide, aptamer or antibody in the presence of a reducing agent. In addition, one can manipulate the reaction conditions to favor PEGylation substantially only at the N-terminal amino group of Sp35 or TrkA antagonist polypeptide, aptamer or antibody, i.e. a mono-PEGylated protein. In either case of mono-PEGylation or poly-PEGylation, the PEG groups are typically attached to the protein via a —$CH_2$—NH— group. With particular reference to the —$CH_2$— group, this type of linkage is known as an "alkyl" linkage.

Derivatization via reductive alkylation to produce an N-terminally targeted mono-PEGylated product exploits differential reactivity of different types of primary amino groups (lysine versus the N-terminal) available for derivatization.

The reaction is performed at a pH that allows one to take advantage of the pKa differences between the epsilon-amino groups of the lysine residues and that of the N-terminal amino group of the protein. By such selective derivatization, attachment of a water-soluble polymer that contains a reactive group, such as an aldehyde, to a protein is controlled: the conjugation with the polymer takes place predominantly at the N-terminus of the protein and no significant modification of other reactive groups, such as the lysine side chain amino groups, occurs.

The polymer molecules used in both the acylation and alkylation approaches are selected from among water-soluble polymers. The polymer selected is typically modified to have a single reactive group, such as an active ester for acylation or an aldehyde for alkylation, so that the degree of polymerization may be controlled as provided for in the present methods. An exemplary reactive PEG aldehyde is polyethylene glycol propionaldehyde, which is water stable, or mono C1-C10 alkoxy or aryloxy derivatives thereof (see, e.g., Harris et al., U.S. Pat. No. 5,252,714). The polymer may be branched or unbranched. For the acylation reactions, the polymer(s) selected typically have a single reactive ester group. For reductive alkylation, the polymer(s) selected typically have a single reactive aldehyde group. Generally, the water-soluble polymer will not be selected from naturally occurring glycosyl residues, because these are usually made more conveniently by mammalian recombinant expression systems.

Methods for preparing a PEGylated soluble Sp35 or TrkA polypeptide, aptamer or antibody generally includes the steps of (a) reacting a Sp35 or TrkA antagonist polypeptide, aptamer or antibody with polyethylene glycol (such as a reactive ester or aldehyde derivative of PEG) under conditions whereby the molecule becomes attached to one or more PEG groups, and (b) obtaining the reaction product(s). In general, the optimal reaction conditions for the acylation reactions will be determined case-by-case based on known parameters and the desired result. For example, a larger ratio of PEG to protein generally leads to a greater the percentage of poly-PEGylated product.

Reductive alkylation to produce a substantially homogeneous population of mono-polymer/soluble Sp35 or TrkA polypeptide, Sp35 or TrkA aptamer or Sp35 or TrkA antibody generally includes the steps of: (a) reacting a soluble Sp35 or TrkA protein or polypeptide with a reactive PEG molecule under reductive alkylation conditions, at a pH suitable to pen-nit selective modification of the N-terminal amino group of the polypeptide or antibody; and (b) obtaining the reaction product(s).

For a substantially homogeneous population of mono-polymer/soluble Sp35 or TrkA polypeptide, Sp35 or TrkA aptamer or Sp35 or TrkA antibody, the reductive alkylation reaction conditions are those that permit the selective attachment of the water-soluble polymer moiety to the N-terminus of the polypeptide or antibody. Such reaction conditions generally provide for pKa differences between the lysine side chain amino groups and the N-terminal amino group. For purposes of the present invention, the pH is generally in the range of 3-9, typically 3-6.

Soluble Sp35 or TrkA polypeptides, aptamers or antibodies can include a tag, e.g., a moiety that can be subsequently released by proteolysis. Thus, the lysine moiety can be selectively modified by first reacting a His-tag modified with a low-molecular-weight linker such as Traut's reagent (Pierce) which will react with both the lysine and N-terminus, and then releasing the His tag. The polypeptide will then contain a free SH group that can be selectively modified with a PEG containing a thiol-reactive head group such as a maleimide group, a vinylsulfone group, a haloacetate group, or a free or protected SH.

Traut's reagent can be replaced with any linker that will set up a specific site for PEG attachment. For example, Traut's reagent can be replaced with SPDP, SMPT, SATA, or SATP (Pierce). Similarly, one could react the protein with an amine-reactive linker that inserts a maleimide (for example SMCC, AMAS, BMPS, MBS, EMCS, SMPB, SMPH, KMUS, or GMBS), a haloacetate group (SBAP, SIA, SIAB), or a vinylsulfone group and react the resulting product with a PEG that contains a free SH.

In some embodiments, the polyalkylene glycol moiety is coupled to a cysteine group of the Sp35 or TrkA antagonist polypeptide, aptamer or antibody for use in the methods of the present invention. Coupling can be effected using, e.g., a maleimide group, a vinylsulfone group, a haloacetate group, or a thiol group.

Optionally, the soluble Sp35 or TrkA polypeptide, aptamer or antibody is conjugated to the polyethylene-glycol moiety through a labile bond. The labile bond can be cleaved in, e.g., biochemical hydrolysis, proteolysis, or sulfhydryl cleavage. For example, the bond can be cleaved under in vivo (physiological) conditions.

The reactions may take place by any suitable method used for reacting biologically active materials with inert polymers, generally at about pH 5-8, e.g., pH 5, 6, 7, or 8, if the reactive groups are on the alpha amino group at the N-terminus. Generally the process involves preparing an activated polymer and thereafter reacting the protein with the activated polymer to produce the soluble protein suitable for formulation.

Sp35 or TrkA Polynucleotide Antagonists

Sp35 or TrkA antagonists in the methods of the present invention include an Sp35 or TrkA polynucleotide antagonist which comprises a nucleic acid molecule which specifically binds to a polynucleotide which encodes Sp35 or TrkA. The Sp35 or TrkA polynucleotide antagonist prevents expression of Sp35 or TrkA (knockdown). Sp35 or TrkA polynucleotide antagonists include, but are not limited to antisense molecules, ribozymes, siRNA, shRNA, RNAi. Typically, such binding molecules are separately administered to the animal (see, for example, O'Connor, *J. Neurochem.* 56:560 (1991), but such binding molecules may also be expressed in vivo from polynucleotides taken up by a host cell and expressed in vivo. See also *Oligodeoxynucleotides as Antisense Inhibitors of Gene Expression*, CRC Press, Boca Raton, Fla. (1988).

RNAi refers to the expression of an RNA which interferes with the expression of the targeted mRNA. Specifically, the RNAi silences a targeted gene via interacting with the specific mRNA (e.g. Sp35 or TrkA) through an siRNA (short interfering RNA). The ds RNA complex is then targeted for degradation by the cell. Additional RNAi molecules include short hairpin RNA (shRNA); also short interfering hairpin. The shRNA molecule contains sense and antisense sequences from a target gene connected by a loop. The shRNA is transported from the nucleus into the cytoplasm, it is degraded along with the mRNA. Pol III or U6 promoters can be used to express RNAs for RNAi. In some embodiments of the invention, the shRNA is expressed from a lentiviral vector (e.g. pLL3.7).

RNAi is mediated by double stranded RNA (dsRNA) molecules that have sequence-specific homology to their "target" mRNAs (Caplen et al., *Proc Natl Acad Sci USA* 98:9742-9747, 2001). Biochemical studies in *Drosophila* cell-free lysates indicates that the mediators of RNA-dependent gene silencing are 21-25 nucleotide "small interfering" RNA duplexes (siRNAs). Accordingly, siRNA molecules are advantageously used in the methods of the present invention. The siRNAs are derived from the processing of dsRNA by an RNase known as DICER (Bernstein et al., *Nature* 409:363-366, 2001). It appears that siRNA duplex products are recruited into a multi-protein siRNA complex termed RISC (RNA Induced Silencing Complex). Without wishing to be bound by any particular theory, it is believed that a RISC is guided to a target mRNA, where the siRNA duplex interacts sequence-specifically to mediate cleavage in a catalytic fashion (Bernstein et al., *Nature* 409:363-366, 2001; Boutla et al., *Curr Biol* 11:1776-1780, 2001).

RNAi has been used to analyze gene function and to identify essential genes in mammalian cells (Elbashir et al., *Methods* 26:199-213, 2002; Harborth et al., *J Cell Sci* 114:4557-4565, 2001), including by way of non-limiting example neurons (Krichevsky et al., *Proc Natl Acad Sci USA* 99:11926-11929, 2002). RNAi is also being evaluated for therapeutic modalities, such as inhibiting or blocking the infection, replication and/or growth of viruses, including without limitation poliovirus (Gitlin et al., *Nature* 418:379-380, 2002) and HIV (Capodici et al., *J Immunol* 169:5196-5201, 2002), and reducing expression of oncogenes (e.g., the bcr-abl gene; Scherr et al., *Blood* 101(4):1566-9, 2002). RNAi has been used to modulate gene expression in mammalian (mouse) and amphibian (*Xenopus*) embryos (respectively, Calegari et al., *Proc Natl Acad Sci USA* 99:14236-14240, 2002; and Zhou, et al., *Nucleic Acids Res* 30:1664-1669, 2002), and in postnatal mice (Lewis et al., *Nat Genet.* 32:107-108, 2002), and to reduce transgene expression in adult transgenic mice (McCaffrey et al., *Nature* 418:38-39, 2002). Methods have been described for determining the efficacy and specificity of siRNAs in cell culture and in vivo (see, e.g., Bertrand et al., *Biochem Biophys Res Commun* 296:1000-1004, 2002; Lassus et al., *Sci STKE* 2002(147): PL13, 2002; and Leirdal et al., *Biochem Biophys Res Commun* 295:744-748, 2002).

Molecules that mediate RNAi, including without limitation siRNA, can be produced in vitro by chemical synthesis (Hohjoh, *FEBS Lett* 521:195-199, 2002), hydrolysis of dsRNA (Yang et al., *Proc Natl Acad Sci USA* 99:9942-9947, 2002), by in vitro transcription with T7 RNA polymerase (Donzeet et al., *Nucleic Acids Res* 30:e46, 2002; Yu et al., *Proc Natl Acad Sci USA* 99:6047-6052, 2002), and by hydrolysis of double-stranded RNA using a nuclease such as *E. coli* RNase III (Yang et al., *Proc Natl Acad Sci USA* 99:9942-9947, 2002).

siRNA molecules may also be formed by annealing two oligonucleotides to each other, typically have the following general structure, which includes both double-stranded and single-stranded portions:

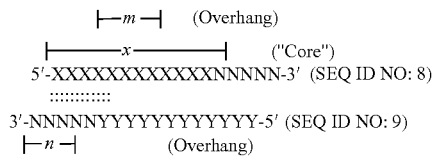

Wherein N, X and Y are nucleotides; X hydrogen bonds to Y; ":" signifies a hydrogen bond between two bases; x is a natural integer having a value between 1 and about 100; and m and n are whole integers having, independently, values between 0 and about 100. In some embodiments, N, X and Y are independently A, G, C and T or U. Non-naturally occurring bases and nucleotides can be present, particularly in the case of synthetic siRNA (i.e., the product of annealing two oligonucleotides). The double-stranded central section is called the "core" and has base pairs (bp) as units of measurement; the single-stranded portions are overhangs, having nucleotides (nt) as units of measurement. The overhangs shown are 3' overhangs, but molecules with 5' overhangs are also within the scope of the invention. Also within the scope of the invention are siRNA molecules with no overhangs (i.e., m=0 and n=0), and those having an overhang on one side of the core but not the other (e.g., m=0 and n≥1, or vice-versa).

Initially, RNAi technology did not appear to be readily applicable to mammalian systems. This is because, in mammals, dsRNA activates dsRNA-activated protein kinase (PKR) resulting in an apoptotic cascade and cell death (Der et al, *Proc. Natl. Acad. USA* 94:3279-3283, 1997). In addition, it has long been known that dsRNA activates the interferon cascade in mammalian cells, which can also lead to altered cell physiology (Colby et al, *Annu. Rev. Microbiol.* 25:333, 1971; Kleinschmidt et al., *Annu. Rev. Biochem.* 41:517, 1972; Lampson et al., *Proc. Natl. Acad. Sci. USA* 58L782, 1967; Lomniczi et al., *J. Gen. Virol.* 8:55, 1970; and Younger et al., *J. Bacteriol.* 92:862, 1966). However, dsRNA-mediated activation of the PKR and interferon cascades requires dsRNA longer than about 30 base pairs. In contrast, dsRNA less than 30 base pairs in length has been demonstrated to cause RNAi in mammalian cells (Caplen et al., *Proc. Natl. Acad. Sci. USA* 98:9742-9747, 2001). Thus, it is expected that undesirable, non-specific effects associated with longer dsRNA molecules can be avoided by preparing short RNA that is substantially free from longer dsRNAs.

References regarding siRNA: Bernstein et al., *Nature* 409: 363-366, 2001; Boutla et al., *Curr Biol* 11:1776-1780, 2001; Cullen, *Nat Immunol.* 3:597-599, 2002; Caplen et al., *Proc Natl Acad Sci USA* 98:9742-9747, 2001; Hamilton et al., *Science* 286:950-952, 1999; Nagase et al., *DNA Res.* 6:63-70, 1999; Napoli et al., *Plant Cell* 2:279-289, 1990; Nicholson et al., *Mamm. Genome* 13:67-73, 2002; Parrish et al., *Mol Cell* 6:1077-1087, 2000; Romano et al., *Mol Microbiol* 6:3343-3353, 1992; Tabara et al., *Cell* 99:123-132, 1999; and Tuschl, *Chembiochem.* 2:239-245, 2001.

Paddison et al. (*Genes & Dev.* 16:948-958, 2002) have used small RNA molecules folded into hairpins as a means to effect RNAi. Accordingly, such short hairpin RNA (shRNA) molecules are also advantageously used in the methods of the invention. The length of the stem and loop of functional shRNAs varies; stem lengths can range anywhere from about 25 to about 30 nt, and loop size can range between 4 to about 25 nt without affecting silencing activity. While not wishing to be bound by any particular theory, it is believed that these shRNAs resemble the dsRNA products of the DICER RNase and, in any event, have the same capacity for inhibiting expression of a specific gene.

Antisense technology can be used to control gene expression through antisense DNA or RNA, or through triple-helix formation. Antisense techniques are discussed, for example, in Okano, *J. Neurochem.* 56:560 (1991); Oligodeoxynucleotides as Antisense Inhibitors of Gene Expression, CRC Press, Boca Raton, Fla. (1988). Triple helix formation is discussed in, for instance, Lee et al., *Nucleic Acids Research* 6:3073 (1979); Cooney et al., *Science* 241:456 (1988); and Dervan et al., *Science* 251:1300 (1991). The methods are based on binding of a polynucleotide to a complementary DNA or RNA.

For example, the 5' coding portion of a polynucleotide that encodes Sp35 may be used to design an antisense RNA oligonucleotide of from about 10 to 40 base pairs in length. A DNA oligonucleotide is designed to be complementary to a region of the gene involved in transcription, thereby preventing transcription and the production of the target protein. The antisense RNA oligonucleotide hybridizes to the mRNA in vivo and blocks translation of the mRNA molecule into the target polypeptide.

In one embodiment, antisense nucleic acids specific for the Sp35 or TrkA gene are produced intracellularly by transcription from, an exogenous sequence. For example, a vector or a portion thereof, is transcribed, producing an antisense nucleic acid (RNA). Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the antisense molecule, can be by any promoter known in the art to act in vertebrate, preferably human cells, such as those described elsewhere herein.

Absolute complementarity of an antisense molecule, although preferred, is not required. A sequence complementary to at least a portion of an RNA encoding Sp35 or TrkA means a sequence having sufficient complementarity to be able to hybridize with the RNA, forming a stable duplex; or triplex formation may be assayed. The ability to hybridize will depend on both the degree of complementarity and the length of the antisense nucleic acid. Generally, the larger the hybridizing nucleic acid, the more base mismatches it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of a messenger RNA, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See, generally, Wagner, R., Nature 372:333-335 (1994). Thus, oligonucleotides complementary to either the 5'- or 3'-non-translated, non-coding regions could be used in an antisense approach to inhibit translation of Sp35. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

In yet another embodiment, an antisense oligonucleotide for use in the methods disclosed herein is an α-anomeric oligonucleotide. An α-anomeric oligonucleotide forms specific double-stranded hybrids with complementary RNA in which, contrary to the usual situation, the strands run parallel to each other (Gautier et al., Nucl. Acids Res. 15:6625-6641 (1987)). The oligonucleotide is a 2'-0-methylribonucleotide (Inoue et al., Nucl. Acids Res. 15:6131-6148 (1987)), or a chimeric RNA-DNA analogue (Inoue et al., FEBS Lett. 215: 327-330 (1987)).

Polynucleotide compositions for use in the methods disclosed herein further include catalytic RNA, or a ribozyme (See, e.g., PCT International Publication WO 90/11364, published Oct. 4, 1990; Sarver et al., Science 247:1222-1225 (1990). The use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature 334:585-591 (1988). Preferably, the ribozyme is engineered so that the cleavage recognition site is located near the 5' end of the target mRNA; i.e., to increase efficiency and minimize the intracellular accumulation of non-functional mRNA transcripts.

As in the antisense approach, ribozymes for use in the methods disclosed herein can be composed of modified oligonucleotides (e.g. for improved stability, targeting, etc.) and may be delivered to cells which express Sp35 or TrkA in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous Sp35 or TrkA messages and inhibit translation. Since ribozymes, unlike antisense molecules, are catalytic, a lower intracellular concentration is required for efficiency.

Polynucleotides for use in the methods disclosed herein, including aptamers described supra, can be DNA or RNA or chimeric mixtures or derivatives or modified versions thereof, single-stranded or double-stranded. The polynucleotide can be modified at the base moiety, sugar moiety, or phosphate backbone, for example, to improve stability of the molecule, hybridization, etc. The polynucleotide may include other appended groups such as peptides (e.g., for targeting host cell receptors in vivo), or agents facilitating transport across the cell membrane (see, e.g., Letsinger et al., Proc. Natl. Acad. Sci. U.S.A. 86:6553-6556 (1989); Lemaitre et al., Proc. Natl. Acad. Sci. 84:648-652 (1987)); PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., BioTechniques 6:958-976 (1988)) or intercalating agents. (See, e.g., Zon, Pharm. Res. 5:539-549 (1988)). To this end, the polynucleotide may be conjugated to another molecule, e.g., a peptide, hybridization triggered cross-linking agent, transport agent, hybridization-triggered cleavage agent, etc.

Polynucleotides, including aptamers, for use in the methods disclosed herein may comprise at least one modified base moiety which is selected from the group including, but not limited to, 5fluorouracil, 5-bromouracil, 5-chlorouracil, 5-iodouracil, hypoxanthine, xaritine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N-6-isopentenyladenine, 1-methylguanine, 1-methylinosine, 2,2-dimethylguanine, 2-methyladenine, 2-methylguanine, 3-methylcytosine, 5-methylcytosine, N-6-adenine, 7-methylguanine, 5-methylaminomethyluracil, 5-methoxyaminomethyl-2-thiouracil, beta-D-mannosylqueosine, 5' methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3(3-amino-3-N2-carboxypropyl) uracil, (acp3)w, and 2,6-diaminopurine.

Polynucleotides, including aptamers, for use in the methods disclosed herein may also comprise at least one modified sugar moiety selected from the group including, but not limited to, arabinose, 2-fluoroarabinose, xylulose, and hexose.

In yet another embodiment, a polynucleotide, including an aptamer, for use in the methods disclosed herein comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

Polynucleotides, including aptamers, for use in the methods of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al., *Nucl. Acids Res.* 16:3209 (1988), methylphosphonate oligonucleotides can be prepared by use of controlled pore glass polymer supports (Sarin et al., *Proc. Natl. Acad. Sci. U.S.A.* 85:7448-7451 (1988)), etc.

Vectors

Vectors comprising nucleic acids encoding Sp35 or TrkA antagonists may also be used to produce antagonists for use in the methods of the invention. The choice of vector and expression control sequences to which such nucleic acids are operably linked depends on the functional properties desired, e.g., protein expression, and the host cell to be transformed.

Expression control elements useful for regulating the expression of an operably linked coding sequence are known in the art. Examples include, but are not limited to, inducible promoters, constitutive promoters, secretion signals, and other regulatory elements. When an inducible promoter is used, it can be controlled, e.g., by a change in nutrient status, or a change in temperature, in the host cell medium.

The vector can include a prokaryotic replicon, i.e., a DNA sequence having the ability to direct autonomous replication and maintenance of the recombinant DNA molecule extrachromosomally in a bacterial host cell. Such replicons are well known in the art. In addition, vectors that include a prokaryotic replicon may also include a gene whose expression confers a detectable marker such as a drug resistance. Examples of bacterial drug-resistance genes are those that confer resistance to ampicillin or tetracycline.

Vectors that include a prokaryotic replicon can also include a prokaryotic or bacteriophage promoter for directing expression of the coding gene sequences in a bacterial host cell. Promoter sequences compatible with bacterial hosts are typically provided in plasmid vectors containing convenient restriction sites for insertion of a DNA segment to be expressed. Examples of such plasmid vectors are pUC8, pUC9, pBR322 and pBR329 (BioRad), pPL and pKK223 (Pharmacia). Any suitable prokaryotic host can be used to express a recombinant DNA molecule encoding a protein used in the methods of the invention.

For the purposes of this invention, numerous expression vector systems may be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. The neomycin phosphotransferase (neo) gene is an example of a selectable marker gene (Southern et al., *J. Mol. Anal. Genet.* 1:327-341 (1982)). Additional elements may also be needed for optimal synthesis of mRNA. These elements may include signal sequences or splice signals, as well as transcriptional promoters, enhancers, and termination signals.

In one embodiment, an expression vector referred to as NEOSPLA (U.S. Pat. No. 6,159,730, incorporated herein by reference) may be used. This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence. This vector has been found to result in very high-level expression upon transfection in CHO cells, followed by selection in G418-containing medium and methotrexate amplification. Of course, any expression vector which is capable of eliciting expression in eukaryotic cells may be used in the present invention. Examples of suitable vectors include, but are not limited to, plasmids pcDNA3, pHCMV/Zeo, pCR3.1, pEF1/His, pIND/GS, pRc/HCMV2, pSV40/Zeo2, pTRACER-HCMV, pUB6N5-His, pVAX1, and pZeoSV2 (available from Invitrogen, San Diego, Calif.), and plasmid pCI (available from Promega, Madison, Wis.). Additional eukaryotic cell expression vectors are known in the art and are commercially available. Typically, such vectors contain convenient restriction sites for insertion of the desired DNA segment. Exemplary vectors include pSVL and pKSV-10 (Pharmacia), pBPV-1, pml2d (International Biotechnologies), pTDT1 (ATCC 31255), retroviral expression vector pMIG and pLL3.7, adenovirus shuttle vector pDC315, and AAV vectors. Other exemplary vector systems are disclosed e.g., in U.S. Pat. No. 6,413,777.

In general, screening large numbers of transformed cells for those which express suitably high levels of the antagonist is routine experimentation which can be carried out, for example, by robotic systems.

Frequently used regulatory sequences for mammalian host cell expression include viral elements that direct high levels of protein expression in mammalian cells, such as promoters and enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdmlP)), polyoma and strong mammalian promoters such as native immunoglobulin and actin promoters. For further description of viral regulatory elements, and sequences thereof, see, e.g., Stinski, U.S. Pat. No. 5,168,062; Bell, U.S. Pat. No. 4,510,245; and Schaffner, U.S. Pat. No. 4,968,615.

The recombinant expression vectors may carry sequences that regulate replication of the vector in host cells (e.g., origins of replication) and selectable marker genes. The selectable marker gene facilitates selection of host cells into which the vector has been introduced (see, e.g., Axel, U.S. Pat. Nos. 4,399,216; 4,634,665 and 5,179,017). For example, typically the selectable marker gene confers resistance to a drug, such as G418, hygromycin or methotrexate, on a host cell into which the vector has been introduced. Frequently used selectable marker genes include the dihydrofolate reductase (DHFR) gene (for use in dhfr-host cells with methotrexate selection/amplification) and the neo gene (for G418 selection).

Vectors encoding Sp35 or TrkA antagonists can be used for transformation of a suitable host cell. Transformation can be by any suitable method. Methods for introduction of exogenous DNA into mammalian cells are well known in the art and include dextran-mediated transfection, calcium phosphate precipitation, polybrene-mediated transfection, protoplast fusion, electroporation, transfection via encapsulation of the polynucleotide(s) in liposomes, and direct microinjection of the DNA into nuclei. In addition, nucleic acid molecules may be introduced into mammalian cells by viral vectors. Mammalian cells may also be transduced by recombinant viruses containing the exogenous DNA which is to be introduced into the mammalian cells.

Transformation of host cells can be accomplished by conventional methods suited to the vector and host cell employed. For transformation of prokaryotic host cells, electroporation and salt treatment methods can be employed (Cohen et al., *Proc. Natl. Acad. Sci. USA* 69:2110-14 (1972)). For transformation of vertebrate cells, electroporation, cationic lipid or salt treatment methods can be employed. See, e.g., Graham et al., *Virology* 52:456-467 (1973); Wigler et al., *Proc. Natl. Acad. Sci. USA* 76:1373-76 (1979).

The host cell line used for protein expression is most preferably of mammalian origin; those skilled in the art are credited with ability to preferentially determine particular host cell lines which are best suited for the desired gene product to be expressed therein. Exemplary host cell lines include, but are not limited to, NSO, SP2 cells, baby hamster kidney (BHK) cells, monkey kidney cells (COS), human hepatocellular carcinoma cells (e.g., Hep G2), A549 cells DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), P3×63-Ag3.653 (mouse myeloma), BFA-1c1BPT (bovine endothelial cells), RAJI (human lymphocyte) and 293 (human kidney). Host cell lines are typically available from commercial services, the American Tissue Culture Collection or from published literature.

Expression of polypeptides from production cell lines can be enhanced using known techniques. For example, the glutamine synthetase (GS) system is commonly used for enhancing expression under certain conditions. See, e.g., European Patent Nos. 0 216 846, 0 256 055, and 0 323 997 and European Patent Application No. 89303964.4.

Host Cells

Host cells for expression of an Sp35 or TrkA antagonist for use in a method of the invention may be prokaryotic or eukaryotic. Exemplary eukaryotic host cells include, but are not limited to, yeast and mammalian cells, e.g., Chinese hamster ovary (CHO) cells (ATCC Accession No. CCL61), NIH Swiss mouse embryo cells NIH-3T3 (ATCC Accession No. CRL1658), and baby hamster kidney cells (BHK). Other useful eukaryotic host cells include insect cells and plant cells. Exemplary prokaryotic host cells are *E. coli* and *Streptomyces*.

Gene Therapy

An Sp35 and certain TrkA antagonist (e.g. antagonist polynucleotide, polypeptide, antibodies and aptamers) can be produced in vivo in a mammal, e.g., a human patient, using a gene-therapy approach to treatment of a disease, disorder or injury associated with DA neuronal degeneration, death or lack or regeneration. This involves administration of a suitable Sp35 or TrkA antagonist-encoding nucleic acid operably linked to suitable expression control sequences. Generally, these sequences are incorporated into a viral vector. Suitable viral vectors for such gene therapy include an adenoviral vector, an alphavirus vector, an enterovirus vector, a pestivirus vector, a lentiviral vector, a baculoviral vector, a herpesvirus vector, an Epstein Barr viral vector, a papovaviral vector, a poxvirus vector, a vaccinia viral vector, an adeno-associated viral vector and a herpes simplex viral vector. The viral vector can be a replication-defective viral vector. Adenoviral vectors that have a deletion in their E1 gene or E3 genes are typically used. When an adenoviral vector is used, the vector usually does not have a selectable marker gene.

Pharmaceutical Compositions and Administrative Methods

The Sp35 or TrkA antagonists used in the methods of the invention may be formulated into pharmaceutical compositions for administration to mammals, including humans. The pharmaceutical compositions used in the methods of this invention comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions used in the methods of the present invention may be administered by any suitable method, e.g., parenterally, intraventricularly, orally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. As described previously, Sp35 or TrkA antagonists used in the methods of the invention act in the nervous system to promote survival and myelination of neurons. Accordingly, in the methods of the invention, the Sp35 or TrkA antagonists are administered in such a way that they cross the blood-brain barrier. This crossing can result from the physico-chemical properties inherent in the Sp35 or TrkA antagonist molecule itself, from other components in a pharmaceutical formulation, or from the use of a mechanical device such as a needle, cannula or surgical instruments to breach the blood-brain barrier. Where the Sp35 or TrkA antagonist is a molecule that does not inherently cross the blood-brain barrier, e.g., a fusion to a moiety that facilitates the crossing, suitable routes of administration are, e.g., intrathecal or intracranial, e.g., directly into a chronic lesion of MS. Where the Sp35 or TrkA antagonist is a molecule that inherently crosses the blood-brain barrier, the route of administration may be by one or more of the various routes described below.

Sterile injectable forms of the compositions used in the methods of this invention may be aqueous or oleaginous suspension. These suspensions may be formulated according to techniques known in the art using suitable dispersing or wetting agents and suspending agents. The sterile, injectable preparation may also be a sterile, injectable solution or suspension in a non-toxic parenterally acceptable diluent or solvent, for example as a suspension in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Parenteral formulations may be a single bolus dose, an infusion or a loading bolus dose followed with a maintenance dose. These compositions may be administered at specific fixed or variable intervals, e.g., once a day, or on an "as needed" basis.

Certain pharmaceutical compositions used in the methods of this invention may be orally administered in an acceptable dosage form including, e.g., capsules, tablets, aqueous suspensions or solutions. Certain pharmaceutical compositions also may be administered by nasal aerosol or inhalation. Such compositions may be prepared as solutions in saline, employing benzyl alcohol or other suitable preservatives, absorption promoters to enhance bioavailability, and/or other conventional solubilizing or dispersing agents.

The amount of an Sp35 or TrkA antagonist that may be combined with the carrier materials to produce a single dosage form will vary depending upon the host treated, the type of antagonist used and the particular mode of administration. The composition may be administered as a single dose, multiple doses or over an established period of time in an infusion. Dosage regimens also may be adjusted to provide the optimum desired response (e.g., a therapeutic or prophylactic response).

The methods of the invention use a "therapeutically effective amount" or a "prophylactically effective amount" of an Sp35 or TrkA antagonist. Such a therapeutically or prophylactically effective amount may vary according to factors such as the disease state, age, sex, and weight of the individual. A therapeutically or prophylactically effective amount is also one in which any toxic or detrimental effects are outweighed by the therapeutically beneficial effects.

A specific dosage and treatment regimen for any particular patient will depend upon a variety of factors, including the particular Sp35 or TrkA antagonist used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinetic principles well known in the art.

In the methods of the invention the Sp35 or TrkA antagonists are generally administered directly to the nervous system, intracerebroventricularly, or intrathecally, e.g. into a chronic lesion of MS. Compositions for administration according to the methods of the invention can be formulated so that a dosage of 0.001-10 mg/kg body weight per day of the Sp35 antagonist polypeptide is administered. In some embodiments of the invention, the dosage is 0.01-1.0 mg/kg body weight per day. In some embodiments, the dosage is 0.001-0.5 mg/kg body weight per day.

For treatment with an Sp35 or TrkA antagonist antibody, the dosage can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example, dosages can be 1 mg/kg body weight or 10 mg/kg body weight or within the range of 1-10 mg/kg, preferably at least 1 mg/kg. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated.

In certain embodiments, a subject can be treated with a nucleic acid molecule encoding a Sp35 or TrkA antagonist polynucleotide. Doses for nucleic acids range from about 10 ng to 1 g, 100 ng to 100 mg, 1 µg to 10 mg, or 30-300 µg DNA per patient. Doses for infectious viral vectors vary from 10-100, or more, virions per dose.

In certain embodiments, TrkA antagonists may be administered in an amount effective to promote myelination of CNS neuron by an increase in the amount of myelin proteins (e.g. MBP and MAG) of at least 5%, 10%, 20%, 25%, 30%, 40%, 50%, 60%, 70%, 75%, 80%, 85%, 90%, 95%, 100%, 110%, 120%, 130%, 140%, 150%, 160%, 170%, 180%, 190%, 200%, 250%, 300%, 350%, 400%, 450%, 500%, 550%, 600%, 650%, 700%, 750%, 800%, 850%, 900%, 950%, or 1000% as compared to the level of myelin proteins of an untreated CNS neuron or mammal.

In certain embodiments, TrkA antagonists may be administered in an amount effective to promote survival of a CNS neuron by an increase in the number of surviving neurons of at least 5%, 10%, 20%, 25%, 30%, 40%, 50%, 60%, 70%, 75%, 80%, 85%, 90%, 95%, 100%, 110%, 120%, 130%, 140%, 150%, 160%, 170%, 180%, 190%, 200%, 250%, 300%, 350%, 400%, 450%, 500%, 550%, 600%, 650%, 700%, 750%, 800%, 850%, 900%, 950%, or 1000% as compared to the number of surviving neurons in an untreated CNS neuron or mammal.

In certain embodiments, TrkA antagonists may be administered in an amount effective to inhibit or decrease Sp35 expression by at least 5%, 10%, 20%, 25%, 30%, 40%, 50%, 60%, 70%, 75%, 80%, 85%, 90%, 95% or 100% as compared to Sp35 expression in an untreated CNS neuron, oligodendrocyte or mammal.

In certain embodiments, Sp35 antagonists may be administered in an amount effective to block interaction of Sp35 and TrkA by at least 5%, 10%, 20%, 25%, 30%, 40%, 50%, 60%, 70%, 75%, 80%, 85%, 90%, 95% or 100% as measured by a competition assay or immunoprecipitation assay as compared to the interaction of Sp35 and TrkA in the absence of Sp35 antagonists.

In certain embodiments, Sp35 antagonists may be administered in an amount effective to inhibit phosphorylation of TrkA by at least 5%, 10%, 20%, 25%, 30%, 40%, 50%, 60%, 70%, 75%, 80%, 85%, 90%, 95% or 100% as compared to the amount of phosphorylated TrkA in an untreated CNS neuron, oligodendrocyte or mammal.

Supplementary active compounds also can be incorporated into the compositions used in the methods of the invention. For example, a soluble Sp35 or TrkA polypeptide or a fusion protein may be coformulated with and/or coadministered with one or more additional therapeutic agents.

The invention encompasses any suitable delivery method for an Sp35 or TrkA antagonist to a selected target tissue, including bolus injection of an aqueous solution or implantation of a controlled-release system. Use of a controlled-release implant reduces the need for repeat injections.

The Sp35 or TrkA antagonists used in the methods of the invention may be directly infused into the brain. Various implants for direct brain infusion of compounds are known and are effective in the delivery of therapeutic compounds to human patients suffering from neurological disorders. These include chronic infusion into the brain using a pump, stereotactically implanted, temporary interstitial catheters, permanent intracranial catheter implants, and surgically implanted biodegradable implants. See, e.g., Gill et al., supra; Scharfen et al., "High Activity Iodine-125 Interstitial Implant For Gliomas," *Int. J. Radiation Oncology Biol. Phys.* 24(4):583-591 (1992); Gaspar et al., "Permanent 125I Implants for Recurrent Malignant Gliomas," *Int. J. Radiation Oncology Biol. Phys.* 43(5):977-982 (1999); chapter 66, pages 577-580, Bellezza et al., "Stereotactic Interstitial Brachytherapy," in Gildenberg et al., Textbook of Stereotactic and Functional Neurosurgery, McGraw-Hill (1998); and Brem et al., "The Safety of Interstitial Chemotherapy with BCNU-Loaded Polymer Followed by Radiation Therapy in the Treatment of Newly Diagnosed Malignant Gliomas: Phase I Trial," *J. Neuro-Oncology* 26:111-23 (1995).

The compositions may also comprise an Sp35 or TrkA antagonist dispersed in a biocompatible carrier material that functions as a suitable delivery or support system for the compounds. Suitable examples of sustained release carriers include semipermeable polymer matrices in the form of shaped articles such as suppositories or capsules. Implantable or microcapsular sustained release matrices include polylactides (U.S. Pat. No. 3,773,319; EP 58,481), copolymers of L-glutamic acid and gamma-ethyl-L-glutamate (Sidman et al., *Biopolymers* 22:547-56 (1985)); poly(2-hydroxyethyl-methacrylate), ethylene vinyl acetate (Langer et al., *J. Biomed. Mater. Res.* 15:167-277 (1981); Langer, *Chem. Tech.* 12:98-105 (1982)) or poly-D-(−)-3hydroxybutyric acid (EP 133,988).

In some embodiments of the invention, an Sp35 or TrkA antagonist is administered to a patient by direct infusion into an appropriate region of the brain. See, e.g., Gill et al., "Direct brain infusion of glial cell line-derived neurotrophic factor in Parkinson disease," *Nature Med.* 9: 589-95 (2003). Alternative techniques are available and may be applied to administer an Sp35 antagonist according to the invention. For example, stereotactic placement of a catheter or implant can be accomplished using the Riechert-Mundinger unit and the ZD (Zamorano-Dujovny) multipurpose localizing unit. A contrast-enhanced computerized tomography (CT) scan, injecting 120 ml of omnipaque, 350 mg iodine/ml, with 2 mm slice thickness can allow three-dimensional multiplanar treatment planning (STP, Fischer, Freiburg, Germany). This equipment permits planning on the basis of magnetic resonance imaging studies, merging the CT and MRI target information for clear target confirmation.

The Leksell stereotactic system (Downs Surgical, Inc., Decatur, Ga.) modified for use with a GE CT scanner (General Electric Company, Milwaukee, Wis.) as well as the Brown-Roberts-Wells (BRW) stereotactic system (Radionics, Burlington, Mass.) can be used for this purpose. Thus, on the morning of the implant, the annular base ring of the BRW stereotactic frame can be attached to the patient's skull. Serial CT sections can be obtained at 3 mm intervals though the (target tissue) region with a graphite rod localizer frame clamped to the base plate. A computerized treatment planning program can be run on a VAX 11/780 computer (Digital Equipment Corporation, Maynard, Mass.) using CT coordinates of the graphite rod images to map between CT space and BRW space.

The methods of treatment of disorders as described herein are typically tested in vitro, and then in vivo in an acceptable animal model, for the desired therapeutic or prophylactic activity, prior to use in humans. Suitable animal models, including transgenic animals, are will known to those of ordinary skill in the art. For example, in vitro assays to demonstrate the differentiation and survival effect of the Sp35 or TrkA antagonists are described herein. The effect of the Sp35 or TrkA antagonists on myelination of axons can be tested in vitro as described in the Examples. Finally, in vivo tests can be performed by creating transgenic mice which express the Sp35 or TrkA antagonist or by administering the Sp35 or TrkA antagonist to mice or rats in models as described herein.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning: A Laboratory Manual (3-Volume Set), J. Sambrook, D. W. Russell, Cold Spring Harbor Laboratory Press (2001); Genes VIII, B. Lewin, Prentice Hall (2003); PCR Primer, C. W. Dieffenbach and G. S. Dveksler, CSHL Press (2003); DNA Cloning, D. N. Glover ed., Volumes I and II (1985); Oligonucleotide Synthesis: Methods and Applications (Methods in Molecular Biology), P. Herdewijn (Ed.), Humana Press (2004); Culture of Animal Cells: A Manual of Basic Technique, 4th edition, R. I. Freshney, Wiley-Liss (2000); Oligonucleotide Synthesis, M. J. Gait (Ed.), (1984); Mullis et al. U.S. Pat. No. 4,683,195; Nucleic Acid Hybridization, B. D. Hames & S. J. Higgins eds. (1984); Nucleic Acid Hybridization, M. L. M. Anderson, Springer (1999); Animal Cell Culture and Technology, 2nd edition, M. Butler, BIOS Scientific Publishers (2004); Immobilized Cells and Enzymes: A Practical Approach (Practical Approach Series), J. Woodward, Irl Pr (1992); Transcription And Translation, B. D. Hames & S. J. Higgins (Eds.) (1984); Culture Of Animal Cells, R. I. Freshney, Alan R. Liss, Inc., (1987); Immobilized Cells And Enzymes, IRL Press, (1986); A Practical Guide To Molecular Cloning, 3rd edition, B. Perbal, John Wiley & Sons Inc. (1988); the treatise, Methods In Enzymology, Academic Press, Inc., N.Y.; Gene Transfer Vectors For Mammalian Cells, J. H. Miller and M. P. Calos eds., Cold Spring Harbor Laboratory (1987); Methods In Enzymology, Vols. 154 and 155, Wu et al. (Eds.); Immunochemical Methods In Cell And Molecular Biology, Mayer and Walker, (Eds.), Academic Press, London (1987); Handbook Of Experimental Immunology, Volumes I-IV, D. M. Weir and C. C. Blackwell (Eds.), (1986); Immunology Methods Manual: The Comprehensive Sourcebook of Techniques (4 Volume Set), 1st edition, I. Lefkovits, Academic Press (1997); Manipulating the Mouse Embryo: A Laboratory Manual, 3rd edition, Cold Spring Harbor Laboratory Press (2002); and in Ausubel et al., Current Protocols in Molecular Biology, John Wiley and Sons, Baltimore, Md. (1989).

General principles of antibody engineering are set forth in Antibody Engineering: Methods and Protocols (Methods in Molecular Biology), B. L. Lo (Ed.), Humana Press (2003); Antibody engineering, R. Kontermann and S. Dubel (Eds.), Springer Verlag (2001); Antibody Engineering, 2nd edition, C. A. K. Borrebaeck (Ed.), Oxford Univ. Press (1995). General principles of protein engineering are set forth in Protein Engineering, A Practical Approach, Rickwood, D., et al. (Eds.), IRL Press at Oxford Univ. Press, Oxford, Eng. (1995). General principles of antibodies and antibody-hapten binding are set forth in: Antibodies: A Laboratory Manual, E. Harlow and D. Lane, Cold Spring Harbor Laboratory Press (1988); Nisonoff, A., Molecular Immunology, 2nd edition, Sinauer Associates, Sunderland, Mass. (1984); and Steward, M. W., Antibodies, Their Structure and Function, Chapman and Hall, New York, N.Y. (1984). Additionally, standard methods in immunology known in the art and not specifically described are generally followed as in Current Protocols in Immunology, John Wiley & Sons, New York; Stites et al. (Eds.), Immunochemical Protocols (Methods in Molecular Biology), 2nd edition, J. D. Pound (Ed.), Humana Press (1998), Weir's Handbook of Experimental Immunology, 5th edition, D. M. Weir (Ed.), Blackwell Publishers (1996), Methods in Cellular Immunology, 2nd edition, R. Fernandez-Botran, CRC Press (2001); Basic and Clinical Immunology, 8th edition, Appleton & Lange, Norwalk, Conn. (1994) and Mishell and Shiigi (Eds.), Selected Methods in Cellular Immunology, W.H. Freeman and Co., New York (1980).

Standard reference works setting forth general principles of immunology include Current Protocols in Immunology, John Wiley & Sons, New York; Klein, J.; Kuby Immunology, 4th edition, R. A. Goldsby, et al., H. Freeman & Co. (2000); Basic and Clinical Immunology, M. Peakman, et al., Churchill Livingstone (1997); Immunology, 6th edition, I. Roitt, et al., Mosby, London (2001); Cellular and Molecular Immunology, 5th edition; A. K. Abbas, A. H. Lichtman, Elsevier—Health Sciences Division (2005); Immunology Methods Manual: The Comprehensive Sourcebook of Techniques (4 Volume Set), 1st edition, I. Lefkovits, Academic Press (1997) Immunology, 5th edition, R. A. Goldsby, et al., W. H. Freeman (2002); Monoclonal Antibodies: Principles and Practice, 3rd Edition, J.W. Goding, Academic Press (1996); Immunology: The Science of Self-Nonself Discrimination, John Wiley & Sons, New York (1982); Kennett, R., et al. (Eds.), Monoclonal Antibodies, Hybridoma: A New Dimension in Biological Analyses, Plenum Press, New York (1980); Campbell, A., "Monoclonal Antibody Technology" in Burden, R., et al. (Eds.), Laboratory Techniques in Biochemistry and Molecular Biology, Vol. 13, Elsevere, Amsterdam (1984).

All of the references cited above, as well as all references cited herein, are incorporated herein by reference in their entireties.

EXAMPLES

Example 1

Sp35 Co-Localizes with TrkA in Different Types of Neurons

The expression of Sp35 and TrkA, in various neurons, was confirmed by in situ hybridization and immunohistochemistry of neurons derived from the cortex, hippocampus, brainstem, cerebellum, olfactory bulb and dorsal root ganglion (DRG) of brain and spinal cord tissue from rat. Rat brain, spinal cord, and dorsal root ganglia frozen sections were prepared and processed as described in Mi et al., Nature 403:785-789 (2000). Sections were probed with digoxigenin-labeled Sp35 anti-sense and sense RNA. Sections were stained using the Tyramide Signal Amplification (Amersham Biosciences) plus a fluorescence anti-digoxigenin conjugated antibodies kit (Perkin Elmer) following the manufacturer's instructions. For combined in situ and immunohistochemistry analyses, cultures were first probed with the digoxigenin-labeled Sp35 RNAs and then with anti-TrkA antibody (Santa Cruz). Nuclei were stained with DAPI. Results of the Sp35 in situ hybridization and immunohistochemistry experiment in various neurons is shown in FIG. 1. Sp35 and TrkA co-localize within the various neurons examined.

Co-localization of Sp35 and TrkA was also examined in DRG neurons in culture. Embryonic dorsal root ganglia (DRG) neurons were grown in vitro as previously described in Mi et al., Nat. Neurosci. 8:745-51 (2005) and Kleitman et al. "Tissue culture methods for the study of myelination." Culturing Nerve Cells. Banker and Goslin, eds. Cambridge Mass.: MIT Press, 337-377 (1991). Briefly, dorsal root ganglia, dissected from embryonic day 15 (E15) Long Evan rats, were plated on poly-D-lysine (100 µg/ml)-coated cover slips for 2 weeks and grown in Neurobasal medium supplemented with B27 (Invitrogen) in the presence or absence of 100 ng/ml nerve growth factor (BD Biosciences). To remove proliferating glial cells, the cultures were pulsed twice with fluorodeoxyuridine (20 µM) from days 2-6 and from days 8-10. Samples were prefixed in 4% paraformaldehyde and incubated with the indicated antibodies using standard protocols. Briefly, tissues sections were incubated in primary antibodies overnight at 4° C., washed thoroughly, incubated with an appropriately Alexa-labeled secondary antibody (Molecular Probes, Inc) for 2 hr, then mounted in VectaMount (Victor) and visualized by fluorescence microscopy. Cultures were incubated for 2 hr in primary and 1 hr in Alexa-labeled secondary antibodies, and visualized by fluorescence microscopy. Anti-Sp35 antibody was generated from a human Fab phage display library (Antibody 1968-Morphosys). Anti-TrkA antibody was obtained from Santa Cruz Biotechnology, Inc. Nuclei were stained with DAPI. Sp35 and TrkA co-localize in DRG neurons is tissue culture as well, as shown in FIG. 2.

Example 2

Sp35 Binds to TrkA by Immunoprecipitation

Direct interaction between Sp35 and TrkA in cultured 293T cells was demonstrated by immunoprecipitation using anti-Sp35 or anti-TrkA antibody (see FIG. 3). 293 cells (100 mm dishes) were transfected with a plasmid containing either Sp35, TrkA, or a combination of Sp35/TrkA, Sp35/p75, TrkA/p75 and Sp35/p75/TrkA. The cells were harvested after 48 hr and lysed in 1 ml lysis buffer (50 mM HEPES, pH 7.5, 150 mM NaCl, 1.5 mM MgCl2, 1 mM EGTA, 1% Triton X-100 and 10% glycerol) for 30 min at 4° C. After centrifugation at 14,000×g for 15 min, the supernatants were incubated with ProteinA/G-Sepharose beads (Santa Cruz) at 4° C. for 1 hr, and then incubated at 4° C. for 1 hr with either affinity-purified rabbit anti-Sp35 antibody or mouse anti-Trk antibody (Santa Cruz). The beads were washed 3 times with lysis buffer, boiled in Laemmli sample buffer, subjected to 4-20% SDS-PAGE, and analyzed by Western blotting with mouse anti-Trk antibody (Santa Cruz) or anti-Sp35 antibody (Biogen Idec). The TrkA and Sp35 antibodies were visualized using anti-mouse IgG-HRP and anti-rabbit IgG-HRP (Bio-Rad), respectively. Sp35 interacted with TrkA alone as well as in the presence of p75. See FIG. 3.

Example 3

Sp35 Inhibits Phosphorylation of TrkA

TrkA phosphorylation was examined in oligodendrocyte-DRG co-cocultures. Oligodendrocytes mature through several developmental stages from A2B5 progenitor cells (which express A2B5), differentiating into pre-myelinating oligodendrocytes (which express O1 and O4) and finally into mature myelinating oligodendrocytes (which express O1, O4 and MBP). Thus, by monitoring the presence and absence of the A2B5, O1, O4 and MBP markers it is possible to determine a given cell's developmental stage. For a general review of oligodendrocyte biology, see, e.g., Baumann and Pham-Dinh, *Physiol. Rev.* 81: 871-927 (2001).

Enriched populations of oligodendrocytes were grown from Female Long Evans post-natal day 2 (P2) rats. Briefly, the forebrain was dissected out and placed in Hank's buffered salt solution (HBSS) (Invitrogen, Grand Island, N.Y.). The tissue was cut into 1 mm fragments and incubated at 37° C. for 15 min in 0.01% trypsin and 10 µg/ml DNase. Dissociated cells were plated on poly-L-lysine-coated T75 tissue culture flasks and grown at 37° C. for 10 days in DMEM medium with 20% fetal calf serum (Invitrogen). Oligodendrocyte precursors (A2B5+) were collected by shaking the flask overnight at 200 rpm at 37° C., resulting in a 95% pure population. Cultures were maintained in high glucose DMEM medium containing FGF/PDGF (Peprotech) (10 ng/ml) for 1 week.

DRG cultures were prepared as follows. Embryonic dorsal root ganglia (DRG) neurons were grown in vitro as previously described in Mi et al., *Nat. Neurosci.* 8:745-51 (2005) and Kleitman et al. "Tissue culture methods for the study of myelination." *Culturing Nerve Cells.* Banker and Goslin, eds. Cambridge Mass.: MIT Press, 337-377 (1991). Briefly, dorsal root ganglia, dissected from embryonic day 15 (E15) Long Evans rats, were plated on poly-D-lysine (100 µg/ml)-coated cover slips for 2 weeks and grown in Neurobasal medium supplemented with B27 (Invitrogen) in the presence or absence of 100 ng/ml nerve growth factor (BD Biosciences). To remove proliferating glial cells, the cultures were pulsed twice with fluorodeoxyuridine (20 µM) from days 2-6 and from days 8-10.

Oligodendrocyte-DRG co-cultures were prepared as follows. A2B5+ oligodendrocyte progenitor cells and DRG neuron drop cultures were prepared as above. One day after oligodendrocyte progenitors were added to DRG neurons, co-cultures were infected with lentivirus expressing GFP (control), dominant-negative Sp35 or full length Sp35 at 2 MOI per cell. DNA sequences used for lentiviral construction were, mouse Sp35 full length (FL-Sp35, encoding amino acid residues 34-614), Sp35 dominant negative (DN-Sp35, encoding amino acid residues 34-581). DNA sequences were inserted into the NotI and BamHI sites of HRST-IRESeGFP lentivirus vector. Plasmids were transfected into 293FT cells to produce lentivirus as described in Rubinson et al. *Nat. Genetics* 33:401-406 (2003).

Fresh media was changed every three days. Cells were harvested after 48 hr and lysed in 1 ml lysis buffer (50 mM HEPES, pH 7.5, 150 mM NaCl, 1.5 mM MgCl2, 1 mM EGTA, 1% Triton X-100 and 10% glycerol) for 30 min at 4° C. Lysates were subjected to 4-20% SDS-PAGE, and analyzed by Western blotting with mouse anti-Trk antibody (Santa Cruz) or an antibody to phosphorylated TrkA (Sigma).

As shown in FIG. 4, in the presence of DN-Sp35, phosphorylation of TrkA is increased when compared to TrkA in the presence of full-length Sp35 or a control (GFP).

Example 4

Soluble Sp35-Fc and TrkA-Fc Promote Myelination and Oligodendrocyte Differentiation in the Presence of Nerve Growth Factor (NGF)

The state of myelination was examined in the presence of the TrkA ligand NGF and an Sp35 antagonist. The Sp35 antagonist Sp35-Fc was used in all experiments. Sp35-Fc contains the extra-cellular portion of human Sp35 (residues 1-532) fused to the hinge and Fc region of human IgG1 and was prepared as described in U.S. Patent Application Publication No. 2006/0009388 A1, which is incorporated herein by reference in its entirety.

Oligodendrocyte/DRG co-cultures were prepared as described in Example 3. The co-cultures were treated with increasing concentrations of Sp35-Fc or control-Fc for 3 weeks. Monoclonal antibodies against MBP were used to determine MBP protein concentration and for immunofluorescence experiments (Sternberger Monoclonals). See FIG. 5.

Myelination is inhibited normally in co-culture in the presence of NGF. However, as shown in FIG. 5, the number of MBP+ oligodendrocytes increased when the Sp35 antagonist Sp35-Fc was added to the co-culture. The number of MBP+ cells increased as the concentration of the Sp35 antagonist increased.

Additionally, oligodendrocyte/DRG co-cultures, in 100 ng/ml NGF, were examined for the expression of the myelin protein MBP after 14 days in the presence of a control IgG protein or the 1A7 Sp35 monoclonal antibody (Biogen IDEC). Oligodendrocyte/DRG co-cultures were also examined for the expression of the MBP protein in the absence of NGF and in the presence of the TrkA-Fc protein. The use of the TrkA-Fc protein in similar assays was described in Chan et al., Neuron 43: 154-5 (2004). MBP protein was visualized in the co-cultures by immunofluorescent staining using the following procedure. Samples were prefixed in 4% paraformaldehyde and incubated with an MBP antibody using standard protocols. Samples were incubated in primary antibodies overnight at 4° C., washed thoroughly, incubated with the appropriate Alexa-labeled secondary antibody (Molecular Probes, Inc) for two hours and then mounted in VectaMount (Vector) and visualized by fluorescent microscopy.

In the presence Sp35-Fc, there is an enhancement of MBP positive oligodendrocytes and myelin internodes when compared to controls (FIG. 13). Additionally, the removal of exogenous NGF with the NGF scavenger TrkA-Fc, resulted in a similar enhancement of differentiation and myelination of oligodendrocytes (FIG. 13).

Example 5

Dominant-Negative Sp35 and Dominant-Negative TrkA Promote Myelination and Oligodendrocyte Differentiation in the Presence of Nerve Growth Factor (NGF)

CNS myelination in the presence of NGF and either an Sp35 antagonist (Sp35-DN) or a TrkA antagonist (TrkA-DN) was examined. 3 week old DRG and oligodendrocyte cocultures (prepared as described in Example 3) were infected with lentiviruses, at an MOI of 2 per cell, expressing either full-length or dominant negative Sp35, full-length or dominant negative Nogo Receptor, full-length or dominant negative Taj, full-length or dominant negative p75, and full-length or dominant negative TrkA. Lentiviruses were prepared as described in Example 3 and as follows. Rat p75 full length (FL-p75, amino acid residues 1-425), p75 dominant negative (DN-p75, amino acid residues 1-275), human TrkA full length (FL-TrkA, amino acid residues 1-796), TrkA dominant negative (DN-TrkA, amino acid residues 1-441), human Taj full length (FL-Taj, amino acid residues 1-417), Taj dominant negative (DN-Taj, amino acid residues 1-192), rat Nogo receptor full length (FL-NgR, amino acid residues 1-473), Nogo receptor dominant negative (DN-NgR, amino acid residues 28-310). DNA sequence was inserted into the NotI and BamHI sites of HRST-IRESeGFP lentivirus vector. Plasmids were transfected into 293 cells to produce lentivirus as described in Rubinson et al. Nat. Genetics 33:401-406 (2003).

Co-culture lysates were examined at 3 weeks and analyzed by Western blot as described previously. The blots were probed with polyclonal antibodies to MAG and to MBP. The myelin proteins MAG and MBP were used as markers for myelination.

for 30 minutes at 37° C. Dissociated cells were plated on poly-D-lysine-coated 60 mm tissue culture plates and grown at 37° C. in DMEM medium with 10% fetal bovine serum (Invitrogen). Contaminating cell types were eliminated by treating with 5 μM cytosine arabinoside from day 2 to day 5 in culture with fresh medium change on day 4. Forskolin (4 μM) and bovine pituitary extract (20 μM) were added in culture after cytosine arabinoside removal. DRGs were cultured as previously described.

RT-PCR for TrkA, Sp35 and GAPDH was performed on purified OPCs, SCs and DRGs in the presence or absence of NGF or BDNF as follows. Cultures of OPCs, SCs and DRGs were prepared as described above. Wells of the tissue culture dishes were treated with either 100 ng/ml of NGF or 100 ng/ml of BDNF for 24 hours prior to mRNA isolation. Cellular mRNA was extracted using the Absolutely RNA miniprep kit (Stratagene). Equal amounts of mRNA were subjected to RT-PCR. The primer sets used for the PCR reactions are as follows:

```
Sp35 (forward primer)   5'-AGAGACATGCGATTGGTGA-3' (SEQ ID NO: 10)

Sp35 (reverse primer)   5'-AGAGATGTAGACGAGGTCATT-3' (SEQ ID NO: 11)

TrkA (forward primer)   5'-TGACTTCGTTGATGCTGGC-3' (SEQ ID NO: 12)

TrkA (reverse primer)-  5'-CTGTAGGGCCTGCCCCTCCAC-3'). (SEQ ID NO: 13)
```

As shown in FIG. 6, expression of DN-TrkA or DN-Sp35 in the co-cultures resulted in increased expression of MBP and MAG, indicating an increase in oligodendrocyte differentiation and myelination relative to control cells or cells infected with FL-TrkA or FL-Sp35 lentiviruses. Antagonists to Taj, Nogo Receptor and p75 did not result in expression of myelin proteins.

The TrkA compound antagonist K525a was also tested in DRG-oligodendrocyte cocultures for its ability to promote myelination. At concentrations of 3 nM and 1 nM, K525a promoted myelination, as measured by the presence of MBP, similarly to the Sp35 antagonist Sp35-Fc. See FIG. 7.

Example 6

Testing for Sp35 and TrkA Expression in OPCs, SCs and DRGs-NGF Induces Sp35 Expression in DRGs but not in Oligodendrocytes The expression of TrkA and Sp35 were examined in oligodendrocyte progenitor cells (OPCs), Schwann Cells (SCs) and dorsal root ganglion cells (DRGs). Enriched populations of OPCs were isolated from Female Long Evans postnatal day 2 (P2) rats. Briefly, the forebrains were removed and placed in Hank's buffered salt solution (HBSS) (Invitrogen). The tissue was cut into 1 mm fragments and incubated at 37° C. for 15 min in 0.01% trypsin and 10 μg/ml DNase. Dissociated cells were plated on poly-L-lysine-coated T75 tissue culture flasks and grown at 37° C. for 10 days in DMEM medium with 20% fetal bovine serum (Invitrogen). OPCs (A2B5+) were collected by shaking the flask overnight at 200 rpm at 37° C., resulting in 95% purity. Cultures were maintained in high glucose DMEM medium containing FGF/PDGF (10 ng/ml, Peprotech) for 1 week.

Enriched Schwann cells were collected from the Long Evans postnatal day 2 (P2) rats. Briefly, the sciatic nerves were extracted and minced into small pieces in L15 medium (Biogen Idec). The tissues were first incubated in 0.1% collagenase I for 30 minutes, then in trypsin-EDTA (Invitrogen)

OPCs expressed Sp35, but did not express detectable levels of the mRNA for TrkA, as shown in FIG. 9A. SCs did not express detectable amounts of mRNA for either molecule, while DRGs expressed both TrkA and Sp35 with an induction of Sp35 mRNA when treated with NGF.

Oligodendrocyte—DRG co-cultures were prepared as described previously. Various concentrations of NGF (0, 10, 50 and 100 ng/ml) were added to oligodendrocyte—DRG co-cultures, DRG neuronal cultures and oligodendrocyte cultures. In all cultures expression of Sp35 and phosphorylated TrkA was examined by Northern blot or immuno-histochemical staining.

In the presence of NGF, Sp35 expression increased in oligodendrocyte/DRG cocultures as shown in FIG. 8. However, when cultured oligodendrocytes were tested, Sp35 expression remained constant and was not upregulated. See FIG. 9. Upregulation of Sp35 in DRG neurons was further confirmed by immunofluorescence of DRG neurons in the presence of 100 ng/ml of NGF. See FIG. 10.

Example 7

TrkA is a Signaling Molecule Upstream of Sp35

The myelin proteins MAG and MBP were used to determine whether TrkA was upstream of Sp35 in inhibiting myelination in DRG-oligodendrocyte co-cultures. Oligodendrocyte-DRG co-cultures were prepared as described in Example 3. One day after oligodendrocyte progenitors were added to DRG neurons, co-cultures were infected with lentivirus, in the presence of 100 ng/ml NGF, expressing GFP (control), dominant-negative Sp35, full length Sp35, full length TrkA or dominant negative TrkA at 2 MOI per cell. DNA sequences used for lentiviral construction were, mouse Sp35 full length (FL-Sp35, encoding amino acid residues 34-614), Sp35 dominant negative (DN-Sp35, encoding amino acid residues 34-581), human TrkA full length (FL-TrkA, encoding amino acid residues 1-796) and TrkA dominant negative (DN-TrkA encoding amino acid residues 1-441). Lentiviruses were constructed as described in Example 3 and 4.

Fresh media was changed every three days. Cells were harvested after 48 hr and lysed in 1 ml lysis buffer (50 mM HEPES, pH 7.5, 150 mM NaCl, 1.5 mM MgCl2, 1 mM EGTA, 1% Triton X-100 and 10% glycerol) for 30 min at 4° C. Lysates were subjected to 4-20% SDS-PAGE, and analyzed by Western blotting with an antibody to MBP, MAG and Sp35. The blots were probed with polyclonal antibodies to MAG and to MBP.

In the presence of DN-Sp35 and full length TrkA, the myelin proteins MAG and MBP could be detected. However, when DN-TrkA and full-length Sp35 were co-transfected, MBP and MAG could not be detected, indicating that the inhibition of myelination and oligodendrocyte differentiation by Sp35 was downstream of the TrkA signal to inhibit myelination. See FIG. 11.

Example 8

Axonal Sp35 does not Influence Schwann Cell Myelination

The developmental profile for the expression of Sp35, TrkA, MBP, MAG and β-actin were examined in the developing rat sciatic nerve (peripheral) and spinal cord (central nervous system) was examined. Tissue from postnatal day 0, 2, 4, 6, 8, 10, 20 and adult were isolated and prepared for Western blot analysis. In the rat spinal cord, the down-regulation of Sp35 during development correlated with a decrease in TrkA expression and the intitiation of myelination (MBP and MAG expression). See FIG. 12A. There was less of a correlation between Sp35 downregulation and a decrease in TrkA expression in the sciatic nerve. See FIGS. 12A and 12B.

While NGF/TrkA inhibits myelination by oligodendrocytes, it promotes myelination by SCs. (Chan et al., Neuron 43:183-91 (2004)). Thus, the role of axonal Sp35 in promoting myelination by SCs was examined. Purified SC cultures were established as previously described. After cells were 80-90% confluent, Schwann cells were seeded onto purifed DRG neurons to produce SC/DRG co-cultures. The expression of TrkA, Sp35, MAG and P0 were analyzed by Western blot. Cultures were extracted after seeding the SCs onto the DRGs for 3 days (DRG/SC), at the day of induction of myelination by the addition of absorbic acid (Day 0), and at 2, 4, 6, 8 and 10 days after induction. In culture, Sp35 expression did not seem to correlate with the downregulation of TrkA or the initiation of the SC myelination. See FIG. 12C.

Lentiviruses expressing FL-Sp35 and DN-Sp35, as described previously, were used to infect the SC/DRG co-cultures. The SC/DRG co-cultures were infected with lentivirus at an MOI of 2. Myelination was analyzed by Western blot for MAG, P0 and β-actin. The expression of the myelin proteins was unaltered by the expression of FL-Sp35 or DN-Sp35, illustrating that Sp35 does not influence Schwann cell myelination. See FIG. 12D.

Example 9

TrkA Antagonists Promote Myelination In Vivo

Adult wild-type C57B1/6 male mice are fed cuprizone (0.2% milled with ground mouse chow by weight) for 6 weeks to induce demyelination within the corpus callosum. Various antagonists of TrkA are stereotactically injected into the demyelinating corpus callosum at 2, 2.5, and 3 weeks of cuprizone feeding. Control mice are stereotactically injected at the same intervals with sterilized media containing no TrkA antagonist. After 6 weeks of cuprizone feeding, the mice are returned to a normal diet for 2, 4 and 6 weeks (ground mouse chow only) to allow remyelination.

The cuprizone-treated mice are anesthetized with ketamine (80 mg/kg body weight) and xylazine (10 mg/kg body weight) and positioned in an immobilization apparatus designed for stereotactic surgery (David Kopf Instruments). The scalp is opened and the sterile compounds injected (1 μM in 1 ml of HBSS) unilaterally into the acutely demyelinated corpus callosum of the wild-type recipient mice with a 10 ml Hamilton syringe using stereotactic coordinates of 0.7 mm posterior and 0.3 mm lateral to bregma at a depth of 1.7 mm (Messier et al., Pharmacol. Biochem. Behav. 63(2): 313-18 (1999)). Additionally, control recipient mice are stereotactically injected with HBSS containing no compounds. The opening in the skull is filled with Gelfoam, and the area is swabbed with penicillin and streptomycin (Gibco) and the wound is sutured. Post injection, mice are sacrificed every week of the experiment and their brains are removed and processed for molecular, biochemical and histological analysis.

The animals receiving TrkA antagonist treatment will be examinaed for axon myelination by IHC using anti-MBP protein antibody or luxol fast blue and compared to control animals.

Example 10

TrkA Anatgonists Promote Neuronal Survival after Spinal Cord Injury (SCI) In Vivo Spinal cord injury is induced in adult female Long Evans rats (190-210 g; Charles River). A dorsal hemisection is performed at T6/T7, completely interrupting the main dorsomedial and the minor dorsolateral corticospinal tract (CST) components. The cord is sterotaxically transected at a depth of 1.8 mm from the surface using a microscalpel. Immediately after CST transection, an intrathecal catheter is inserted into the subarachnoid space at T7 and connected to a primed mini-osmotic pump (Alzet model 2004, Alza Corp.) inserted into the subcutaneous space. The mini-osmotic pumps deliver 0.25 μl/h of 25 μM TrkA-Fc fusion protein, or an antagonist TrkA antibody, or either human IgG (5 mg/ml) or PBS as controls. Postoperative care comprises analgesia (Buprenorphine/Buprenex, Reckitt Benckiset Healthcare Ltd., 0.05 mg/kg subcutaneously) every 8-12 hours for 3 days and antibiotic treatment (ampicillin, Bristol Myers Squibb, 100 mg/kg subcutaneously twice daily) for 7 days after surgery. Bladders are expressed manually twice a day for the duration of the study (4 weeks) or until return of function. On completion of the study, rats are anesthetized and trans-cardially perfused with heparinized saline followed by 4% paraformaldehyde (PFA). The spinal cords are removed, embedded in paraffin, and 10 μm sections are cut from for histological analysis.

To quantify apoptotic cell death after SCI, animals are euthanized 3 or 7 days after SCI and stained using anti-activated-Caspase-3 antibody (Cell Signaling Technologies) and TUNEL staining (Promega). The sections are also stained with anti-NeuN antibody (Chemicon) and anti-CC1 antibody (Calbiochem) to identify neurons and oligodendrocytes, respectively.

The number of activated-Caspase-3-positive neurons and oligodendrocytes in the TrkA-Fc-treated animals will be compared to the controls 3 days after SCI. Furthermore, four weeks after SCI, neurons and oligodendrocytes which survived in the spinal cord tissue surrounding the lesion site in TrkA-Fc-treated animals will be compared to the controls base on staining with anti-βIII-tubulin antibody (neuronal survival) and anti-O4 antibody (oligodendrocyte survival).

The present invention is not to be limited in scope by the specific embodiments described which are intended as single illustrations of individual aspects of the invention, and any compositions or methods which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

All publications and patent applications mentioned in this specification are herein incorporated by reference to the same extent as if each individual publication or patent application was specifically and individually indicated to be incorporated by reference.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

What is claimed is:

1. A method for promoting myelination of central nervous system (CNS) neurons, comprising contacting a mixture of CNS neurons and oligodendrocytes with a composition comprising a TrkA antagonist consisting of residues 36-441 of SEQ ID NO: 4 or residues 1-441 of SEQ ID NO: 4.

2. The method of claim 1, wherein said TrkA antagonist polypeptide further comprises a non-TrkA moiety.

3. The method of claim 2, wherein said non-TrkA moiety is selected from the group consisting of an antibody Ig moiety, a serum albumin moiety, a targeting moiety, a reporter moiety, and a purification-facilitating moiety.

4. The method of claim 1, wherein said TrkA antagonist polypeptide is conjugated to a polymer.

5. The method of claim 4, wherein the polymer is a polyalkylene glycol.

6. A method for promoting survival of CNS neurons in a mammal, comprising administering to a mammal in need thereof an effective amount of a composition comprising a TrkA antagonist consisting of residues 36-441 of SEQ ID NO: 4 or residues 1-441 of SEQ ID NO: 4.

7. The method of claim 6, wherein said CNS neurons and oligodendrocytes are in a mammal and said mammal has been diagnosed with a disease, disorder, or injury involving demyelination, dysmyelination, or neurodegeneration.

8. The method of claim 7, wherein said disease, disorder, or injury is selected from the group consisting of multiple sclerosis (MS), progressive multifocal leukoencephalopathy (PML), encephalomyelitis (EPL), central pontine myelolysis (CPM), adrenoleukodystrophy, Alexander's disease, Pelizaeus Merzbacher disease (PMZ), Wallerian Degeneration, optic neuritis, transverse myelitis, amylotrophic lateral sclerosis (ALS), Huntington's disease, Alzheimer's disease, Parkinson's disease, spinal cord injury, traumatic brain injury, post radiation injury, neurologic complications of chemotherapy, stroke, acute ischemic optic neuropathy, vitamin E deficiency, isolated vitamin E deficiency syndrome, AR, Bassen-Kornzweig syndrome, Marchiafava-Bignami syndrome, metachromatic leukodystrophy, trigeminal neuralgia, acute dissmeminated encephalitis, Guillian-Barre syndrome, Marie-Charcot-Tooth disease and Bell's palsy.

9. A method for inhibiting Sp35 expression in CNS neurons comprising contacting CNS neurons with a composition comprising a TrkA antagonist consisting of residues 36-441 of SEQ ID NO: 4 or residues 1-441 of SEQ ID NO: 4.

10. The method of claim 9, wherein said CNS neurons are in a mammal, and wherein said contacting comprises administering an effective amount of said TrkA antagonist to a mammal in need thereof.

* * * * *